US011007296B2

(12) United States Patent
Gross et al.

(10) Patent No.: US 11,007,296 B2
(45) Date of Patent: May 18, 2021

(54) DRUG-ELUTING SELF-RETAINING SUTURES AND METHODS RELATING THERETO

(75) Inventors: Jeffrey M. Gross, Carlsbad, CA (US); Lev Drubetsky, Coquitlam (CA); Alexander Naimagon, Richmond (CA); Rui Avelar, Goleta, CA (US); William L. D'Agostino, Hamden, CT (US); Kevin Don Nelson, Richardson, TX (US); Brent B. Crow, Grand Prairie, TX (US); Nickolas B. Griffin, Allen, TX (US)

(73) Assignees: Ethicon, Inc., Somerville, NJ (US); Ethicon, LLC, Guaynabo, PR (US); Tissuegen, Inc., Dallas, TX (US)

( * ) Notice: Subject to any disclaimer, the term of this patent is extended or adjusted under 35 U.S.C. 154(b) by 670 days.

(21) Appl. No.: 13/883,066

(22) PCT Filed: Nov. 3, 2011

(86) PCT No.: PCT/US2011/059238
§ 371 (c)(1),
(2), (4) Date: Aug. 7, 2013

(87) PCT Pub. No.: WO2012/061658
PCT Pub. Date: May 10, 2012

(65) Prior Publication Data
US 2013/0317545 A1 Nov. 28, 2013

Related U.S. Application Data

(60) Provisional application No. 61/409,731, filed on Nov. 3, 2010.

(51) Int. Cl.
A61B 17/06 (2006.01)
A61B 17/04 (2006.01)
(Continued)

(52) U.S. Cl.
CPC ........ *A61L 17/005* (2013.01); *A61B 17/0401* (2013.01); *A61B 2017/00526* (2013.01);
(Continued)

(58) Field of Classification Search
CPC .......... A61B 17/0401; A61B 17/06166; A61B 2017/00893; A61B 2017/06057;
(Continued)

(56) References Cited

U.S. PATENT DOCUMENTS 709,392 A 9/1902 Brown
733,723 A 7/1903 Lukens
(Continued)

FOREIGN PATENT DOCUMENTS

AU 2005244886 A1 12/2005
BE 1014364 9/2003
(Continued)

OTHER PUBLICATIONS

US 8,663,276 B2, 03/2014, Leung et al. (withdrawn)
(Continued)

*Primary Examiner* — Katherine H Schwiker
(74) *Attorney, Agent, or Firm* — Frost Brown Todd LLC

(57) ABSTRACT

A drug-eluting self-retaining suture comprises a filament, a plurality of retainers, and a drug impregnated in or coated on the filament. The shape and distribution of retainers modifies the in vivo release kinetics of the drug. The drug release kinetics may be modified uniformly or region by region. The self-retaining suture may for example be used for reattaching severed nerves and release nerve growth factor or other regeneration accelerating agents into the region of the nerve injury.

6 Claims, 26 Drawing Sheets

(51) Int. Cl.
*A61L 17/00* (2006.01)
*A61B 17/00* (2006.01)

(52) U.S. Cl.
CPC .............. *A61B 2017/00893* (2013.01); *A61B 2017/0608* (2013.01); *A61B 2017/06057* (2013.01); *A61B 2017/06176* (2013.01); *A61L 2300/414* (2013.01); *A61L 2300/602* (2013.01); *A61L 2430/32* (2013.01)

(58) Field of Classification Search
CPC .. A61B 2017/0608; A61B 2017/06176; A61B 2017/06171; A61B 2017/0618; A61B 2017/06185; A61B 2017/00663; A61B 2017/0412; A61B 2017/0429; A61B 2017/0619; A61B 2017/00858; A61L 17/005; A61L 2300/414; A61L 2300/602; A61L 2430/32

See application file for complete search history.

(56) References Cited

U.S. PATENT DOCUMENTS

| | | | |
|---|---|---|---|
| 816,026 A | 3/1906 | Meier | |
| 1,142,510 A | 6/1915 | Engle | |
| 1,728,316 A | 9/1929 | Von Wachenfeldt | |
| 1,886,721 A | 11/1932 | O'Brien | |
| 2,094,578 A | 10/1937 | Blumenthal et al. | |
| 2,201,610 A | 5/1940 | Dawson, Jr. | |
| 2,232,142 A | 2/1941 | Schumann | |
| 2,254,620 A | 9/1941 | Miller | |
| 2,347,956 A | 5/1944 | Lansing | |
| 2,355,907 A | 8/1944 | Cox | |
| 2,421,193 A | 5/1947 | Gardner | |
| 2,452,734 A | 11/1948 | Costelow | |
| 2,472,009 A | 5/1949 | Gardner | |
| 2,480,271 A | 8/1949 | Sumner | |
| 2,572,936 A | 10/1951 | Kulp et al. | |
| 2,591,063 A | 4/1952 | Goldberg | |
| 2,684,070 A | 7/1954 | Kelsey | |
| 2,736,964 A | 3/1956 | Lieberman | |
| 2,779,083 A | 1/1957 | Enton | |
| 2,817,339 A | 12/1957 | Sullivan | |
| 2,830,366 A | 4/1958 | Chisena | |
| 2,866,256 A | 12/1958 | Matlin | |
| 2,910,067 A | 10/1959 | White | |
| 2,928,395 A | 3/1960 | Forbes et al. | |
| 2,988,028 A | 6/1961 | Alcamo | |
| 3,003,155 A | 10/1961 | Mielzynski et al. | |
| 3,066,452 A | 12/1962 | Bott et al. | |
| 3,066,673 A | 12/1962 | Bott et al. | |
| 3,068,869 A | 12/1962 | Shelden et al. | |
| 3,068,870 A | 12/1962 | Levin | |
| 3,082,523 A | 3/1963 | Modes et al. | |
| 3,123,077 A | 3/1964 | Alcamo | |
| 3,166,072 A | 1/1965 | Sullivan, Jr. | |
| 3,187,752 A | 6/1965 | Glick | |
| 3,206,018 A | 9/1965 | Lewis et al. | |
| 3,209,652 A | 10/1965 | Burgsmueller | |
| 3,209,754 A | 10/1965 | Brown | |
| 3,212,187 A | 10/1965 | Benedict | |
| 3,214,810 A | 11/1965 | Mathison | |
| 3,221,746 A | 12/1965 | Noble | |
| 3,234,636 A | 2/1966 | Brown | |
| 3,273,562 A | 9/1966 | Brown | |
| 3,352,191 A | 11/1967 | Crawford | |
| 3,378,010 A | 4/1968 | Codling | |
| 3,385,299 A | 5/1968 | LeRoy | |
| 3,494,006 A | 2/1970 | Brumlik | |
| 3,522,637 A | 8/1970 | Brumlik | |
| 3,525,340 A | 8/1970 | Gilbert | |
| 3,545,608 A | 12/1970 | Berger et al. | |
| 3,557,795 A | 1/1971 | Hirsch | |
| 3,570,497 A | 3/1971 | Lemole | |
| 3,586,002 A | 6/1971 | Wood | |
| 3,608,095 A | 9/1971 | Barry | |
| 3,608,539 A | 9/1971 | Miller | |
| 3,618,447 A | 11/1971 | Goins | |
| 3,646,615 A | 3/1972 | Ness | |
| 3,683,926 A | 8/1972 | Suzuki | |
| 3,716,058 A | 2/1973 | Tanner, Jr. | |
| 3,720,055 A | 3/1973 | de Mestral et al. | |
| 3,748,701 A | 7/1973 | De Mestral | |
| 3,762,418 A | 10/1973 | Wasson | |
| 3,825,010 A | 7/1974 | McDonald | |
| 3,833,972 A | 9/1974 | Brumlik | |
| 3,845,641 A | 11/1974 | Waller | |
| 3,847,156 A | 11/1974 | Trumble | |
| 3,889,322 A | 6/1975 | Brumlik | |
| 3,918,455 A | 11/1975 | Coplan | |
| 3,922,455 A | 11/1975 | Brumlik | |
| 3,941,164 A | 3/1976 | Musgrave | |
| 3,977,937 A | 8/1976 | Candor | |
| 3,980,177 A | 9/1976 | McGregor | |
| 3,981,051 A | 9/1976 | Brumlik | |
| 3,981,307 A | 9/1976 | Borysko | |
| 3,985,138 A | 10/1976 | Jarvik | |
| 3,990,144 A | 11/1976 | Schwartz | |
| 4,006,747 A | 2/1977 | Kronenthal | |
| 4,008,303 A | 2/1977 | Glick et al. | |
| 4,024,871 A * | 5/1977 | Stephenson | 606/231 |
| 4,027,608 A | 6/1977 | Arbuckle | |
| 4,043,344 A | 8/1977 | Landi | |
| 4,052,988 A | 10/1977 | Doddi et al. | |
| D246,911 S | 1/1978 | Bess, Jr. et al. | |
| 4,069,825 A | 1/1978 | Akiyama | |
| 4,073,298 A | 2/1978 | Le Roy | |
| 4,075,962 A | 2/1978 | Mabry | |
| 4,098,210 A | 7/1978 | Wright | |
| 4,137,921 A | 2/1979 | Okuzumi et al. | |
| 4,182,340 A | 1/1980 | Spencer | |
| 4,186,239 A | 1/1980 | Mize et al. | |
| 4,198,734 A | 4/1980 | Brumlik | |
| 4,204,541 A | 5/1980 | Kapitanov | |
| 4,204,542 A | 5/1980 | Bokros et al. | |
| 4,259,959 A | 4/1981 | Walker | |
| 4,278,374 A | 7/1981 | Wolosianski | |
| 4,300,424 A | 11/1981 | Flinn | |
| 4,311,002 A | 1/1982 | Hoffmann et al. | |
| 4,313,448 A | 2/1982 | Stokes | |
| 4,316,469 A | 2/1982 | Kapitanov | |
| 4,317,451 A | 3/1982 | Cerwin et al. | |
| 4,372,293 A | 2/1983 | Vijil-Rosales | |
| 4,428,376 A | 1/1984 | Mericle | |
| 4,430,998 A | 2/1984 | Harvey | |
| 4,434,796 A | 3/1984 | Karapetian | |
| 4,449,298 A | 5/1984 | Patz | |
| 4,454,875 A | 6/1984 | Pratt et al. | |
| 4,467,805 A | 8/1984 | Fukuda | |
| 4,490,326 A | 12/1984 | Beroff et al. | |
| 4,492,075 A | 1/1985 | Faure | |
| 4,493,323 A | 1/1985 | Albright et al. | |
| 4,505,274 A | 3/1985 | Speelman | |
| 4,510,934 A | 4/1985 | Batra | |
| 4,531,522 A | 7/1985 | Bedi et al. | |
| 4,532,926 A | 8/1985 | O'Holla | |
| 4,535,772 A | 8/1985 | Sheehan | |
| 4,548,202 A | 10/1985 | Duncan | |
| 4,553,544 A | 11/1985 | Nomoto et al. | |
| 4,610,250 A | 9/1986 | Green | |
| 4,610,251 A | 9/1986 | Kumar | |
| 4,635,637 A | 1/1987 | Schreiber | |
| 4,637,380 A | 1/1987 | Orejola | |
| 4,653,486 A | 3/1987 | Coker | |
| 4,669,473 A | 6/1987 | Richards et al. | |
| 4,676,245 A | 6/1987 | Fukuda | |
| 4,689,882 A | 9/1987 | Lorenz | |
| 4,702,250 A | 10/1987 | Ovil et al. | |
| 4,712,553 A | 12/1987 | MacGregor | |
| 4,719,917 A | 1/1988 | Barrows | |
| 4,741,330 A | 5/1988 | Hayhurst | |
| 4,750,910 A | 6/1988 | Takayanagi et al. | |
| 4,776,337 A | 10/1988 | Palmaz | |
| 4,832,025 A | 5/1989 | Coates | |

(56) References Cited

U.S. PATENT DOCUMENTS

| | | |
|---|---|---|
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuck et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schultz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini et al. |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,102,418 A | 4/1992 | Granger et al. |
| 5,102,421 A | 4/1992 | Anpach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,147,382 A | 9/1992 | Gertzman et al. |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,391,173 A | 2/1995 | Wilk |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon et al. |
| 5,450,860 A | 9/1995 | O'Connor |
| 5,451,461 A | 9/1995 | Broyer |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,549,631 A | 8/1996 | Bonutti |
| 5,554,171 A | 9/1996 | Gatturna et al. |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,593,424 A | 1/1997 | Northrup, III et al. |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,654 A | 9/1997 | Thompson |
| 5,662,714 A | 9/1997 | Charvin et al. |
| 5,669,935 A | 9/1997 | Rosenman et al. |
| D386,583 S | 11/1997 | Ferragamo et al. |
| 5,676,675 A | 11/1997 | Grice |
| 5,683,417 A | 11/1997 | Cooper |
| D387,161 S | 12/1997 | Ferragamo et al. |
| 5,693,072 A | 12/1997 | McIntosh |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |

(56) References Cited

U.S. PATENT DOCUMENTS

| | | |
|---|---|---|
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |
| 5,765,560 A | 6/1998 | Verkerke et al. |
| 5,766,246 A | 6/1998 | Mulhauser et al. |
| 5,779,719 A | 7/1998 | Klein et al. |
| 5,782,864 A | 7/1998 | Lizardi |
| 5,807,403 A | 9/1998 | Beyar et al. |
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,887,594 A | 3/1999 | LoCicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,919,234 A | 7/1999 | Lemperle et al. |
| 5,925,078 A | 7/1999 | Anderson |
| 5,931,855 A | 8/1999 | Buncke |
| 5,938,668 A | 8/1999 | Scirica et al. |
| 5,941,899 A | 8/1999 | Granger et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 5,997,554 A | 12/1999 | Thompson |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 6,042,583 A | 3/2000 | Thompson et al. |
| 6,045,571 A | 4/2000 | Hill et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A | 12/2000 | Bonutti et al. |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Ledlein et al. |
| 6,858,222 B2 | 2/2005 | Nelson et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |

(56) References Cited

U.S. PATENT DOCUMENTS

| | | |
|---|---|---|
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,033,603 B2 | 4/2006 | Nelson et al. |
| 7,037,984 B2 | 5/2006 | Ledlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,063,716 B2 | 6/2006 | Cunningham |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,757 B2 | 12/2006 | Fallin et al. |
| 7,156,858 B2 | 1/2007 | Shuldt-Hempe et al. |
| 7,156,862 B2 | 1/2007 | Jacobs et al. |
| 7,160,312 B2 | 1/2007 | Saadat |
| 7,166,570 B2 | 1/2007 | Hunter et al. |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et al. |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,329,271 B2 | 2/2008 | Koyfman et al. |
| 7,371,253 B2 | 5/2008 | Leung et al. |
| 7,513,904 B2 | 4/2009 | Sulamanidze et al. |
| 7,514,095 B2 | 4/2009 | Nelson et al. |
| 7,582,105 B2 | 9/2009 | Kolster |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,871,425 B2 | 1/2011 | Jones et al. |
| 7,879,072 B2 | 2/2011 | Bonutti et al. |
| 7,913,365 B2 | 3/2011 | Genova et al. |
| 7,919,112 B2 | 4/2011 | Pathak et al. |
| 7,996,967 B2 | 8/2011 | Genova et al. |
| 8,011,072 B2 | 9/2011 | Genova et al. |
| 8,015,678 B2 | 9/2011 | Genova |
| 8,020,263 B2 | 9/2011 | Genova et al. |
| 8,028,387 B2 | 10/2011 | Genova et al. |
| 8,028,388 B2 | 10/2011 | Genova et al. |
| 8,032,996 B2 | 10/2011 | Trull et al. |
| 8,083,770 B2 | 12/2011 | Ruff et al. |
| 8,100,940 B2 | 1/2012 | Leung et al. |
| 8,118,834 B1 * | 2/2012 | Goraltchouk .... A61B 17/06166 606/228 |
| 8,216,273 B1 | 7/2012 | Goraltchouk et al. |
| 8,225,673 B2 | 7/2012 | D'Agostino |
| 8,226,684 B2 | 7/2012 | Nawrocki et al. |
| 8,246,652 B2 | 8/2012 | Ruff |
| 8,308,761 B2 | 11/2012 | Brailovski et al. |
| 8,460,338 B2 | 6/2013 | Goraltchouk et al. |
| 8,615,856 B1 | 12/2013 | Gelbart |
| 8,641,732 B1 | 2/2014 | Goraltchouk et al. |
| 8,652,170 B2 | 2/2014 | Leung et al. |
| 8,795,332 B2 | 8/2014 | Leung et al. |
| 8,915,943 B2 * | 12/2014 | Hunter ............ A61B 17/06166 606/228 |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0038848 A1 | 11/2001 | Donda et al. |
| 2001/0039450 A1 | 11/2001 | Pavcnik et al. |
| 2001/0051807 A1 | 12/2001 | Grafton |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0077448 A1 | 6/2002 | Antal et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0165555 A1 | 11/2002 | Stein et al. |
| 2002/0173822 A1 | 11/2002 | Justin et al. |
| 2002/0179718 A1 | 12/2002 | Murokh et al. |
| 2002/0198544 A1 | 12/2002 | Uflacker |
| 2003/0040795 A1 | 2/2003 | Elson et al. |
| 2003/0069602 A1 | 4/2003 | Jacobs et al. |
| 2003/0088270 A1 | 5/2003 | Lubbers et al. |
| 2003/0149447 A1 | 8/2003 | Morency |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |

(56) References Cited

U.S. PATENT DOCUMENTS

| | | |
|---|---|---|
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0230223 A1 | 11/2004 | Bonutti et al. |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 6/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0267531 A1 | 12/2005 | Ruff et al. |
| 2005/0267532 A1 | 12/2005 | Wu |
| 2005/0276841 A1* | 12/2005 | Davis ............... A61K 9/0051 424/443 |
| 2005/0277984 A1 | 12/2005 | Long |
| 2005/0283246 A1 | 12/2005 | Cauthen, III et al. |
| 2006/0020272 A1 | 1/2006 | Gildenberg |
| 2006/0030884 A1 | 2/2006 | Young et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0122608 A1 | 6/2006 | Fallin et al. |
| 2006/0135994 A1 | 6/2006 | Ruff |
| 2006/0135995 A1 | 6/2006 | Ruff |
| 2006/0140999 A1 | 6/2006 | Lendlein et al. |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Ledlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0016251 A1 | 1/2007 | Roby |
| 2007/0021779 A1 | 1/2007 | Garvin et al. |
| 2007/0027475 A1 | 2/2007 | Pagedas |
| 2007/0038249 A1* | 2/2007 | Kolster ............... A61B 17/06 606/228 |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0185494 A1 | 8/2007 | Reese |
| 2007/0208355 A1 | 9/2007 | Ruff |
| 2007/0213770 A1 | 9/2007 | Dreyfuss |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0225764 A1 | 9/2007 | Benavitz et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0243228 A1* | 10/2007 | McKay .................. 424/426 |
| 2007/0257395 A1 | 11/2007 | Lindh et al. |
| 2007/0282247 A1 | 12/2007 | Desai et al. |
| 2007/0293892 A1 | 12/2007 | Takasu |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0131692 A1 | 6/2008 | Rolland et al. |
| 2008/0132943 A1 | 6/2008 | Maiorino et al. |
| 2008/0169059 A1 | 7/2008 | Messersmith et al. |
| 2008/0195147 A1 | 8/2008 | Stopek |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0248216 A1 | 10/2008 | Yeung et al. |
| 2008/0255611 A1 | 10/2008 | Hunter |
| 2008/0255612 A1 | 10/2008 | Hunter |
| 2008/0262542 A1 | 10/2008 | Sulamanidze et al. |

(56) References Cited

U.S. PATENT DOCUMENTS

| | | |
|---|---|---|
| 2008/0281338 A1 | 11/2008 | Wohlert et al. |
| 2008/0281355 A1* | 11/2008 | Mayer et al. .............. 606/228 |
| 2008/0281357 A1 | 11/2008 | Sung et al. |
| 2008/0312688 A1 | 12/2008 | Naworocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |
| 2009/0105753 A1 | 4/2009 | Greenhalgh et al. |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0216253 A1 | 8/2009 | Bell et al. |
| 2009/0226500 A1 | 9/2009 | Avelar et al. |
| 2009/0228021 A1 | 9/2009 | Leung |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250588 A1 | 10/2009 | Robeson et al. |
| 2009/0259233 A1 | 10/2009 | Bogart et al. |
| 2009/0259251 A1 | 10/2009 | Cohen |
| 2009/0287245 A1* | 11/2009 | Ostrovsky ........ A61B 17/06166 606/228 |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |
| 2009/0318958 A1 | 12/2009 | Ochiai |
| 2010/0021516 A1* | 1/2010 | McKay ................. A61K 9/0024 424/422 |
| 2010/0023055 A1 | 1/2010 | Rousseau |
| 2010/0030261 A1* | 2/2010 | McClain ...................... 606/230 |
| 2010/0057123 A1 | 3/2010 | D'Agostino et al. |
| 2010/0063540 A1 | 3/2010 | Maiorino |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0160961 A1* | 6/2010 | Nawrocki ........ A61B 17/06166 606/228 |
| 2010/0163056 A1 | 7/2010 | Tschopp et al. |
| 2010/0198257 A1* | 8/2010 | Stopek ............. A61B 17/06166 606/228 |
| 2010/0211097 A1 | 8/2010 | Hadba et al. |
| 2010/0211098 A1 | 8/2010 | Hadba et al. |
| 2010/0230300 A1 | 9/2010 | Hunter et al. |
| 2010/0239635 A1 | 9/2010 | McClain et al. |
| 2010/0292718 A1 | 11/2010 | Sholev et al. |
| 2010/0298637 A1 | 11/2010 | Ruff |
| 2010/0298639 A1 | 11/2010 | Leung et al. |
| 2010/0298848 A1 | 11/2010 | Leung et al. |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298874 A1 | 11/2010 | Leung et al. |
| 2010/0298875 A1 | 11/2010 | Leung et al. |
| 2010/0298876 A1 | 11/2010 | Leung et al. |
| 2010/0298879 A1 | 11/2010 | Leung et al. |
| 2010/0298880 A1 | 11/2010 | Leung et al. |
| 2010/0313729 A1 | 12/2010 | Genova et al. |
| 2010/0318122 A1 | 12/2010 | Leung et al. |
| 2010/0318123 A1 | 12/2010 | Leung et al. |
| 2010/0318124 A1 | 12/2010 | Leung et al. |
| 2011/0009902 A1 | 1/2011 | Leung et al. |
| 2011/0022086 A1 | 1/2011 | D'Agostino et al. |
| 2011/0046668 A1 | 2/2011 | Goraltchouk et al. |
| 2011/0046669 A1 | 2/2011 | Goraltchouk et al. |
| 2011/0093010 A1 | 4/2011 | Genova et al. |
| 2011/0106152 A1 | 5/2011 | Kozlowski |
| 2011/0125188 A1* | 5/2011 | Goraltchouk ......... D06M 15/00 606/228 |
| 2011/0130774 A1 | 6/2011 | Criscuolo et al. |
| 2011/0166597 A1 | 7/2011 | Herrmann et al. |
| 2011/0264138 A1 | 10/2011 | Avelar et al. |
| 2011/0288583 A1 | 11/2011 | Goraltchouk et al. |
| 2011/0319932 A1 | 12/2011 | Avelar et al. |
| 2012/0101522 A1 | 4/2012 | Megaro et al. |
| 2012/0109188 A1 | 5/2012 | Viola |
| 2012/0245659 A1 | 9/2012 | Matthews |
| 2013/0072971 A1 | 3/2013 | Kim et al. |
| 2013/0103078 A1 | 4/2013 | Longo et al. |
| 2013/0165971 A1 | 6/2013 | Leung et al. |
| 2013/0172931 A1 | 7/2013 | Gross et al. |
| 2013/0180966 A1 | 7/2013 | Gross et al. |
| 2013/0204295 A1 | 8/2013 | Hunter et al. |
| 2013/0226233 A1 | 8/2013 | D'Agostino et al. |
| 2013/0226234 A1 | 8/2013 | Avelar et al. |
| 2013/0238021 A1 | 9/2013 | Gross et al. |
| 2013/0238022 A1 | 9/2013 | Gross et al. |
| 2013/0245684 A1 | 9/2013 | Ruff et al. |
| 2013/0317545 A1 | 11/2013 | Gross et al. |
| 2014/0039527 A1 | 2/2014 | Avelar et al. |

FOREIGN PATENT DOCUMENTS

| | | |
|---|---|---|
| CA | 2309844 | 12/1996 |
| CN | 2640420 | 9/2004 |
| DE | 01810800 | 6/1970 |
| DE | 03227984 | 2/1984 |
| DE | 04302895 | 8/1994 |
| DE | 19618891 | 4/1997 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0513713 | 5/1992 |
| EP | 0428253 | 7/1994 |
| EP | 0632999 | 1/1995 |
| EP | 0513736 | 2/1995 |
| EP | 0464479 | 3/1995 |
| EP | 0464480 | 3/1995 |
| EP | 0576337 A1 | 3/1997 |
| EP | 0576337 B1 | 3/1997 |
| EP | 0574707 | 8/1997 |
| EP | 0612504 | 11/1997 |
| EP | 0558993 | 4/1998 |
| EP | 0913123 | 5/1999 |
| EP | 0916310 | 5/1999 |
| EP | 0664198 | 6/1999 |
| EP | 0960600 | 12/1999 |
| EP | 0705567 | 3/2002 |
| EP | 0673624 | 8/2002 |
| EP | 0839499 | 9/2003 |
| EP | 0755656 | 12/2003 |
| EP | 1075843 | 2/2005 |
| EP | 1525851 | 4/2005 |
| EP | 1532942 | 5/2005 |
| EP | 0826337 | 12/2005 |
| EP | 0991359 | 11/2007 |
| EP | 1897500 A1 | 3/2008 |
| EP | 2036502 | 3/2009 |
| EP | 1948261 | 11/2010 |
| EP | 1726317 | 7/2012 |
| FR | 2619129 | 2/1989 |
| FR | 2693108 | 1/1994 |
| GB | 0267007 | 3/1927 |
| GB | 1091282 | 11/1967 |
| GB | 1428560 | 7/1973 |
| GB | 1506362 | 4/1978 |
| GB | 1508627 | 4/1978 |
| JP | S47-044390 A | 11/1972 |
| JP | 1506362 | 4/1978 |
| JP | 54-116419 | 9/1979 |
| JP | 63-288146 | 11/1988 |
| JP | 001113091 | 5/1989 |
| JP | H03-080868 A | 4/1991 |
| JP | 3-165751 | 7/1991 |
| JP | 4-096758 | 3/1992 |
| JP | 4-266749 | 9/1992 |

(56) References Cited

FOREIGN PATENT DOCUMENTS

| | | |
|---|---|---|
| JP | 9-103477 | 4/1997 |
| JP | 410085225 | 4/1998 |
| JP | 11-313826 | 11/1999 |
| JP | 011332828 | 12/1999 |
| JP | 2002-059235 | 2/2002 |
| JP | 2003-275217 | 9/2003 |
| JP | 2007-502281 A | 2/2007 |
| JP | 2007-515212 A | 6/2007 |
| JP | 2008-062061 A | 3/2008 |
| JP | 2008-142536 A | 6/2008 |
| JP | 2008-194462 A | 8/2008 |
| JP | 2009-066421 | 4/2009 |
| JP | 2009-118967 | 6/2009 |
| JP | 2010-523288 A | 7/2010 |
| KR | 10-2015-0072908 A | 7/2005 |
| KR | 6013299 | 2/2006 |
| NZ | 501224 | 3/2002 |
| NZ | 531262 | 12/2005 |
| RU | 2139690 | 10/1999 |
| RU | 2175855 | 11/2001 |
| RU | 2241389 | 12/2004 |
| RU | 2268752 | 1/2006 |
| SU | 1745214 | 7/1992 |
| SU | 1752358 | 8/1992 |
| WO | WO 1996/006565 | 3/1966 |
| WO | WO 1986/000020 | 1/1986 |
| WO | WO 1987/001270 | 3/1987 |
| WO | WO 1988/009157 | 12/1988 |
| WO | WO 1989/005618 | 6/1989 |
| WO | WO 1990/009149 | 8/1990 |
| WO | WO 1990/014795 | 12/1990 |
| WO | WO 1991/007916 A1 | 6/1991 |
| WO | WO 1992/022336 | 12/1992 |
| WO | WO 1995/016399 | 6/1995 |
| WO | WO 1995/029637 | 11/1995 |
| WO | WO 1997/000047 | 1/1997 |
| WO | WO 1998/052473 | 11/1998 |
| WO | WO 1998/055031 | 12/1998 |
| WO | WO 1999/021488 | 5/1999 |
| WO | WO 1999/033401 | 7/1999 |
| WO | WO 1999/052478 | 10/1999 |
| WO | WO 1999/059477 | 11/1999 |
| WO | WO 1999/062431 | 12/1999 |
| WO | WO 2000/051658 | 9/2000 |
| WO | WO 2000/051685 | 9/2000 |
| WO | WO 2001/006952 | 2/2001 |
| WO | WO 2001/056626 | 8/2001 |
| WO | WO 2003/001979 | 1/2003 |
| WO | WO 2003/003925 | 1/2003 |
| WO | WO 2003/017850 A2 | 3/2003 |
| WO | WO 2003/045255 | 6/2003 |
| WO | WO 2003/077772 | 9/2003 |
| WO | WO 2003/092758 | 11/2003 |
| WO | WO 2003/103733 | 12/2003 |
| WO | WO 2003/103972 | 12/2003 |
| WO | WO 2003/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/096955 | 10/2005 |
| WO | WO 2005/096956 | 10/2005 |
| WO | WO 2005/112787 | 12/2005 |
| WO | WO 2006/005144 | 1/2006 |
| WO | WO 2006/012128 | 2/2006 |
| WO | WO 2006/037399 | 4/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005296 | 1/2007 |
| WO | WO 2007/038837 | 4/2007 |
| WO | WO 2007/053812 | 5/2007 |
| WO | WO 2007/089864 | 8/2007 |
| WO | WO 2007/089878 A1 | 8/2007 |
| WO | WO 2007/112024 | 10/2007 |
| WO | WO 2007/133103 | 11/2007 |
| WO | WO 2007/145614 | 12/2007 |
| WO | WO 2008/128113 | 10/2008 |
| WO | WO 2009/042841 | 4/2009 |
| WO | WO 2009/068252 | 6/2009 |
| WO | WO 2009/087105 | 7/2009 |
| WO | WO 2009/097556 | 8/2009 |
| WO | WO-2009129251 A2 * | 10/2009 ....... A61B 17/06166 |
| WO | WO-2009132284 A2 * | 10/2009 ....... A61B 17/06166 |
| WO | WO 2009/151876 | 12/2009 |
| WO | WO 2010/008815 A1 | 2/2010 |
| WO | WO 2010/052007 | 5/2010 |
| WO | WO 2011/053375 | 5/2011 |
| WO | WO 2011/060446 A2 | 5/2011 |
| WO | WO 2011/090628 | 7/2011 |
| WO | WO 2011/139916 | 11/2011 |
| WO | WO 2011/140283 | 11/2011 |
| WO | WO 2011/140400 A2 | 11/2011 |

OTHER PUBLICATIONS

Bacci, Pier Antonio, "Chirurgia Estetica Mini Invasiva Con Fili Di Sostegno", Collana di Arti, Pensiero e Scienza; Minelli Editore—2006; 54 pgs.

Behl, Marc et al., "Shape-Memory Polymers", Materials Today Apr. 2007; 10(4); 20-28.

Belkas, J. S. et al., "Peripheral nerve regeneration through a synthetic hydrogel nerve tube", Restorative Neurology and Neuroscience 23 (2005) 19-29.

Bellin, I. et al., "Polymeric triple-shape materials", Proceedings of the National Academy of Sciences of the United States of America Nov. 28, 2006; 2103(48):18043-18047.

Boenisch, U.W. et al 'Pull-Out strength and stiffness of meniscal repair using absorbable arrows or Ti-Cron vertical and horizontal loop sutures' American Journal of Sports Medicine, Sep.-Oct. 1999 vol. 27, Issue 5, pp. 626-631.

Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.

Buncke, Jr., H.J. et al 'The Suture Repair of One-Millimeter Vessels, microvascular surgery' (1966) Report of First Conference; Oct. 6-7 pp. 24-35.

Bunnell, S. 'Gig pull-out suture for tendons' J Bone Joint Surg. Am (1954) vol. 36A, No. 4 pp. 850-851.

CCPR Centro De Cirurgia Plastica e Reabilitacao Up Lifting (Aptos Threads) http:/ /ccpr.com.br/upl-l.htm, Aug. 19, 2002 pp. 1-2.

Dahlin, Lars, "Techniques of Peripheral Nerve Repair", Scandinavian Journal of Surgery 97: 310-316, 2008.

Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.

Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.

Datillo, Jr., P. et al 'Tissue holding performance of knotless absorbable sutures' Society for Biomaterials 29th Annual Meeting Transactions (2003) p. 101.

Declaration of Dr. Gregory L. Ruff, dated Aug. 19, 2005, 8 pages, with Exhibits A-E.

De Persia, Raúl et al., "Mechanics of Biomaterials: Sutures After the Surgery", Applications of Engineering Mechanics in Medicine, GED-University of Puerto Rico, Mayaguez May 2005, p. F1-F27.

(56) References Cited

OTHER PUBLICATIONS

Delorenzi, C.L., "Barbed Sutures: Rationale and Technique", Aesthetic Surg. J. Mar. 26, 2006(2): 223-229.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb. 27, 2006(2): 2 pages.
Gross, R.A. et al 'Biodegradable Polymers for the Environment' Science (2002) vol. 297, Issue 5582 pp. 803.
Han, H. et al 'Mating and Piercing Micromechanical Suture for Surface Bonding Applications' (1991) Proceedings of the 1991 Micro Electro Mechanical Systems (MEMS>91), An Investigation of Micro Structures, Sensors, Actuators, Machines and Robots pp. 253-258.
Ingle, N.P. et al 'Barbed Suture Anchoring Strength: Applicability to Dissimilar Polymeric Materials' College of Textiles, North Carolina State University, 7th World Biomaterials Congress 2004, 1 page.
Ingle, N.P. et al 'Mechanical Performance and Finite Element Analysis of Bi-directional Barbed Sutures' Master of Science in Textile Technology & Management at North Carolina State University Aug. 2003, 126 pages.
Ingle, N.P. et al., "Optimizing the tissue anchoring performance of barbed sutures in skin and tendon tissues", Journal of Biomechanics 43 (2010); pp. 302-309.
Ingle, Nilesh P et al., "Testing the Tissue-holding Capacity of Barbed Sutures", College of Textiles, North Carolina State University, Fiber Science, The Next Generation Oct. 17-19, 2005, New Jersey Institute of Technology, Newark, NJ, 4 pages.
Jennings et al 'A New Technique in primary tendon repair' Surg. Gynecol. Obstet. (1952) vol. 95, No. 5 pp. 597-600.
Jeong, H.E. et al 'A nontransferring dry adhesive with hierarchial polymer nanohairs' PNAS 106 (14) pp. 5639-5644 (2009).
Kaminer, M. et al., "ContourLift™: A New Method of Minimally Invasive Facial Rejuvenation", Cosmetic Dermatology Jan. 2007; 20(1): 29-35.
Kelch et al., "Shape-memory Polymer Networks from Olio[(ϵ-hydroxycaproate)-co-glycolate]dimethacrylates and Butyl Acrylate with Adjustable Hydrolytic Degradation Rate", Biomacromolecules 2007;8(3):1018-1027.
Khademhosseini, Ali et al., "Nanobiotechnology Drug Delivery and Tissue Engineering", Chemical Engineering Progress 102:38-42 (2006).
Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.
Lendlein, A. et al 'Biodegradable, Elastic Shape-Memory Polymers for Potential Biomedical Applications' (2002) Science vol. 296 pp. 1673-1676.
Lendlein, A. et al 'Shape-Memory Polymers' Agnew Chem. Int. Ed. (2002) vol. 41 pp. 2034-2057.
Leung, J. et al 'Barbed, Bi-directional Medical Sutures: Biomechanical Properties and Wound Closure Efficacy Study' 2002 Society for Biomaterials 28th Annual Meeting Transactions 1 page.
Leung, J. et al 'Barbed, Bi-directional Surgical Sutures' International Conference & Exhibition on Healthcare & Medical Textiles, Jul. 8-9, 2003 pp. 1-8.
Leung, J. et al 'Barbed, Bi-directional Surgical Sutures: In Vivo Strength and Histopathology Evaluations' 2003 Society for Biomaterials 29th Annual Meeting Transactions pp. 100.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.
Leung, J. et al 'Performance Enhancement of a Knotless Suture via Barb Geometry Modifications' 7th World Biomaterials Congress 2004, 1 page.
Li, Y.Y. et al 'Polymer Replicas of Photonic Porous Silicon for Sensing and Drug Delivery Applications' (2003) Science vol. 299 pp. 2045-2047.
Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.
Madduri, Srinivas, et al., "Neurotrophic factors release from nerve conduits for peripheral axonal regeneration", European Cells and Materials vol. 16; Suppl. 1 (2008), p. 14.
Madhave et al 'A biodegradable and biocompatible gecko-inspired tissue adhesive' PNAS 105(7) pp. 2307-2312 (2008).
Maitland et al., "Prototype laser-activated shape memory polymer foam device for embolic treatment of aneurysms", Journal of Biomedical Optics 2007 May/Jun.;12(3): pp. 030504-1 to 030504-3.
Malina, M. et al 'Endovascular AAA Exclusion: Will Stents with Hooks and Barbs Prevent Stent-Graft Migration' Journal Endovascular Surgery (1998) vol. 5 pp. 310-317.
Mansberger et al 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.
Martin, D.P. et al 'Medical applications of poly-4-hydroxybutyrate: a strong flexible absorbable biomaterial' Biochemical Engineering Journal vol. 16 (2003) pp. 97-105.
Mason, M.L. 'Primary and Secondary Tendon Suture. A discussion of the significance of technique in tendon surgery' (1940) Surg Gynecol Obstet 70.
McKee, GK 'Metal anastomosis tubes in tendon suture' The Lancet (1945) pp. 659-660.
McKenzie 'An Experimental Multiple Barbed Suture for the Long Flexor Tendons of the Palm and Fingers' The Journal of Bone and Joint Surgery (1967) vol. 49B, No. 3 pp. 440-447.
Middleton and Tipton 'Synthetic Biodegradable Polymers as Medical Devices' (1998) Medical Plastics and Biomaterials Magazine, 9 pages.
Moran et al., "Bidirectional-Barbed Sutured Knotless Running Anastomosis v Classic van Velthovan in a Model System", Journal of Endourology Oct. 2007; 21(10); 1175-1177.
Mullner, "Metal Foam Has a Good Memory", Dec. 18, 2007 Original story at <http://www.physorg.com/news117214996.html>.
Murtha et al., "Evaluation of a Novel Technique for Wound Closure Using A Barbed Suture", Journal of the American Society of Plastic Surgeons 2006; 117(6); 1769-1780.
Nie, Zhihong and Kumacheva, Eugenia, "Patterning surfaces with functional polymers", Nature Materials vol. 7(2008): 277-290.
Paul, Malcolm D., "Bidirectional Barbed Sutures for Wound Closure: Evolution and Applications", Journal of the American College of Certified Wound Specialists (2009) 1, 51-57.
Paul, Malcolm D. and Rui Avelar, "Quill™ SRS Techniques & Procedures A Novel Approach to Soft Tissue Approximation", Canada, Angiotech Pharmaceuticals, Inc., First Edition Aug. 2007: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Second Edition Aug. 2008: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Third Edition 2009, 8 2007-2009: 27 pages.
Paul, Malcolm D. and Rui Avelar, "Quill™ SRS Techniques & Procedures A Novel Approach to Soft Tissue Approximation", Canada, Angiotech Pharmaceuticals, Inc., Fourth Edition 2010, 8 2007-2010: 27 pages.
Paul, Malcolm D., "Using Barbed Sutures in Open/Subperiosteal Midface Lifting", Aesthetic Surgery Journal 2006(26): 725-732.

(56) References Cited

OTHER PUBLICATIONS

Potenza, A. 'Tendon Healing Within the Flexor Digital Sheath in the Dog: An Experimental Study' Journal of Bone & Joint Surgery (1962) vol. 44A No. 1 pp. 49-64.
Pulvertaft 'Suture Materials and Tendon Junctures' American Journal of Surgery (1965) vol. 109 pp. 346-352.
Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.
Quill Medical, Inc. 'Quill Medical's Novel-Self-Anchoring Surgical Suture Approved For Sale in Europe' Press Release; Research Triangle Park, N.C. May 10, 2004, 1 page.
Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.
Richert, Ludovic, et al., "Surface Nanopatterning to Control Cell Growth", Advanced Materials 2008(15): 1-5.
Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2005, 2 pages.
Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherman, Peter et al., "Sutures as longitudinal guides for the repair of nerve defects-Influence of suture numbers and reconstruction of nerve bifurcations", Restorative Neurology and Neuroscience 23 (2005) 79-85.
Schmid A. et al 'The outspreading anchor cord. A material for arthroscopic suturing of a fresh anterior cruciate ligament rupture' Surgical Clinic of the University of Gottingen' (1987) pp. 417-426.
Semenov, G.M. et al 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, M. et al., "APTOS Suture Lifting Methods: 10 Years of Experience", Clin Plastic Surg 36 (2009); pp. 281-306.
Sulamanidze, M.A. et al 'Clinical aspects of bloodless facelift using APTOS filaments' A.V. Vishnevsky Institute of Surgery, Bol'shaya Serpukhovskaya ul, 7, 113811, Moscow, Russia (2002) pp. 24-34.
Sulamanidze, M.A. et al 'Facial lifting with Aptos threads' International Journal of Cosmetic Surgery and Aesthetic Dermatology' (2001) No. 4 pp. 1-8.
Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al 'Morphological foundations of facelift using APTOS filaments' Bolshaya Serpukhovskaya ul 27, 113811 Moscow, Russia (2002) pp. 19-26.
Sulamanidze, M.A. et al 'Removal of Facial Soft Tissue Ptosis with Special Threads' Dermatol Surg (2002) vol. 28 pp. 367-371.
Sulamanidze, MD, M.A., et al., "Soft tissue lifting in the mid-face: old philosophy, new approach—internal stitching technique (APTOS Needle)", Plastic and Aesthetic Surgery Clinic Total Sharm, Moscow, Russia, (2005):15-29.
Sulzle, Inc. B.G. et al Drilled End Surgical Needles Jul. 2002 Syracuse, New York.
Surgical Specialties Corporation, "Wound Closure Catalog"; Summer 2005, 5 pages.
Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.
Verdan, C. 'Primary Repair of Flexor Tendons' Journal of Bone and Joint Surgery (1960) vol. 42, No. 4 pp. 647-657.

Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
Communication from EPO re: 10000486 dated Apr. 4, 2011, 4 pages.
European Search Report re: EP05025816 dated Jun. 23, 2006.
European Search Report for EP07006258.3 dated May 4, 2007, 4 pages.
European Search Report for EP07015905.8 dated Oct. 2, 2007, 2 pages.
European Search Report for EP07015906 dated Oct. 2, 2007.
European Search Report for EP07016222 dated Jan. 7, 2008.
European Search Report for EP09014651 dated Jan. 12, 2010.
European Search Report for EP10000629.5 dated Mar. 10, 2010, 4 pages.
European Search Report re: EP10000486 dated Apr. 23, 2010.
European Search Report re: 10004453 dated Jun. 15, 2010.
European Search Report for EP10011868.6 dated Dec. 6, 2010, 2 pages.
European Search Report for EP10011869 dated Jan. 20, 2011.
European Search Report for EP10011871.0 dated Dec. 3, 2010, 2 pages.
European Search Report for EP10011872 dated Apr. 20, 2011.
European Search Report for EP10012437 dated Apr. 28, 2011.
European Search Report for EP10186592.1 dated Jan. 19, 2011, 2 pages.
European Search Report for EP10184766 dated Apr. 20, 2011.
Extended European Search Report re: 07015905.8 dated Oct. 23, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2007/002688 dated Aug. 14, 2008.
International Preliminary Report re: PCT/US2008/060127 dated Oct. 13, 2009.
International Preliminary Report on Patentability re: PCT/US2008/064921 dated Dec. 1, 2009.
International Preliminary Report on Patentability re: PCT/US2008/0075849 dated Mar. 16, 2010.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/034703 dated Aug. 24, 2010.
International Preliminary Report re: PCT/US2009/040545 dated Oct. 19, 2010.
International Preliminary Report re: PCT/US2009/041685 dated Oct. 26, 2010.
International Preliminary Report re: PCT/US2011/035431 dated Nov. 6, 2012.
International Preliminary Report on Patentability re: PCT/US2011/040014 dated Dec. 14, 2012.
International Preliminary Report re: PCT/US2011/059238 dated May 7, 2013.
International Search Report for PCT/US1994/09631 dated Dec. 9, 1994.
International Search Report for PCT/US1998/10478 dated Sep. 23, 1998.
International Search Report for PCT/US2002/027525 dated Dec. 9, 2002, 3 pages.
International Search Report for PCT/US2003/030664 dated May 25, 2004.
International Search Report for PCT/2003/030666 dated Dec. 15, 2004.

(56) References Cited

OTHER PUBLICATIONS

International Search Report for PCT/US2003/025088 dated Dec. 29, 2003.
International Search Report re: PCT/US2003/030674 dated Sep. 2, 2004.
International Search Report re: PCT/US2004/014962 dated Feb. 24, 2005.
International Search Report for PCT/US2007/002688 dated Oct. 22, 2007.
International Search Report for PCT/US2007/074658 dated Jun. 12, 2007, 3 pages.
International Search Report for PCT/US2008/060127 dated Sep. 23, 2008, 5 pages.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/040545 dated Oct. 29, 2009.
International Search Report for PCT/US2009/041685 dated Dec. 22, 2009.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report for PCT/US2011/059238 dated May 21, 2012.
Partial European Search Report re: EP05025816 dated Mar. 20, 2006.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
Supplementary European Search Report re: EP98923664 dated Jun. 12, 2001.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: EP03785177 dated May 19, 2009.
Supplementary European Search Report re: 07017663 dated Nov. 7, 2007.
Croce, MD, E., et al., "Intracorporeal Knot-Tying and Suturing Techniques in Laparoscopic Surgery: Technical Details," JSLS, 2000, 4:17-22, 6 pgs.
Australian Office Action, Patent Examination Report No. 1, dated Sep. 19, 2013 for Application No. AU 2012201433, 5 pgs.
Australian Office Action, Patent Examination Report No. 2, dated Oct. 14, 2014 for Application No. AU 2012201433, 8 pgs.
European Search Report and Written Opinion dated Jan. 25, 2018 for Application No. EP 17178134.7, 9 pgs.
European Examination Report dated May 6, 2011 for Application No. EP 05750101.7, 5 pgs.

European Decision Rejecting Opposition and Minutes of Oral Proceedings held Nov. 16, 2015 for Application No. EP 05750101.7 and Patent No. EP 1761176, dated Dec. 10, 2015, 18 pgs.
European Notice of Appeal of Opposition Decision filed Feb. 17, 2016 for Application No. EP 05750101.7 and Patent No. EP 1761176, 4 pgs.
European Statement of Grounds of Appeal and Declaration of Tim Kosa dated Apr. 26, 2016 for Application No. EP 05750101.7 and Patent No. EP 1761176, 22 pgs.
European Reply to Notice of Appeal dated Sep. 6, 2016 for Application No. EP 05750101.7 and Patent No. EP 1761176, 18 pgs.
European Search Report and Written Opinion dated Mar. 20, 2014 for Application No. EP 13168117.3, 9 pgs.
European Examination Report dated Mar. 17, 2016 for Application No. EP 13168117.3, 3 pgs.
European Examination Report dated Mar. 11, 2016 for Application No. EP 13168122.3, 4 pgs.
International Preliminary Report on Patentability dated Feb. 10, 2009 for Application No. PCT/US2005/017028, 4 pgs.
Japanese Office Action, Notification of Reasons for Refusal, dated Oct. 4, 2010 for Application No. JP 2007-513452, 6 pgs.
Japanese Office Action, Decision of Refusal, dated Jun. 7, 2011 for Applicaton No. JP 2007-513452, 4 pgs.
Japanese Office Action, Report of Reconsideration by Examiner before Appeal, dated Nov. 15, 2011 for Application No. JP 2007-513452, 4 pgs.
Japanese Office Action, Notification of Reasons for Refusal, dated Apr. 9, 2013 for Application No. JP 2011-223686, 6 pgs.
Japanese Office Action, Decision of Refusal, dated Nov. 20, 2013 for Application No. JP 2011-223686, 4 pgs.
Japanese Office Action, Appeal Decision, dated May 7, 2014 for Application No. JP 2011-223686, 4 pgs.
Korean Office Action dated Jan. 20, 2012 for Application No. 10-2006-7023828, 9 pgs.
Australian Office Action dated Jun. 18, 2015 for Application No. 2011323299, 4 pages.
Australian Office Action dated Jun. 6, 2016 for Application No. 2011323299, 4 pages.
Canadian Office Action dated Aug. 25, 2017 for Application No. 2,816,326, 4 pages.
Canadian Office Action dated Jul. 30, 2018 for Application No. 2,816,326, 4 pages.
Chinese Office Action dated Aug. 15, 2015 for Application No. 201180063975.3, 12 pages.
European Examination Report dated Feb. 12, 2015 for Application No. 11838842.0, 8 pages.
European Examination Report dated Apr. 10, 2018 for Application No. 11838842.0, 5 pages.
European Examination Report dated Mar. 8, 2019 for Application No. 11838842.0, 5 pages.
Japanese Office Action dated Aug. 25, 2015 for Application No. 2013-537843, 13 pages.
Japanese Office Acton dated Mar. 7, 2017 for Application No. 2016-117827, 10 pages.
Korean Office Action dated Sep. 19, 2017 for Application No. 10-2013-7014209, 11 pages.
Korean Office Action dated May 29, 2018 for Application No. 10-2013-7014209, 7 pages.
Korean Office Action dated Jul. 30, 2018 for Application No. 10-2013-7014209, 8 pages.
Mexican Office Action dated May 14, 2018 for Application No. MX/a/2013/005072, 5 pages.
New Zealand Office Action dated Jan. 15, 2014 for Application No. 610341, 3 pages.
Russian Office Action dated Sep. 18, 2015 for Application No. 2013125475, 5 pages.
Brazilian Search Report dated Sep. 9, 2019 for Application No. BR 112013011090-2, 4 pgs.
Chinese Search Report, First, dated Aug. 15, 2015 for Application No. CN 201180063975.3, 2 pgs.
Indian Office Action dated Jul. 25, 2019 for Application No. 3929/DELNP/2013, 6 pgs.

(56) References Cited

OTHER PUBLICATIONS

Japanese Office Action, Examiner's Decision of Refusal, dated Aug. 15, 2017 for Application No. JP 2016-117827, 4 pgs.

* cited by examiner

FIG. 1A
FIG. 1B
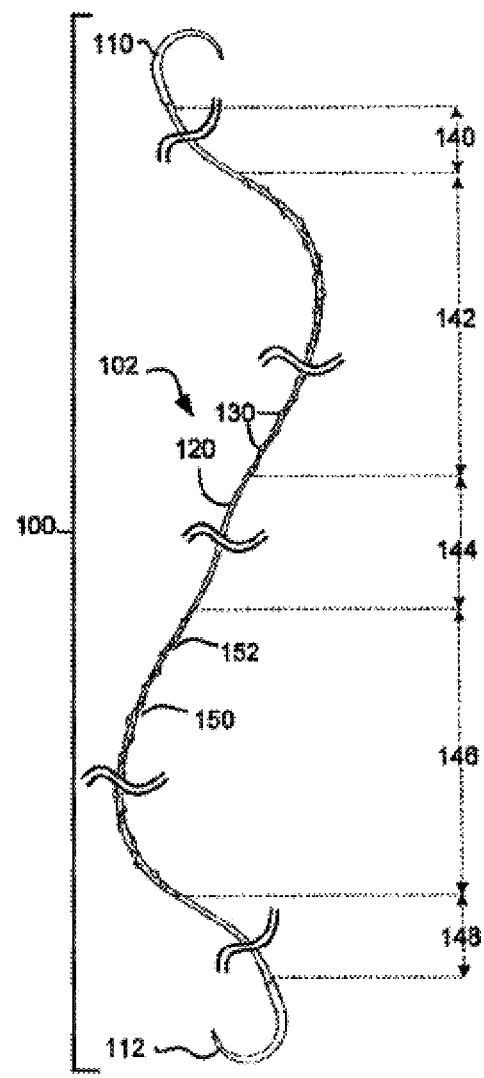
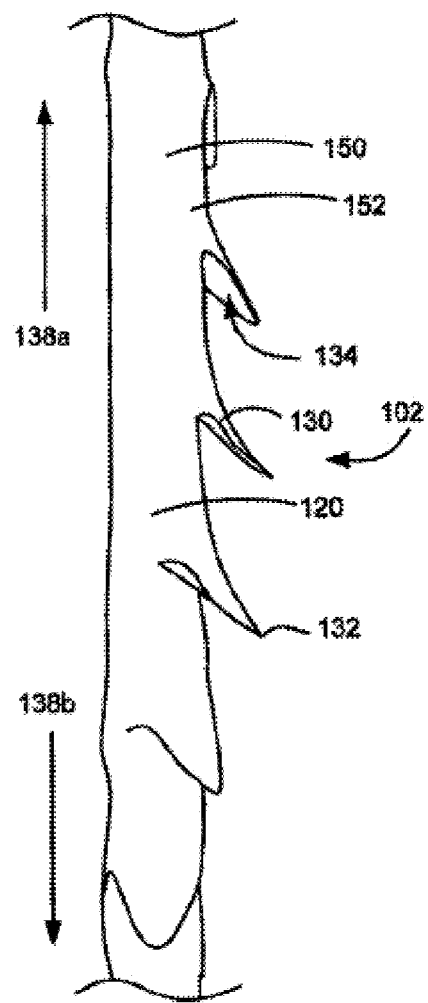

FIG. 6G

Table 1. Synthetic Suture

| USP Size Min. | Metric Size (Gauge No.) Max. | Limit on Average Diameter (mm) Min. | Limit on Average Diameter (mm) Max. | Knot-Pull Tensile Strength (in kgf) (except where otherwise specified)* Limit on Average Min. | Knot-Pull Tensile Strength (in N) (except where otherwise specified)* |
|---|---|---|---|---|---|
| 12-0 | 0.01 | 0.001 | 0.009 | -- | -- |
| 11-0 | 0.1 | 0.010 | 0.019 | -- | -- |
| 10-0 | 0.2 | 0.020 | 0.029 | 0.025* | 0.24* |
| 9-0 | 0.3 | 0.030 | 0.039 | 0.050* | 0.49* |
| 8-0 | 0.4 | 0.040 | 0.049 | 0.07 | 0.69 |
| 7-0 | 0.5 | 0.050 | 0.069 | 0.14 | 1.37 |
| 6-0 | 0.7 | 0.070 | 0.099 | 0.25 | 2.45 |
| 5-0 | 1 | 0.10 | 0.149 | 0.68 | 6.67 |
| 4-0 | 1.5 | 0.15 | 0.199 | 0.95 | 9.32 |
| 3-0 | 2 | 0.20 | 0.249 | 1.77 | 17.4 |
| 2-0 | 3 | 0.30 | 0.339 | 2.68 | 26.3 |
| 0 | 3.5 | 0.35 | 0.399 | 3.90 | 38.2 |
| 1 | 4 | 0.40 | 0.499 | 5.08 | 49.8 |
| 2 | 5 | 0.50 | 0.599 | 6.35 | 62.3 |
| 3 and 4 | 6 | 0.60 | 0.699 | 7.29 | 71.5 |
| 5 | 7 | 0.70 | 0.799 | -- | -- |

* The tensile strength of the specified USP size is measured by straight pull.

DRUG-ELUTING SELF-RETAINING SUTURES AND METHODS RELATING THERETO

CROSS-REFERENCE TO RELATED APPLICATION

This application is a national stage filing of International Application No. PCT/US2011/059238, filed Nov. 3, 2011, which is incorporated herein by reference in its entirety and which claims the benefit under 35 U.S.C. § 119(e) of U.S. Provisional Patent Application No. 61/409,731 filed Nov. 3, 2010, which provisional application is incorporated herein by reference in its entirety.

FIELD OF INVENTION

The present invention relates generally to self-retaining systems for surgical procedures, methods of manufacturing self-retaining systems for surgical procedures, and uses thereof.

BACKGROUND OF INVENTION

Wound closure devices such as sutures, staples and tacks have been widely used in superficial and deep surgical procedures in humans and animals for closing wounds, repairing traumatic injuries or defects, joining tissues together (bringing severed tissues into approximation, closing an anatomical space, affixing single or multiple tissue layers together, creating an anastomosis between two hollow/luminal structures, adjoining tissues, attaching or reattaching tissues to their proper anatomical location), attaching foreign elements to tissues (affixing medical implants, devices, prostheses and other functional or supportive devices), and for repositioning tissues to new anatomical locations (repairs, tissue elevations, tissue grafting and related procedures) to name but a few examples.

Sutures are often used as wound closure devices. Sutures typically consist of a filamentous suture thread attached to a needle with a sharp point. Suture threads can be made from a wide variety of materials including bioabsorbable (i.e., that break down completely in the body over time), or non-absorbable (permanent; non-degradable) materials. Absorbable sutures have been found to be particularly useful in situations where suture removal might jeopardize the repair or where the natural healing process renders the support provided by the suture material unnecessary after wound healing has been completed; as in, for example, completing an uncomplicated skin closure. Non-degradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomosis. Also, a wide variety of surgical needles are available, and the shape and size of the needle body and the configuration of the needle tip is typically selected based upon the needs of the particular application.

To use an ordinary suture, the suture needle is advanced through the desired tissue on one side of the wound and then through the adjacent side of the wound. The suture is then formed into a "loop" which is completed by tying a knot in the suture to hold the wound closed. Knot-tying takes time and causes a range of complications, including, but not limited to (i) spitting (a condition where the suture, usually a knot) pushes through the skin after a subcutaneous closure), (ii) infection (bacteria are often able to attach and grow in the spaces created by a knot), (iii) bulk/mass (a significant amount of suture material left in a wound is the portion that comprises the knot), (iv) slippage (knots can slip or come untied), and (v) irritation (knots serve as a bulk "foreign body" in a wound). Suture loops associated with knot-tying may lead to ischemia (knots can create tension points that can strangulate tissue and limit blood flow to the region) and increased risk of dehiscence or rupture at the surgical wound. Knot-tying is also labor intensive and can comprise a significant percentage of the time spent closing a surgical wound. Additional operative procedure time is not only bad for the patient (complication rates rise with time spent under anesthesia), but it also adds to the overall cost of the operation (many surgical procedures are estimated to cost between $15 and $30 per minute of operating time).

Self-retaining sutures (including barbed sutures) differ from conventional sutures in that self-retaining sutures possess numerous tissue retainers (such as barbs) which anchor the self-retaining suture into the tissue following deployment and resist movement of the suture in a direction opposite to that in which the retainers face, thereby eliminating the need to tie knots to affix adjacent tissues together (a "knotless" closure). Knotless tissue-approximating devices having barbs have been previously described in, for example, U.S. Pat. No. 5,374,268, disclosing armed anchors having barb-like projections, while suture assemblies having barbed lateral members have been described in U.S. Pat. Nos. 5,584,859 and 6,264,675. Sutures having a plurality of barbs positioned along a greater portion of the suture are described in U.S. Pat. No. 5,931,855, which discloses a unidirectional barbed suture, and U.S. Pat. No. 6,241,747, which discloses a bidirectional barbed suture. Methods and apparatus for forming barbs on sutures have been described in, for example, U.S. Pat. Nos. 6,848,152. Self-retaining systems for wound closure also result in better approximation of the wound edges, evenly distribute the tension along the length of the wound (reducing areas of tension that can break or lead to ischemia), decrease the bulk of suture material remaining in the wound (by eliminating knots) and reduce spitting (the extrusion of suture material—typically knots—through the surface of the skin. All of these features are thought to reduce scarring, improve cosmesis, and increase wound strength relative to wound closures using plain sutures or staples. Thus, self-retaining sutures, because such sutures avoid knot-tying, allow patients to experience an improved clinical outcome, and also save time and costs associated with extended surgeries and follow-up treatments. It is noted that all patents, patent applications and patent publications identified throughout are incorporated herein by reference in their entirety.

The ability of self-retaining sutures to anchor and hold tissues in place even in the absence of tension applied to the suture by a knot is a feature that also provides superiority over plain sutures. When closing a wound that is under tension, this advantage manifests itself in several ways: (i) self-retaining sutures have a multiplicity of retainers which can dissipate tension along the entire length of the suture (providing hundreds of "anchor" points this produces a superior cosmetic result and lessens the chance that the suture will "slip" or pull through) as opposed to knotted interrupted sutures which concentrate the tension at discrete points; (ii) complicated wound geometries can be closed (circles, arcs, jagged edges) in a uniform manner with more precision and accuracy than can be achieved with interrupted sutures; (iii) self-retaining sutures eliminate the need for a "third hand" which is often required for maintaining tension across the wound during traditional suturing and knot-tying (to prevent "slippage" when tension is momentarily released during tying); (iv) self-retaining sutures are superior in procedures where knot-tying is technically difficult, such as in deep wounds or laparoscopic/endoscopic procedures; and (v) self-retaining sutures can be used to approximate and hold the wound prior to definitive closure. As a result, self-retaining sutures provide easier handling in anatomically tight or deep places (such as the pelvis, abdomen and thorax) and make it easier to approximate tissues in laparoscopic/endoscopic and minimally invasive procedures; all without having to secure the closure via a knot. Greater accuracy allows self-retaining sutures to be used for more complex closures (such as those with diameter mismatches, larger defects or purse string suturing) than can be accomplished with plain sutures.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over a different portion of the thread (as described with barbed retainers in U.S. Pat. Nos. 5,931,855 and. 6,241,747). Although any number of sequential or intermittent configurations of retainers are possible, a common form of bidirectional self-retaining suture involves a needle at one end of a suture thread which has barbs having tips projecting "away" from the needle until the transition point (often the midpoint) of the suture is reached; at the transition point the configuration of barbs reverses itself about 180° (such that the barbs are now facing in the opposite direction) along the remaining length of the suture thread before attaching to a second needle at the opposite end (with the result that the barbs on this portion of the suture also have tips projecting "away" from the nearest needle). Projecting "away" from the needle means that the tip of the barb is further away from the needle and the portion of suture comprising the barb may be pulled more easily through tissue in the direction of the needle than in the opposite direction. Put another way, the barbs on both "halves" of a typical bidirectional self-retaining suture have tips that point towards the middle, with a transition segment (lacking barbs) interspersed between them, and with a needle attached to either end.

With surgical procedures, it may be beneficial to deliver a drug to the surgical site during the surgical procedure. It is desirable that the drug be delivered in the appropriate concentration at the appropriate times in order to be effective for the healing process. Accordingly, it would be advantageous to be able to deliver such drugs with the application of a suture during the surgical procedure.

SUMMARY OF INVENTION

Despite the multitude of advantages of unidirectional and bidirectional self-retaining sutures, there remains a desire to improve upon the design of the suture to provide additional therapeutic benefits.

Thus, it would be desirable to provide improved self-retaining sutures having the ability to anchor into the surrounding tissue, good tissue holding capabilities and enhanced therapeutic benefits.

In accordance with the foregoing background and the limitations of the prior art, the present invention provides improved self-retaining sutures which have the ability to anchor into the surrounding tissue, good tissue holding capabilities, and enhanced clinical performance and therapeutic benefits, and methods for making and utilizing such self-retaining sutures.

In accordance with one aspect of the invention, self-retaining sutures are configured to effectively distribute or resist tension upon them when deployed in tissue and also to deliver drugs to a tissue in which the self-retaining suture is deployed.

In another aspect of the invention, a drug is impregnated in the body of a self-retaining suture prior to formation of the retainers.

In another aspect of the invention, a drug is isotropically or anisotropically distributed along the length of a self-retaining suture.

In another aspect of the invention, a drug is isotropically or anisotropically distributed over the radius of a self-retaining suture.

In another aspect of the invention, a suture is provided with one or more tissue retainers which affect the release kinetics of a drug associated with the suture.

In another aspect of the invention, a suture may include one or more tissue retainers having an uneven or roughened surface which affects the release kinetics of a drug associated with the suture.

In another aspect of the invention, a suture is provided with one or more tissue retainers which effect the release location of a drug associated with the suture.

In another aspect of the invention, a suture is provided with one or more tissue retainers which anisotropically effect the release location of a drug associated with the suture.

In another aspect of the invention, a self-retaining suture includes a section without tissue retainers disposed away from either end of the suture which effects the release of a drug associated with the suture.

In another aspect of the invention, a self-retaining suture includes an expanded section disposed away from either end of the suture which affects the release of a drug associated with the suture.

In another aspect of the invention, a suture with retainers includes a Nerve Growth Factor (NGF) as a drug useful in the repair of a nerve.

In another aspect of the invention, a method of use includes a suture that includes a NGF as a drug to repair a nerve.

The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

Features of the invention, its nature and various advantages will be apparent from the accompanying drawings and the following detailed description of various embodiments.

FIGS. 1A and 1B are perspective views of a self-retaining suture comprising a drug according to an embodiment of the present invention.

FIG. 6G illustrates suture dimensions that can benefit from the embodiments of the invention.

DETAILED DESCRIPTION

Definitions

Figure 1C:
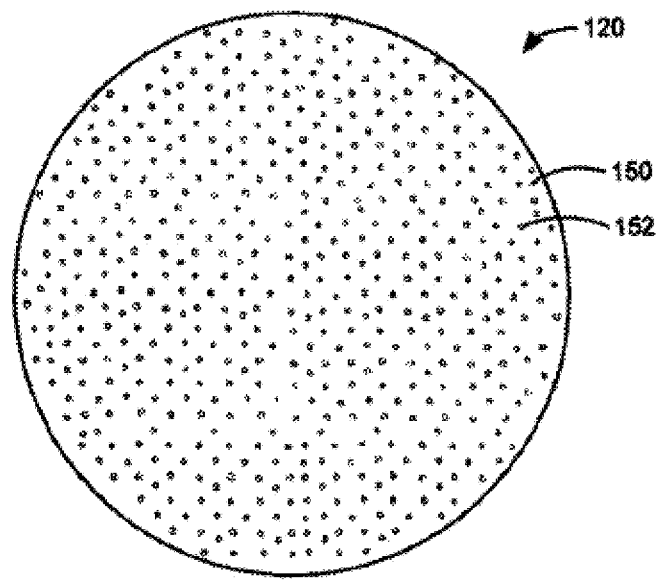
FIGS. 1C and 1D are alternative sectional views of the suture filament of FIGS. 1A and 1B illustrating parameters of drug distribution.

Definitions of certain terms that may be used hereinafter include the following.

"Armed suture" refers to a suture having a suture needle on at least one suture deployment end.

"Bidirectional suture" refers to a self-retaining suture having retainers oriented in one direction at one end and retainers oriented in the other direction at the other end. A bidirectional suture is typically armed with a needle at each end of the suture thread. Many bidirectional sutures have a transition segment located between the two barb orientations.

"Braided suture" refers to a suture comprising a multi-filamentary suture thread. The filaments in such suture threads are typically braided, twisted, or woven together.

"Degradable suture" (also referred to as "biodegradable suture" or "absorbable suture") refers to a suture which, after introduction into a tissue is broken down and absorbed by the body. Typically, the degradation process is at least partially mediated by, or performed in, a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination of these) or by a thermal or photolytic process. Polymer degradation may be characterized, for example, using gel permeation chromatography (GPC), which monitors the polymer molecular mass changes during erosion and breakdown. Degradable suture material may include polymers such as polydioxanone ("PDO"), polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). A dissolvable suture can also include partially deacetylated polyvinyl alcohol. Polymers suitable for use in degradable sutures can be linear polymers, branched polymers or multi-axial polymers. Examples of multi-axial polymers used in sutures are described in U.S.

Patent Application Publication Nos. 20020161168, now abandoned, 20040024169, issued as U.S. Pat. No. 7,026,437 on Apr. 11, 2006, and 20040116620, issued as U.S. Pat. No. 7,070,858 on Jul. 4, 2006. Sutures made from degradable suture material lose tensile strength as the material degrades. Degradable sutures can be in either a braided multifilament form or a monofilament form.

"Drug" refers to is a chemical capable of administration to an organism, which modifies or alters the organism's physiology. Preferably the "drug" is a substance intended for use in the treatment or prevention of disease. The term "drug" includes pro-active, activated, metabolized and non-metabolized drugs. Drugs include, for example, synthetic and naturally occurring toxins and bioactive substances as well as recognized pharmaceuticals, such as those listed in the "2010 Physicians' Desk Reference®" (PDR®, 2009) which is incorporated herein by reference. The term "drug" is also intended to encompass pharmaceuticals that have the indicated properties but that are discovered or made available after the filing date of this application.

"Drug-eluting suture" refers to a suture which has a drug associated with it at the time of implantation in tissue of a patient, the suture releasing the drug into the tissue of the patient subsequent to implantation. Association of a drug with a suture can be accomplished in a variety of ways. The drug is impregnated in the suture before, after, or during creation of the filament. The drug alternatively can be coated on the filament before or after retainer formation in a self-retaining suture. The drug is incorporated for example, (a) by directly affixing to the suture a formulation (e.g., by either spraying the suture with a polymer/drug film, or by dipping the suture into a polymer/drug solution), (b) by coating or impregnating the suture with a substance such as a hydrogel which will absorb the drug or includes the drug at the time coating, impregnating, or creating the suture (c) by interweaving drug-coated thread (or the polymer itself formed into a thread) into the suture structure in the case of multi-filamentary sutures, (d) constructing the suture itself with the drug in the material of manufacture or being the material of manufacture.

"Medical device" or "implant" refers to any object placed in the body for the purpose of restoring physiological function, reducing/alleviating symptoms associated with disease, and/or repairing and/or replacing damaged or diseased organs and tissues. While normally composed of biologically compatible synthetic materials (e.g., medical-grade stainless steel, titanium and other metals or polymers such as polyurethane, silicon, PLA, PLGA, PDO, and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices that can be used in procedures in conjunction with the present invention include, but are not restricted to, orthopedic implants (artificial joints, ligaments and tendons; screws, plates, and other implantable hardware), dental implants, intravascular implants (arterial and venous vascular bypass grafts, hemodialysis access grafts; both autologous and synthetic), skin grafts (autologous, synthetic), tubes, drains, implantable tissue bulking agents, pumps, shunts, sealants, surgical meshes (e.g., hernia repair meshes, tissue scaffolds), fistula treatments, spinal implants (e.g., artificial intervertebral discs, spinal fusion devices, etc.) and the like.

"Monofilament suture" refers to a suture comprising a monofilamentary suture thread.

"Needle attachment" refers to the attachment of a needle to a suture requiring same for deployment into tissue, and can include methods such as crimping, swaging, using adhesives, and so forth. The suture thread is attached to the suture needle using methods such as crimping, swaging and adhesives. Attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. US 20040088003, now abandoned). The point of attachment of the suture to the needle is known as the swage.

"Needle diameter" refers to the diameter of a suture deployment needle at the widest point of that needle. While the term "diameter" is often associated with a circular periphery, it is to be understood herein to indicate a cross-sectional dimension associated with a periphery of any shape.

"Non-degradable suture" (also referred to as "non-absorbable suture") refers to a suture comprising material that is not degraded by chain scission such as chemical reaction processes (e.g., hydrolysis, oxidation/reduction, enzymatic mechanisms or a combination of these) or by a thermal or photolytic process. Non-degradable suture material includes polyamide (also known as nylon, such as nylon 6 and nylon 6,6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethylene, silk, and cotton. Sutures made of non-degradable suture material are suitable for applications in which the suture is meant to remain permanently or is meant to be physically removed from the body.

"Retainer configurations" refers to configurations of tissue retainers and can include features such as size, shape, flexibility, surface characteristics, and so forth. These are sometimes also referred to as "barb configurations".

"Self-retaining suture" refers to a suture that comprises features on the suture filament for engaging tissue without the need for a knot or suture anchor.

"Self-retaining system" refers to a self-retaining suture together with devices for deploying the suture into tissue. Such deployment devices include, without limitation, suture needles and other deployment devices as well as sufficiently rigid and sharp ends on the suture itself to penetrate tissue.

"Suture deployment end" refers to an end of the suture to be deployed into tissue; one or both ends of the suture may be suture deployment ends. The suture deployment end may be attached to a deployment device such as a suture needle, or may be sufficiently sharp and rigid to penetrate tissue on its own.

"Suture diameter" refers to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging or other methods whereby the suture material is inserted into a channel at the blunt end of the needle which is then deformed to a final shape to hold the suture and needle together. As such, atraumatic needles do not require extra time on site for threading and the suture end at the needle attachment site is generally smaller than the needle body. In the traumatic needle, the thread comes out of the needle's hole on both sides and often the suture rips the tissues to a certain extent as it passes through. Most modern sutures are swaged atraumatic needles. Atraumatic needles may be permanently swaged to the suture or may be designed to come off the suture with a sharp straight tug. These "pop-offs" are commonly used for interrupted sutures, where each suture is only passed once and then tied. For barbed sutures that are uninterrupted, atraumatic needles are preferred. Suture needles may also be classified according to the geometry of the tip or point of the needle. For example, needles may be (i) "tapered" whereby the needle body is round and tapers smoothly to a point; (ii) "cutting" whereby the needle body is triangular and has a sharpened cutting edge on the inside; (iii) "reverse cutting" whereby the cutting edge is on the outside; (iv) "trocar point" or "taper cut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery). Suture needles may also be of several shapes including, (i) straight, (ii) half curved or ski, (iii) ¼ circle, (iv) ⅜ circle, (v) ½ circle, (vi) ⅝ circle, (v) and compound curve. Suturing needles are described, for example, in U.S. Pat. Nos. 6,322,581 and 6,214,030 (Mani, Inc., Japan); and 5,464,422 (W. L. Gore, Newark, Del.); and 5,941,899; 5,425,746; 5,306,288 and 5,156,615 (US Surgical Corp., Norwalk, Conn.); and 5,312,422 (Linvatec Corp., Largo, Fla.); and 7,063,716 (Tyco Healthcare, North Haven, Conn.). Other suturing needles are described, for example, in U.S. Pat. Nos. 6,129,741; 5,897,572; 5,676,675; and 5,693,072. The sutures described herein may be deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth). Moreover, the sutures described herein may themselves include sufficiently rigid and sharp ends so as to dispense with the requirement for deployment needles altogether.

"Suture thread" refers to the filamentary body component of the suture. The suture thread may be a monofilament, or comprise multiple filaments as in a braided suture. The suture thread may be made of any suitable biocompatible material, and may be further treated with any suitable biocompatible material, whether to enhance the sutures' strength, resilience, longevity, or other qualities, or to equip the sutures to fulfill additional functions besides joining tissues together, repositioning tissues, or attaching foreign elements to tissues.

"Tissue elevation procedure" refers to a surgical procedure for repositioning tissue from a lower elevation to a higher elevation (i.e. moving the tissue in a direction opposite to the direction of gravity). The retaining ligaments of the face support facial soft tissue in the normal anatomic position. However, with age, gravitational effects and loss of tissue volume effect downward migration of tissue, and fat descends into the plane between the superficial and deep facial fascia, thus causing facial tissue to sag. Face-lift procedures are designed to lift these sagging tissues, and are one example of a more general class of medical procedure known as a tissue elevation procedure. More generally, a tissue elevation procedure reverses the appearance change that results from effects of aging and gravity over time, and other temporal effects that cause tissue to sag, such as genetic effects. It should be noted that tissue can also be repositioned without elevation; in some procedures tissues are repositioned laterally (away from the midline), medially (towards the midline) or inferiorly (lowered) in order to restore symmetry (i.e. repositioned such that the left and right sides of the body "match").

"Tissue retainer" (or simply "retainer") refers to a physical feature of a suture filament which is adapted to mechanically engage tissue and resist movement of the suture in at least one axial direction. By way of example only, tissue retainer or retainers can include hooks, projections, barbs, darts, extensions, bulges, anchors, protuberances, spurs, bumps, points, cogs, tissue engagers, traction devices, surface roughness, surface irregularities, surface defects, edges, facets and the like. In certain configurations, tissue retainers are adapted to engage tissue to resist movement of the suture in a direction other than the direction in which the suture is deployed into the tissue by the surgeon, by being oriented to substantially face the deployment direction. In some embodiments the retainers lie flat when pulled in the deployment direction and open or "fan out" when pulled in a direction contrary to the deployment direction. As the tissue-penetrating end of each retainer faces away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from the deployment position (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self-retaining suture in place. In certain other embodiments, the tissue retainers are configured to permit motion of the suture in one direction and resist movement of the suture in another direction without fanning out or deploying. In certain other configurations, the tissue retainers are configured or combined with other tissue retainers to resist motion of the suture filament in both directions. Typically a suture having such retainers is deployed through a device such as a cannula which prevents contact between the retainers and the tissue until the suture is in the desired location.

"Transition segment" refers to a retainer-free portion of a bidirectional suture located between a first set of retainers oriented in one direction and a second set of retainers oriented in another direction. The transition segment can be at about the midpoint of the self-retaining suture, or closer to one end of the self-retaining suture to form an asymmetrical self-retaining suture system.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound may be caused by an act, such as a puncture, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

Drug-Eluting Self-Retaining Sutures

As discussed above, embodiments of the present invention provides compositions, configurations, methods of manufacturing and methods of using self-retaining systems in surgical procedures which the ability to anchor into the surrounding tissue to provide superior holding strength and improve clinical performance while providing a drug to this tissue surrounding the suture.

Self-Retaining Suture System

FIG. 1A illustrates a bidirectional self-retaining suture system 100. Self-retaining suture system 100 comprises needles 110, 112 attached to self-retaining suture thread 102. Self-retaining suture thread 102 includes a plurality of retainers 130 distributed on the surface of a filament 120. In lead-in region 140 of filament 120 there are no retainers 130. In region 142 of filament 120 there are a plurality of retainers 130 arranged such that the suture can be deployed in the direction of needle 110 but resists movement in the direction of needle 112. In transition region 144, there are no retainers 130. In region 146, there are a plurality of retainers 130 arranged such that the suture can be deployed in the direction of needle 112 but resists movement in the direction of needle 110. In lead-in region 148 of filament 120 there are no retainers 130. A break is shown in each of regions 140, 142, 144, 146 and 148 to indicate that the length of each region may be varied and selected depending upon the application for which the suture is intended to be used. Although a bidirectional self-retaining suture system 100 is illustrated, the present invention includes self-retaining suture systems of a wide variety of retainer and needle configurations described above. Likewise the configuration of each of needles 110 and 112 can be any of the range of different surgical needles developed for use in different applications. Needles 110 and 112 may have the same configuration or different configurations.

Figure 1D:
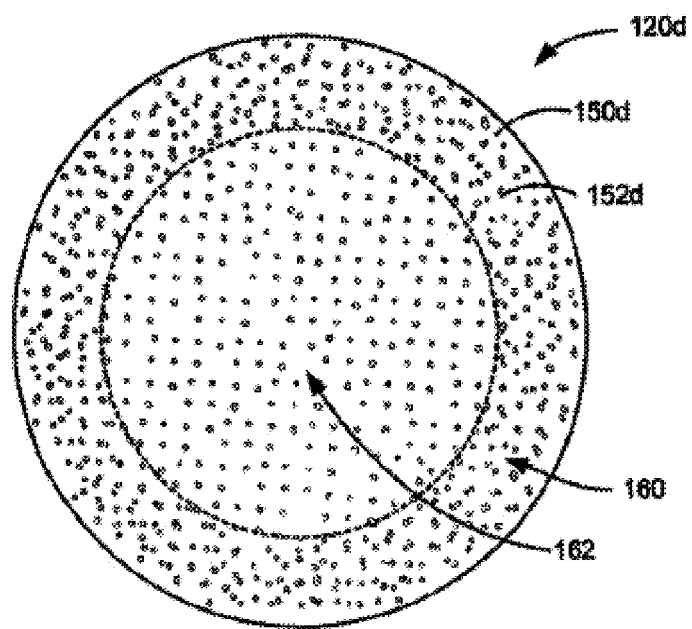

Filament 120 comprises a drug 152 (FIGS. 1C, 1D). The drug 152 is in a coating layer on filament 120 or impregnated in the material 150 of filament 120. Various methods may be used to make sutures that carry drugs. For example, such methods include direct extrusion as described in U.S. Pat. No. 6,596,296 (TissueGen, Inc., Dallas, Tex.) to create filaments wherein the drug is uniformly distributed as in FIG. 1C. Alternatively "core/sheath" and other multicomponent configurations as illustrated in FIG. 1D may also be extruded as described in U.S. Pat. No. 7,033,603 (TissueGen, Inc., Dallas, Tex.). U.S. Pat. Nos. 6,596,296 and 7,033,603 are herein incorporated by reference. Alternate methods such as coating (e.g., spraying or dipping) all or part of the sutures or an "over the wire" extrusion as described in U.S. Pat. No. 6,858,222 (TissueGen, Inc., Dallas, Tex.) may also be used. Additionally, gradients of the drug along the suture are sometimes preferred. These linear anisotropies are described in U.S. Pat. Nos. 6,596,296, 6,858,222, and 7,514,095 (TissueGen, Inc., Dallas, Tex.), the latter of which is also hereby incorporated by reference. Additionally, sutures themselves can be made at least in part of materials that have pharmaceutical activity in or around the site where the sutures are implanted or inserted. In certain embodiments, only selected portions (such as middle sections or the self-retaining sections) of a self-retaining suture are coated or otherwise comprise the drug or drugs. In certain further embodiments, portions of the sutures are selectively left unassociated with a drug or drugs or are associated with a drug different from another drug associated with a different portion of the self-retaining suture. For example, in some embodiments, the suture surfaces between retainer and main suture body in which tissue are gripped are selectively associated with one or more drugs that enhance healing and prevent scarring. In other embodiments, temporally phased release of one or more drugs may be designed to coincide with known phases of wound healing as a means to reduce scaring and enhance the body's natural wound healing processes. This may be accomplished, for example, by multilayer filaments as described in U.S. Pat. No. 7,033,603 or by using multiple means of incorporating the drug in the base material of the filament, such as simultaneous use of nanoparticles and microspheres within the same filament as described in U.S. Pat. No. 6,858,222. In certain other embodiments, the suture surface may comprise one or more wells including one or more drugs. In other embodiments, all sections of sutures are coated with the drug(s). The methods for applying drugs to sutures include, for example: (a) extrusion, (b) by directly affixing to the suture a formulation (e.g., by either spraying the suture with a polymer/drug film, or by dipping the suture into a polymer/drug solution), (c) by coating the suture with a substance such as a hydrogel which will in turn absorb the composition, (d) by interweaving formulation-coated thread (or the polymer itself formed into a thread) into the suture structure in the case of multi-filamentary sutures, (e) constructing the suture itself with a drug-containing composition.

Drug-eluting self-retaining suture systems 100 (including barbed sutures) differ from conventional sutures in that, in addition to providing drugs directly to a tissue of interest, the self-retaining sutures possess numerous tissue retainers 130 (such as barbs) which anchor the self-retaining suture system 100 into the tissue following deployment and resist movement of the suture in a direction opposite to that in which the retainers face, thereby eliminating the need to tie knots to affix adjacent tissues together (a "knotless" closure).

The drug-eluting self-retaining suture systems for wound closure also result in better approximation of the wound edges, evenly distribute the tension along the length of the wound (reducing areas of tension that can break or lead to ischemia), decrease the bulk of suture material remaining in the wound (by eliminating knots) and reduce spitting (the extrusion of suture material—typically knots—through the surface of the skin. All of these features are thought to reduce scarring, improve cosmesis, and increase wound strength relative to wound closures using plain sutures or staples. Thus, self-retaining sutures, because such sutures avoid knot-tying, allow patients to experience an improved clinical outcome, and also save time and costs associated with extended surgeries and follow-up treatments. Also, by avoiding knot-tying, drug-eluting self retaining sutures avoid local concentrations of drugs in the vicinity of such knots.

The ability of drug-eluting self-retaining sutures to anchor and hold tissues in place even in the absence of tension applied to the suture by a knot is a feature that provides superiority over plain sutures. When closing a wound that is under tension, this advantage manifests itself in several ways: (i) self-retaining sutures have a multiplicity of retainers which can dissipate tension along the entire length of the suture (providing hundreds of "anchor" points this produces a superior cosmetic result and lessens the chance that the suture will "slip" or pull through) as opposed to knotted interrupted sutures which concentrate the tension at discrete points; (ii) complicated wound geometries can be closed (circles, arcs, jagged edges) in a uniform manner with more precision and accuracy than can be achieved with interrupted sutures; (iii) self-retaining sutures eliminate the need for a "third hand" which is often required for maintaining tension across the wound during traditional suturing and knot-tying (to prevent "slippage" when tension is momentarily released during tying); (iv) self-retaining sutures are superior in procedures where knot-tying is technically difficult, such as in deep wounds or laparoscopic/endoscopic procedures; (v) self-retaining sutures can be used to approximate and hold the wound prior to definitive closure; (vi) drug-eluting self-retaining sutures can deliver drugs more evenly to a tissue through broader and more uniform distribution in the tissue; and (vii) the retainers of a drug-eluting self-retaining suture provide an additional interface for distribution of drugs into the tissue.

Drugs for Incorporation in Self-Retaining Suture

The purpose of the drug-eluting self-retaining suture determines the sort of drug that is applied to or incorporated in the suture. For example, self-retaining sutures having anti-proliferative drugs may be used in closing tumor excision sites, self-retaining sutures containing or coated with nerve growth factor (NGF) may be used in the repair of damaged nerves, while self-retaining sutures with fibrosing drugs may be used in tissue repositioning procedures and those having anti-scarring drugs may be used for wound closure on the skin. Bone growth factors such as Bone Morphogenic Proteins (BMP) can also be incorporated within the sutures. The drugs may also include a plurality of compositions either together or on different portions of the suture, where the multiple compositions can be selected either for different purposes (such as combinations of growth factors, analgesics, anti-infective and anti-scarring agents) or for the synergistic effects of the combination.

The drug or drugs incorporated in or coated on a self-retaining suture in embodiments of the present invention include, for example, compositions to promote healing and prevent undesirable effects such as scar formation, infection, pain, and so forth. The drugs include without limitation growth factors such as nerve growth factor (NGF), bone grown factor (BGF), tissue repair factors, trophic factors to guide tissue repair, inhibition agonists to suppress factors which inhibit tissue repair, mitogenic agents to promote cell division for tissue repair, anti-proliferative agents, anti-angiogenic agents, anti-infective agents, fibrosis-inducing agents, anti-scarring agents, lubricious agents, echogenic agents, anti-inflammatory agents, cell cycle inhibitors, analgesics, and anti-microtubule agents. In one embodiment a drug can be utilized in conjunction with the suture (introduced separately or adhered to the suture or incorporated into a material of the suture) to encourage fibrosis. Fibrosis-inducing drugs which may be used in conjunction with a drug-eluting self-retaining suture according to the present invention are described in U.S. Pat. No. 7,166,570 titled "Medical Implants And Fibrosis-Inducing Agents" to Hunter et al., which is incorporated herein by reference. Other drugs which may be used in drug-eluting self-retaining suture of the present invention include all drugs and agents disclosed in U.S. patent application Ser. No. 12/162,572, published as U.S. Pub. No. 2009/0226500 on Sep. 10, 2009, titled "Sutures And Anti-Scarring Agents" to Avelar et al., which is incorporated herein by reference.

In some embodiments (FIG. 1C), the drug 152 is uniformly distributed in the material 150 of filament 120. In other embodiments (FIG. 1D), drug 152 is anisotropically distributed. For example, filament 120 may have higher concentrations of a drug in an outer layer of material as compared to the inner core of material, or vice versa. Also, for example, filament 120 may have a higher concentration of a drug at one end as compared to another. Also for example, filament 120 may have a higher concentration of a drug in the middle than towards the ends. Where a drug is anisotropically distributed within a filament 120, the concentration of the drug 152 may change gradually from region to region or there may be changes in concentration from one region to another region. Different regions of filament 120 having different drug concentrations may correspond to regions of the filament 120 having retainers, no retainers or retainers in one orientation compared to another orientation. Where a drug 152 is anisotropically distributed within a filament 120, the filament 120 may be provided with visible or otherwise detectable markers which indicate regions have greater or lesser concentrations of the drug 152 in order to identify said regions during manufacturing and/or utilization of the self-retaining suture system 100.

In other embodiments, a very thin coating including one of more drug(s) can be applied to the suture by any of the aforementioned techniques before the retainers are formed, so that when the retainers engage, the engaging surface is substantially free of the coating. In this way, tissue being sutured contacts a coated surface of the suture as the suture is introduced, but when the retainer engages, a non-coated surface of the retainer contacts the tissue. Other embodiments that may provide drug-exposing suture surfaces include sutures extruded with the drug(s) uniformly dispersed as in FIG. 1C, sutures extruded as a multi-layer "core/sheath" arrangement as shown in FIG. 1D, and sutures coated after or during formation of retainers on the suture body if, for example, a fully-coated rather than selectively-coated suture is desired. In yet another alternative, a suture is selectively coated either during or after formation of retainers by exposing only selected portions of the suture to the coating.

The particular purpose to which the suture is to be put or the composition may determine whether a fully- or selectively-loaded suture is appropriate, for example coatings such as those comprising fibrosing agents may suitably be applied to all or part of the suture (such as the tissue-engaging surfaces). Coatings such as those comprising such compounds as growth factors may suitably be applied to the entire suture and/or incorporated into the material from which the filament is made prior to formation of the retainers. Methods of making drug-loaded filaments are described in: U.S. Pat. No. 7,514,095 titled "Fabrication Of Drug Loaded Biodegradable Polymer Fibers" and U.S. Pat. No. 7,033,603 titled "Drug Releasing Biodegradable Fiber For Delivery Of Therapeutics", both of which are incorporated by reference herein. Additional methods of drug loading a preformed filament may also be utilized including, without limitation, dip coating, spray coating, curtain coating and/or chemical deposition (such as chemical vapor deposition CVD). Moreover, if the material 152d of filament 120d (FIG. 1D) is a porous material, drug 152d may be impregnated in filament 120d by dipping the filament 120d in a solution of the drug 152d. The drug 152d diffuses from the outside of filament 120d towards the center by controlling the time allowed for this diffusion, the filament 120d the concentration of the drug 152d in center 162 can be made lower than the concentration in sheath region 160.

The structure of the suture may influence the choice and extent of application and/or incorporation of a drug or drugs; for example, sutures having an expanded segment may include a fibrosis-inducing composition in or on the expanded segment to further secure the segment in position in the tissue. Sutures used in tissue repair may include for example a gradient of concentration of the trophic factors such that the suture delivers a gradient of trophic factors to the tissue to guide repair. The structure of the suture and retainers can influence/control the release kinetics of the drug or drugs. The location of the incorporation of coating of the drug will also influence/control the release kinetics of the drug.

As sutures are made in a variety of configurations and sizes, the exact dose of drug administered will vary with suture size, length, diameter, surface area, design and portions of the suture coated. However, certain principles can be applied in the application of this art. For example, in the context of coated sutures, drug dose can be calculated as a function of dose per unit area (of the portion of the suture being coated), or total drug dose. Total drug dose administered can be measured and appropriate surface concentrations of active drug can be determined. The total drug administered will typically be substantially less than the equivalent systemic dose, because, by being associated with the self-retaining suture, the drug will be distributed directly in the vicinity of the target tissue rather than being evenly distributed through the whole body. Regardless of the method of application of the drug to the suture, the preferred agents, used alone or in combination, should be administered under the following dosing guidelines:

In embodiments of the present invention, drugs are used at concentrations that range from several times more than, to 50%, 20%, 10%, 5%, or even less than 1% of the concentration typically used for a systemic dose application. In certain embodiments, the drug is released from the composition in effective concentrations in a time period that is measured from the time of infiltration into tissue adjacent to the suture, which ranges from about less than 1 day to about 180 days. Generally, the release time may also be from about less than 1 day to about 180 days; from about 7 days to about 14 days; from about 14 days to about 28 days; from about 28 days to about 56 days; from about 56 days to about 90 days; from about 90 days to about 180 days. The release kinetics are affected by the surface area of retainers in a particular region and thus should be validated for particular retainer configurations to achieve the desired final kinetics.

For example, where anti-infective agents are associated with a self-retaining suture, alone or in combination, they may be administered under the following dosing guidelines. The total amount (dose) of anti-infective agent in the composition can be in the range of about 0.01-1 µg, or about 1-10 µg, or about 10-100 mg or about 100 µg-1 mg or about 1-10 mg, or about 10-100 mg, or about 100 to 250 mg for coating a suture or a portion thereof or for infiltrating a tissue where a suture has been, is being, or is to be, implanted, or about 250-1000 mg for infiltrating a tissue where a suture has been, is being, or is to be, implanted. In certain embodiments of the present invention the dose (amount) of anti-infective agent per unit area of suture or tissue surface to which the agent is applied may be in the range of about 0.01 µg/mm$^2$ to 1 µg/mm2, or about 1 µg/mm$^2$ to 10 µg/mm$^2$, or about 10 µg/mm$^2$ to 100 µg/mm$^2$, or about 100 µg/mm$^2$ to 250 µg/mm$^2$. As different filament materials and retainer configurations will release the anti-infective agent at differing rates, the above dosing parameters should be utilized in combination with the release rate of the drug from the filament and retainers such that a minimum concentration of about $10^{-8}$ M to $10^{-7}$ M, or about $10^{-7}$ M to $10^{-6}$ M or about $10^{-6}$ M to $10^{-5}$ M or about $10^{-5}$ M to $10^{-4}$ M of the agent is maintained in the vicinity of or on the tissue surface to maintain the desired therapeutic effect for the required period of time. The required minimum concentration is dependent on the potency of the agent under consideration and can be determined using standard tests such as the Minimum Inhibitory Concentration (M.I.C.) test.

FIG. 1B illustrates a magnified view of self-retaining suture 102 in region 142. As shown in FIG. 1B, a plurality of retainers 130 is distributed on the surface of filament 120. The affixation of self-retaining sutures after deployment in tissue entails the penetration of retainer ends into the surrounding tissue resulting in tissue being caught between the retainer and the suture body. The inner surface of the retainer that is in contact with the tissue that is caught between the retainer 130 and the filament 120, herein referred to as the "tissue engagement surface" or "inner retainer surface," can be adapted to better engage the tissue and also to better distribute drugs in a tissue. As illustrated in FIG. 1B, each retainer 130 has a tip 132 and tissue retainer surface 134. When self-retaining suture thread 102 is moved in the direction of arrow 138a, retainer 130 lies flat against the body of filament 120. However, when self-retaining suture thread 102 is moved in the direction of arrow 138b, tip 132 or retainer 130 engages tissue surrounding filament 120 and causes retainer 130 to fan out from filament 120 and engage the tissue with face 134 thereby preventing movement of the suture in that direction and providing an additional surface from which to provide drugs to the tissue. It should be noted that the surface area of the filament 120 is also increased by the presence of retainers 130 as compared to portions of filament with no retainers.

FIG. 1C shows a cross-sectional view of filament 120. As can been seen in FIG. 1C, filament 120 includes a material 150 and a drug 152. In the embodiment of FIG. 1C the distribution of drug 152 is isotropic or homogenous across the radius of filament 120. FIG. 1D shows a cross-sectional view of an alternative filament 120d. As can been seen in FIG. 1D, filament 120d includes a material 150d and a drug 152d. In the embodiment of FIG. 1D the distribution of drug 152d is anisotropic across the radius of filament 120. Specifically, the concentration of drug 152d is greater in a sheath region 160 of filament 120d than in the core region 162.

In alternative embodiments a retainer 130 may comprise the material of the sheath region 160 and also some portion of the core region 162 or another non-sheath material. In such embodiments the materials are selected such that the properties of the materials in the retainer permit or enhance the function of the retainer such as by facilitating elevation of the retainer 130. As the majority of drug 152d is closer to the surface of filament 120d as compared to the embodiment of FIG. 1C, the drug 152d can be expected to be deployed into the tissue more rapidly than in the embodiment of FIG. 1C. Conversely, where higher concentrations of drug are found in the core region 162 the drug 152d can be expected to be deployed into the tissue less rapidly. Thus the distribution of drug concentration can be used to control the release kinetics of the drug or drug(s) and/or sequence the release of drugs from a self-retaining suture. In alternative embodiments, different drugs are provided in the core region 162 and sheath region 160. In such case, the drug of the sheath region 160 will be provided sooner, and or faster than the drug in the core region 162—allowing for temporal sequencing of the distribution of the drugs to the tissue.

Filament 120d is formed by any method known in the art for making a filament having a drug associated with one or more components thereof (for example a core and/or a sheath) (drug-eluting suture). One suitable method is co-extrusion of materials having the required drug concentration as disclosed in U.S. Pat. No. 7,033,603 and will be further described with respect to FIG. 3A. Another suitable method is extrusion of a material over a preformed filament as disclosed in U.S. Pat. No. 6,596,296 (TissueGen, Inc., Dallas, Tex.), incorporated by reference herein, and will be further described with respect to FIG. 3B. Where drugs are incorporated in the material 150d before or during manufacturing of filament 120d, care must be taken to ensure that the manufacturing process does not denature the drug 152d. Moreover, controls must be put in place so that both the filament and retainer manufacturing processes do not cross-contaminate drugs from one batch of sutures to another batch of sutures.

Figure 1E:
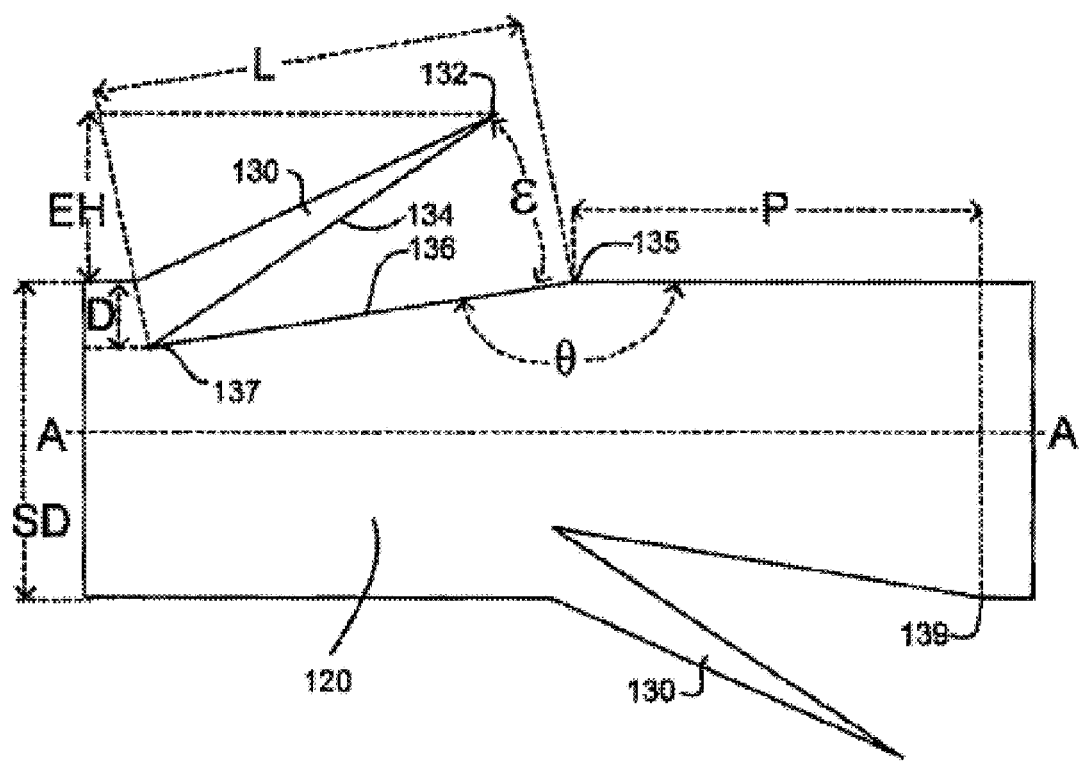
FIGS. 1E and 1F are enlarged sectional views of the suture thread of the self-retaining suture system of FIGS. 1A and 1B illustrating parameters of the retainers and retainer distribution.

FIG. 1E shows a sectional diagram through a retainer 130. Note that where retainer 130 is cut into filament 120 it leaves a cut-out depression 136. The cut-out depression 136 has a cut tip 135 which corresponds with the tip 132 of the retainer 130. The geometry of retainer 130 (retainer cut angle, retainer cut depth, retainer cut length, retainer cut distance, etc.) and/or the spatial arrangement of the retainers 130 is varied to enhance engagement of tissue by the retainers. Retainer 130 is shown elevated above filament 120 in order to show the parameters related to the retainer and elevation of the retainer.

Figure 1F:
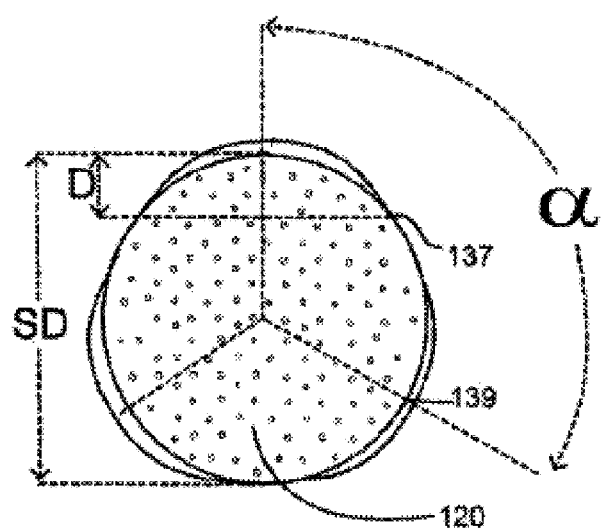

The parameters shown in FIG. 1E include the longitudinal axis of the suture A-A, the suture diameter SD, the retainer length L, the retainer cut depth D, the retainer cut angle Θ (theta), the retainer elevation angle ϵ (epsilon), the retainer cut distance P. The cut distance P is the distance between adjacent retainers measured along the longitudinal axis it can be measured as the distance from one cut-tip 135 to the adjacent cut-tip 139. The retainer cut angle Θ is the angle between the cut depression 136 and the longitudinal axis A-A surface of filament 120. Cut angle Θ can be measured between the cut depression 136 and the surface of filament 120 which is parallel to longitudinal axis A-A. Retainer elevation angle ϵ is the angle between the inner retainer surface 134 and the cut depression surface 136. The spirality angle α is the angle of rotation about the longitudinal axis between adjacent cut tips 135, 139. Where adjacent retainers are on opposite sides of filament 120, as shown in FIG. 1E, the spirality angle α is 180 degrees. FIG. 1F shows a section of an alternative filament configuration looking along the long axis. As shown in FIG. 1F, the spirality angle α is 120 degrees. FIG. 1F also shows a straight line illustrating the position of the base 137 of cut depression 136. For a straight cut such as shown in FIG. 1F, the cut depth D is the maximum distance between base 137 and the surface of filament 120.

Retainer Formation and Elevation

Self-retaining suture threads described herein are produced by any suitable method, including without limitation, injection molding, stamping, cutting, laser, extrusion, and so forth. With respect to cutting, polymeric thread or filaments are manufactured or purchased for the suture body, and the retainers can be subsequently cut onto the suture body; the retainers are hand-cut, laser-cut, or mechanically machine-cut using blades, cutting wheels, grinding wheels, and so forth. A drug is coated on the filament or impregnated in the material of the filament before, during or after the creation of filament. During cutting either the cutting device or the suture thread is moved relative to the other, or both are moved, to control the size, shape and depth of the cut and the resulting retainer. Particular methods for cutting barbs on a filament are described in U.S. patent application Ser. No. 09/943,733, issued as U.S. Pat. No. 6,848,152 on Feb. 1, 2005,titled "Method Of Forming Barbs On A Suture And Apparatus For Performing Same" to Genova et al., and U.S. patent application Ser. No. 10/065,280, issued as U.S. Pat. No. 10,065,280 on Sep. 4, 2018, titled "Barbed Sutures" to Leung et al. both of which are incorporated herein by reference.

Figure 2A:
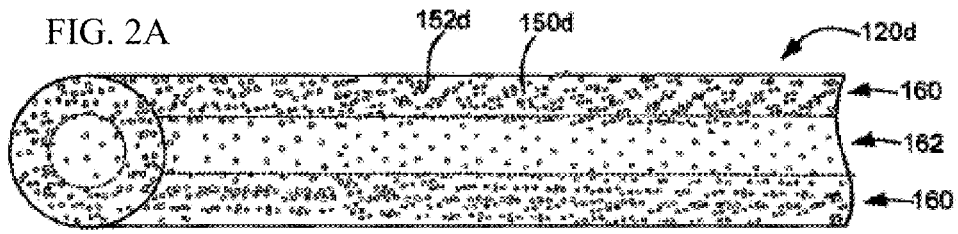
FIGS. 2A, 2B and 2C are sectional views illustrating steps in the creation of a retainer of a self-retaining suture comprising a drug according to an embodiment of the present invention.
Figure 2B:
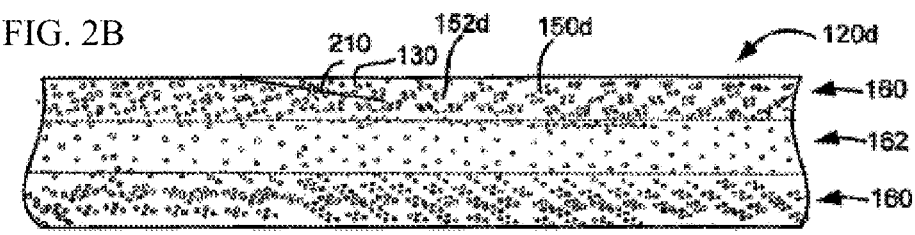
Figure 2C:
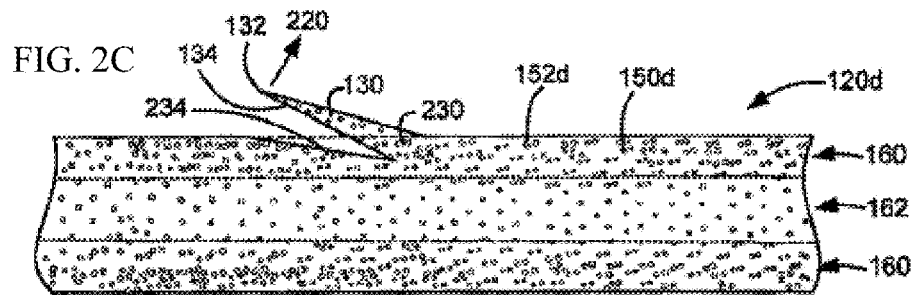

Referring now to FIGS. 2A, 2B and 2C where an exemplary process for making a retainer 130 in filament 120d is provided. FIG. 2A shows a longitudinal cross-section of filament 120d. As shown in FIG. 2A, filament 120d comprises core region 162 having a lower concentration of drug 152d in material 150d and a sheath region 160 having a higher concentration of drug 152d. In alternative embodiments, a different drug or drug(s) are provided in the core region 162 as compared to the sheath region 160. In alternative embodiments the same concentration of a drug or drug(s) are deployed across the entire radius of the filament 120d.

As shown in FIG. 2B a retainer 130 is formed on filament 120d by making a cut 210 into sheath region 160 of filament 120d. Cut 210 can be made using any of a wide range of technologies. Such technologies include hand-cutting, laser-cutting, or mechanically machine-cutting using blades, cutting wheels, grinding wheels, and so forth. Note that in this embodiment, the depth of cut has been selected such that cut 210 is entirely within sheath region 160 and does not penetrate into core region 162. As shown in FIG. 2B, retainer 130 may still lay flat against the surface of filament 120d after cut 210 has been made in material of sheath region 160.

In order for retainer 130 to more effectively engage tissue after deployment, tip 132 is preferably elevated above the surface of filament 120d. As shown in FIG. 2C, after the retainer cutting step of FIG. 2B, retainer 130 is mechanically bent away from the body of filament 120d in the direction shown by arrow 220. Tip 132 is moved above the surface of filament 120d and tissue engagement surface 134 is exposed. The cut filament surface 234 is also exposed. The elevation of retainer 130 can be achieved by a number of mechanisms. In a simple example, a cutting blade is used to form cut 210 and the cutting blade is then removed from cut 210 in a manner that bends retainer 130 away from the body of filament 120d. In an alternative example, the retainer is mechanically elevated by a device other than the blade. Where the drug 152d is incorporated in filament 120d prior to forming retainers 130, care must be taken to ensure that the retainer forming process does not denature the drug 152d.

If the material 150d is too elastic, retainer 130 will spring back to the retainer's previous position flush with the surface of filament 120d (as shown by the dotted line) after elevation of the retainer. This is also the case if the material does not have the ability to undergo permanent deformation. Thus, according to a specific embodiment of the present invention, material 150d is selected such that it is sufficiently plastically deformable that after retainer 130 has been moved away from filament 120d, retainer 130d remains in its new deformed shape with the tip 132 of retainer 130 substantially elevated above the surface of filament 120d and tissue engagement surface 134 exposed. Sheath material 150d is selected such that the mechanical movement of tip 132 of retainer away from filament 120d is sufficient to plastically deform the region 230 of the material of sheath region 160 at the base of retainer 130 causing it to take on a new permanent shape. In some embodiments a the core region 162 is made from a different material then the sheath region thus allowing selection of a material 162 is selected to have significantly lower plasticity and significantly higher elasticity and/or tensile strength than the sheath region. In other embodiments, the filament is made from a single polymer. In other embodiments the filament is made from a single polymer but the polymer comprises different concentrations of drug in different regions of the filament.

When a retainer 130 is formed in filament 120d, the surface area of the filament 120d and retainer 130 is increased relative to the filament alone. Essentially, the surface area is increased by the surface area of the tissue engagement surface 134 and cut filament surface 234. Where a drug 152d is impregnated in the material 150d of filament 120d, the release kinetics of the drug is affected by the surface area. Because the retainers 130d are formed on the surface of filament 120d, the retainers 130d are made, in this embodiment, entirely of sheath region 160 containing a higher concentration of drug 152d. Furthermore, in specific embodiments of the present invention, retainers 130d include little or none of core region 162. Thus, the size, number and density of retainers 130 among other factors can affect the release kinetics of the drug in regions of the filament bearing retainers 130. The release kinetics are affected by the surface area of retainers in a particular region and thus should be validated for particular retainer configurations to achieve the desired final kinetics.

In some embodiments, a drug may homogenously distribute along the length of filament 120d yet the release kinetics are rendered anisotropic by the distribution, shape or size of retainers 130. For example, in regions of filament 120 having a greater density of retainers 130, the drug is released to a tissue faster than in regions having fewer or no retainers. Also, for example, a section of the filament 102d having no retainers may release the drug more slowly and over a more extended period of time. Alternatively, the drug is distributed heterogeneously in different regions of a filament 102d in order that the release kinetics are homogeneous across regions having more, less or no retainers. Moreover, in some embodiments, filament 120d is provided with a coating (not shown) which delays or prevents migration of the drug 152d out of filament 120d. In such case, drug 152d will migrate out of filament 120d preferentially or sooner where retainers 130 disrupt the coating and expose the interior of filament 120d on tissue engagement surface 134 and filament cut surface 234.

Figure 2D:
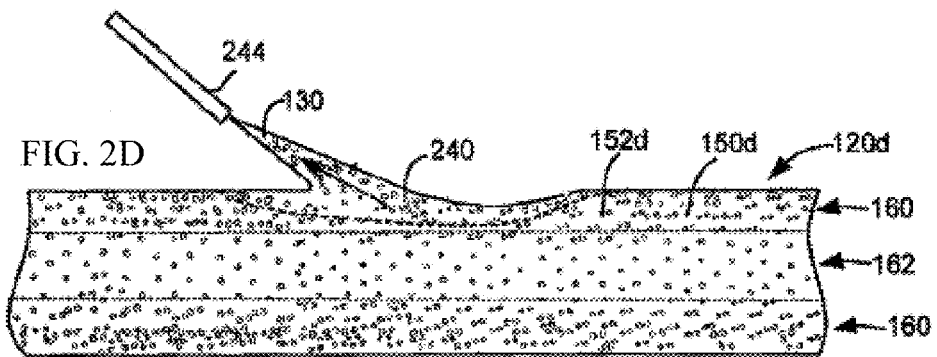
FIG. 2D is a sectional view of an alternative step in the creation of a retainer of a self-retaining suture comprising a drug according to an embodiment of the present invention.

In other embodiments, retainer 130 is formed by a process other than cutting into the sheath of the filament. For example, as shown in FIG. 2D retainers can be formed by melting the material 150d in region 240 and then drawing material out of filament 120d with device 244 to form retainer 130 and then cooling the material 150d. In this embodiment the material 150d is selected such that it may be melted and manipulated without disrupting the tensile strength of the core region 162. In alternative embodiments a preformed retainer is affixed mechanically, adhesively or by melting to the sheath. The sheath material is in this embodiment selected to enhance the affixation of the retainer to the filament and retention of the retainer by the filament. In another embodiment molten material is formed onto the sheath in the shape of a retainer and the molten material fuses with the sheath material. The material in this case is selected to enhance the adhesion or fusion with the externally applied molten material. In some cases the molten material is the same material as the material of the filament 120d and may include drug 152d. Where the drug 152d is incorporated in filament or retainer material 120d prior to forming retainers 130, care must be also taken to ensure that the retainer-forming process does not denature the drug 152d.

In certain other embodiments, the suture is a relatively short suture with sharp pointing ends. Such a suture may function similar to a staple when used in connecting tissues and thus permits a surgeon to rapidly and securely attach the edges of a wound in a body tissue or reconfigure the tissue without the necessity for threading and tying numerous individual stitches or for the use of complicated tools and/or techniques to insert the suture. This type of sutures may thus be referred to as "suture connector." In certain embodiments, the suture connector is a bi-directional self-retaining suture. In certain other embodiments, the suture connector may be made by linking two relatively short uni-directional self-retaining sutures together to form a bi-directional self-retaining suture (see, U.S. Pat. No. 6,241,747). In other embodiments, the drug-eluting self-retaining suture is used to anchor a two or three-dimensional scaffold including comprising a woven, non-woven, or knitted, mesh wherein said fibers comprise any of the compositions described herein above. The mesh may include addition filaments which may or may not be drug-eluting.

Filament Materials

The filament material is selected to have properties useful for retainer formation, elevation and deployment as well as strength and flexibility of the self-retaining suture. In some embodiments a different material is used in the core of the suture as opposed to the sheath. In such cases the core is chosen based on its properties of strength and flexibility and the sheath material is selected to have properties useful for retainer formation, elevation and deployment. The suture materials are non-degradable or biodegradable so long as the material is suitable for coating or incorporating a drug and releasing said drug in vivo with suitable release kinetics. Suitable materials include many materials that are currently used for making sutures. The release kinetics are affected by the surface area of retainers in a particular region and thus should be validated for particular retainer configurations to achieve the desired final kinetics.

Suitable non-degradable suture materials include polyamide (also known as nylon, such as nylon 6 and nylon 6,6), polyester (e.g., polyethylene terephthlate), polytetrafluoroethylenes (e.g., expanded polytetrafluoroethylene), polyether-ester such as polybutester (block copolymer of butylene terephthalate and polytetra methylene ether glycol), 4-hydroxybutyrate, polyhydroxylalkanoate, polyurethane, metals and metal alloys (e.g., stainless steel wire), polypropylene, polyethylene, silk, cotton and/or combinations thereof.

Suitable biodegradable materials for the filament include single polymer, co-polymer or a blend of polymers of poly(L-lactic acid), poly(p-dioxanone), poly(DL-lactic acid), polycaprolactone, poly(glycolic acid), polyanhydride, polyglycolic acid homopolymer, copolymers of glycolide and ε-caprolactone, copolymers of glycolide and lactide, copolymers of trimethylene carbonate and glycolide with diethylene glycol (e.g., MAXON™, Tyco Healthcare Group), polyhydroxylalkanoates (such as poly(4-hydroxybutyrate) or poly(4-hydroxybutyrate-co-3-hydroxybutyrate)), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). Naturally occurring polymers may also be used such as reconstituted collagen, fibrin, or natural silks, cellulose, starch, chitin, polypeptides modified polysaccharides, modified proteins and/or combinations of the above with synthetic suture materials listed above. Other polymers which may be used in drug-eluting self-retaining sutures of the present invention include all polymers disclosed in U.S. patent application Ser. No. 12/162,572, now abandoned, titled "Sutures And Anti-Scarring Agents" to Avelar et al. which is incorporated herein by reference.

Manufacture of Stock Filaments

As described above, a drug-eluting suture filament can be made in many different ways.

Figure 3A:
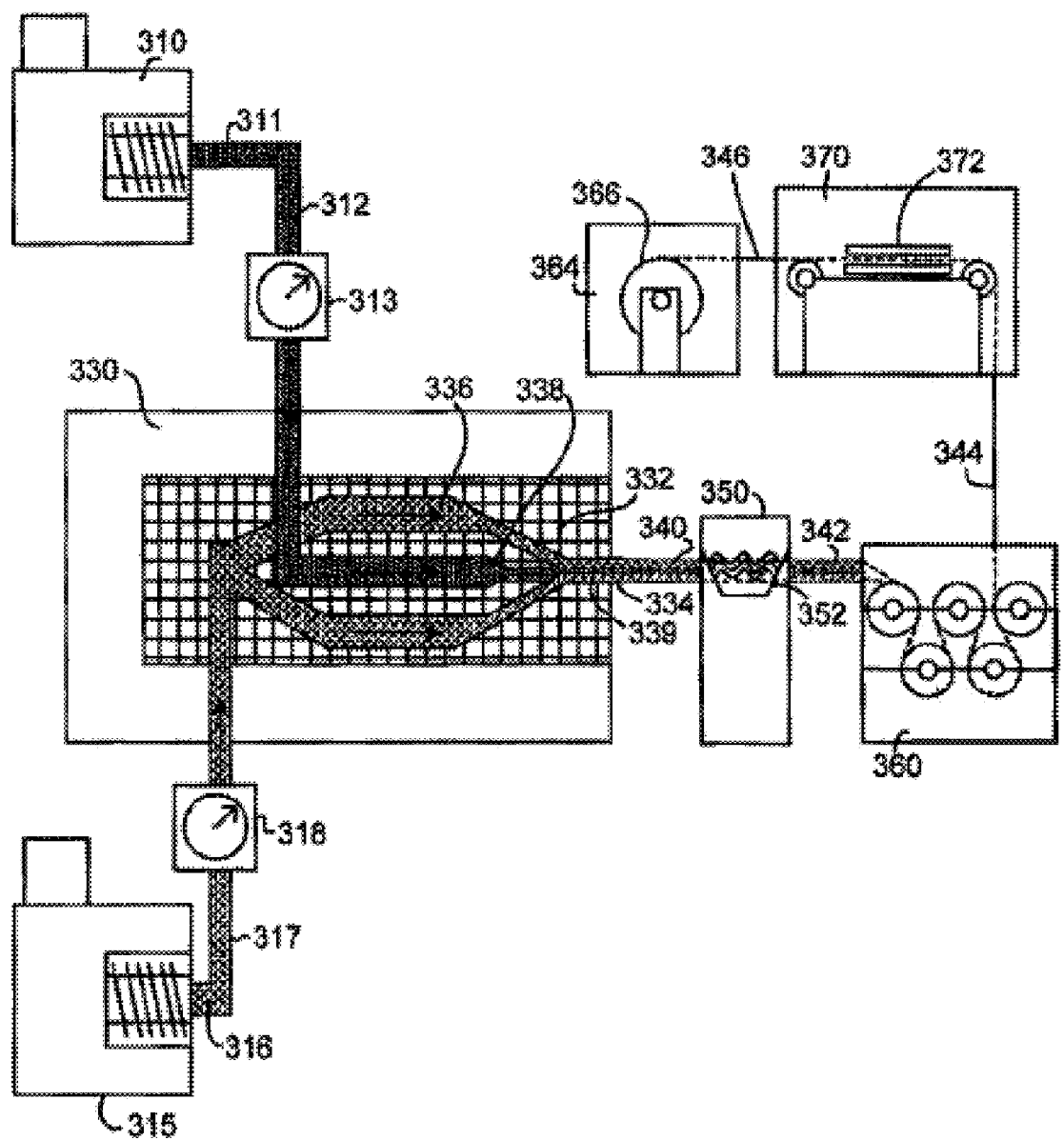
FIG. 3A illustrates a method and apparatus for co-extruding multiple materials to form a composite filament suitable for creation of a self-retaining suture comprising a drug according to an embodiment of the present invention.

In accordance with one embodiment of the invention including heat-stable drug(s), a monofilament 346 is formed by co-extruding two materials. As shown in FIG. 3A, satellite extruder 310 heats, melts and extrudes a first material 311 along conduit 312 to main extruder 330. Metering pump 313 on conduit 312 controls the flow of first material 311 to main extruder 330. A second satellite extruder 315 heats, melts and extrudes a second material 316 along conduit 317 to main extruder 330. Metering pump 318 on conduit 317 controls the flow of second material 316 to main extruder 330.

In main extruder 330, the two melted materials 311, 316 flow through two flow paths 336, 338 through an extrusion die 332 which controls the arrangement of the two materials 311, 316 when the materials combine in flow channel 339. The two materials may contain different concentrations of a drug. The two materials are combined in flow channel 339 as shown and then extruded from die 332 through die exit 334. Die 332 and flow channels 336, 338, 339 are designed and operated such that the two materials 311 and 316 do not mix in flow channel 339. The fiber 340 which is still melted material is then solidified by air or liquid cooling in quenching station 350. Quenching station 350 optionally includes a quenching bath 352 for liquid cooling. The solidified filament 342 is then drawn in drawing machine 360. Typically the solidified filament is drawn at temperatures between 30-80% of melting point (Celsius). Usually the suture is extruded then drawn on several rollers with decreasing temperature. Drawing of the filament reduces the diameter of the filament while at the same time orienting the molecules of the polymers of the filament and enhancing the tensile strength of the filament. Typically drawing is conducted in a continuous process by winding the filament around a series of rollers where each roller in the series has a slightly higher roller surface speed. The speed differential of the rollers results in stretching of the filament as the filament passes from roller to roller. The filament may also be tempered by one or more heating and cooling steps before, during or after the drawing process. As illustrated in FIG. 3A, drawn filament 344 is tempered in tempering machine 370 as the filament is passed through heating unit 372. After the filament has been drawn and tempered the finished monofilament 346 is passed to winder 364 where the monofilament is wound onto drum 366 until required for preparation of self-retaining sutures. Where a drug is incorporated in material 311 and/or 316 before or during the manufacturing of filament 342, care must be also taken to ensure that the filament manufacturing process does not denature the drug. Alternatively, a drug is deposited on or impregnated in the filament during or after extrusion of the filament.

Figure 3B:
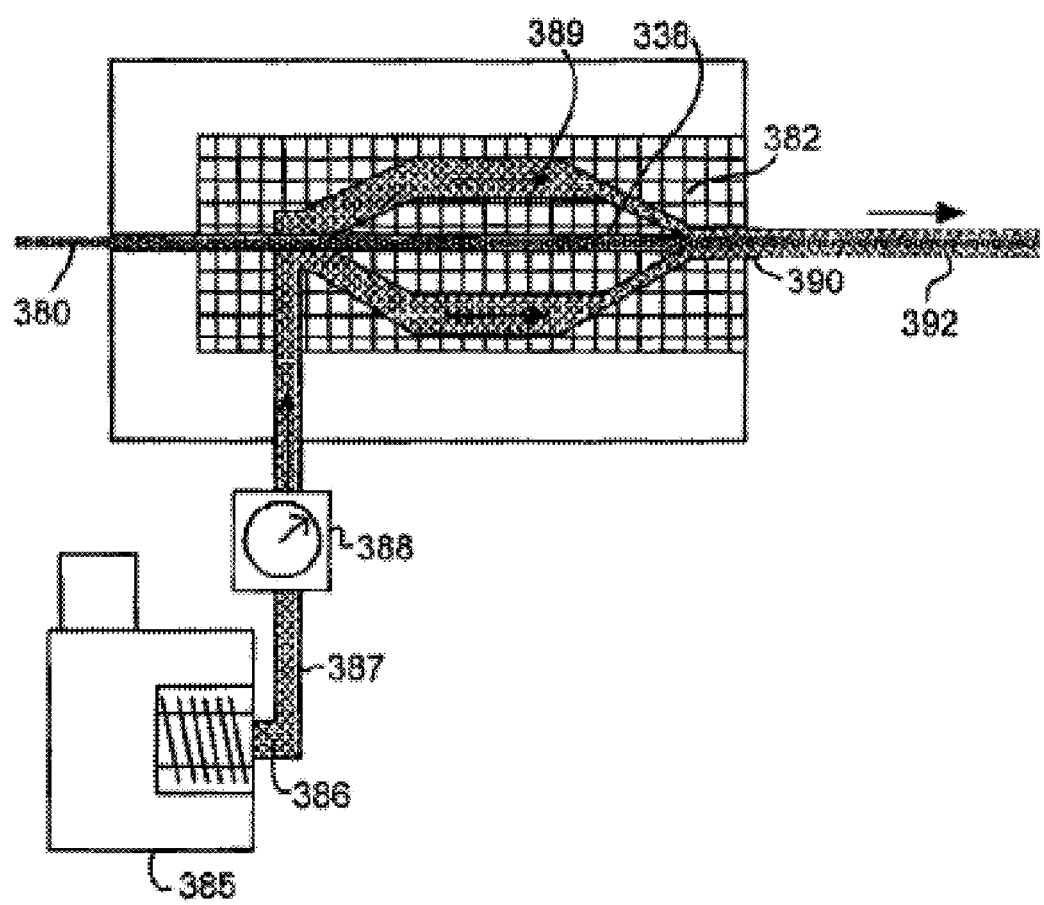
FIG. 3B illustrates a method and apparatus for extruding a material onto a preformed filament to form a composite filament suitable for creation of a self-retaining suture comprising a drug according to an embodiment of the present invention.

FIG. 3B illustrates an alternative method of making a filament suitable for use in embodiments of the present invention that include heat-stable drug(s). As shown in FIG. 3B, a core filament 380 is drawn through an extrusion die 382. Satellite extruder 385 heats, melts and extrudes a sheath material 386 via conduit 387 to die 382. Metering pump 388 controls the flow of sheath material 386 to flow path 389 of die 382. The rate of supply of sheath material 386 and the rate of movement of core filament 380 are controlled such that a sheath material 386 is evenly coated on the core filament 380 in the desired cross-section (as determined by the cross-section of the extrusion nozzle 390. A suitable method for making a filament comprising a core coated with an extruded material is described in U.S. Pat. No. 6,183,499 titled "Surgical Filament Construction" to Fisher et al. which is incorporated herein by reference. The finished filament 392 comprising core filament 380 and sheath material 386 may be quenched, tempered and drawn and then wound onto a drum as shown in FIG. 3A. However, in certain embodiments, core filament 380 may already have been drawn and no further drawing of finished filament 392 may be necessary or desirable. In some embodiments, for example, a core filament of a core material may be extruded and then drawn. Then the same material may be extruded over the core filament (as shown in FIG. 3B) without subsequent drawing of the filament. The resulting filament has a core and sheath of the same material, however, the sheath material has different physical properties than the core material because the sheath material has not undergone the drawing process. Where a drug is incorporated in material 380 and/or 386 before or during the manufacturing of filament 392, care must be taken to ensure that the filament manufacturing process does not denature the drug.

In another embodiment, the materials may be spun into fibers to be used as monofilament or multifilament sutures. To produce fibers having the core/sheath structure of FIG. 1, the core and sheath constituent materials are separately melted. The constituent materials are separately fed as polymer melts to a spinneret and are combined in the spinneret just before the spinneret exit orifice. The spinning device may have one or a plurality of spinnerets. The filament produced from a spinneret undergoes subsequent processing such as quenching, drawing and tempering in order to produces a filament suitable for use in embodiments of the present invention. Particular apparatus and methods for forming monofilaments suitable for use in the present invention can be found in U.S. Pat. No. 7,070,610 titled "Monofilament Suture And Manufacturing Method Thereof" to Im et al. and U.S. Pat. No. 6,315,788 titled "Materials And Surgical Articles Made Therefrom" to Roby, both of which are incorporated herein by reference. Although extrusion has been illustrated in FIGS. 3A and 3B, any suitable manufacturing process may be used to form the filaments utilized as a stock filament material for embodiments of self-retaining sutures of the present invention.

Figure 3C:
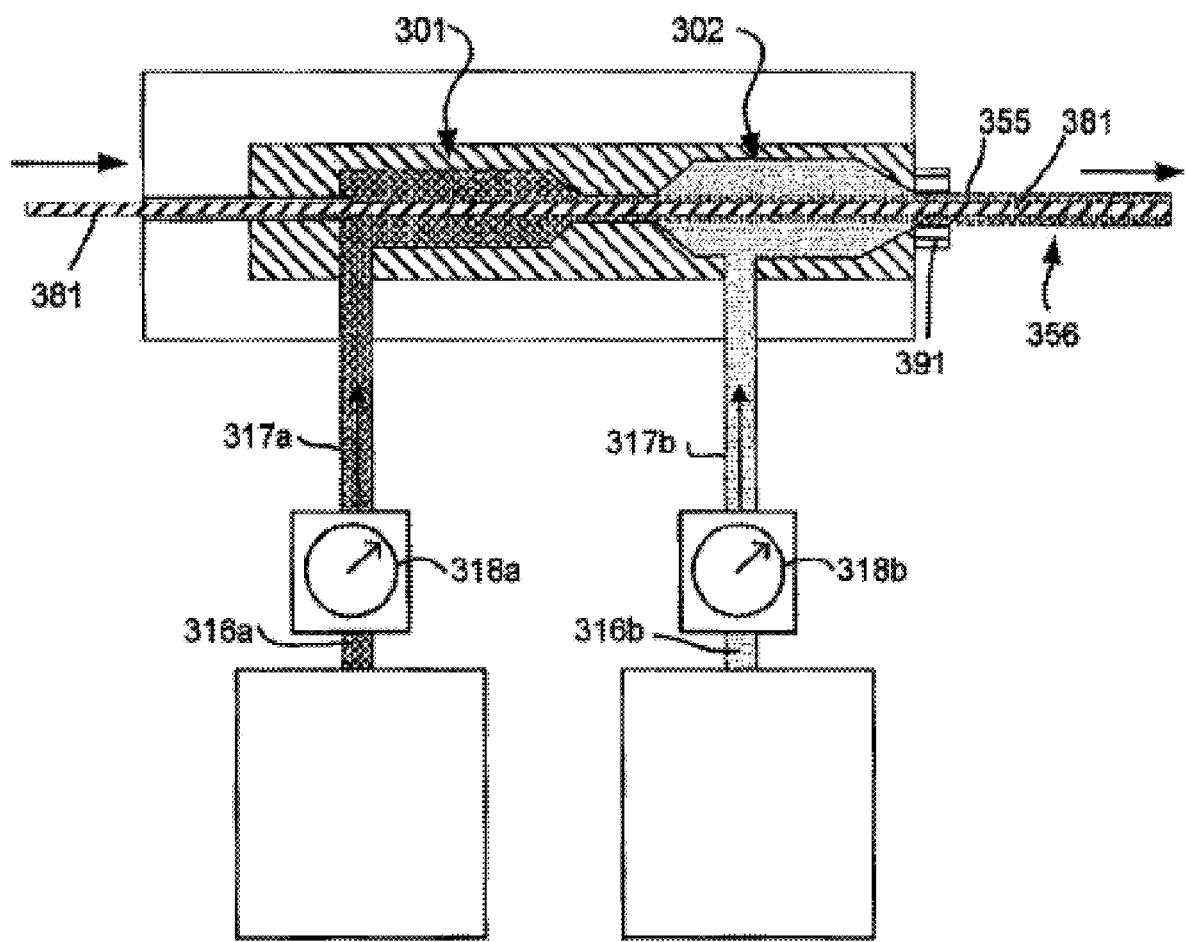
FIG. 3C illustrates an alternative method and apparatus for depositing a material onto a preformed filament to form a composite filament suitable for creation of a self-retaining suture comprising a drug according to an embodiment of the present invention.

In embodiments in which the drug is not heat stable, other methods of manufacturing the filament may be used to achieve the same "core/sheath" or "over the filament" arrangements. Such methods include those described in U.S. Pat. No. 6,596,296 (TissueGen, Inc., Dallas, Tex.), which is incorporated by reference herein. In accordance with one such embodiment of the invention, a sheath is applied to a braided core or woven core. FIG. 3C illustrates one method by which the coating may be achieved. As shown in FIG. 3C, a polymer precursor supply device 300 supplies a polymer precursor 316a along conduit 317a to coating chamber 301. Metering pump 318a on conduit 317a controls the flow of polymer precursor 31 a to coating chamber 301. A preformed braided core 381 is drawn through coating chamber 301 where it is coated polymer precursor 316a. The rate of supply of sheath polymer precursor 316a and the rate of movement of braided core 381 are controlled so that polymer precursor 316a is evenly coated on the core 381. The braided core 381 coated with polymer precursor 316a passes from the coating chamber 301 into the polymerization chamber 302.

As shown in FIG. 3C, a polymerization agent supply device supplies a polymerization agent 316b along conduit 317b to polymerization chamber 302. Metering pump 318b on conduit 317b controls the flow of polymerization agent 316b to polymerization chamber 302. The preformed braided core 381 is drawn through polymerization chamber 301 the coating of polymer precursor 316a comes into contact with polymerization agent 316b and is caused to polymerize—beginning with the surface. The rate of supply of polymerization agent 316b and the rate of movement of braided core 381 are controlled so that polymer precursor 316a is evenly polymerized on the core 381. The braided core 381 coated with a polymer sheath 355 passes from the polymerization chamber 302 into the polymerization chamber 302 through nozzle 391 which guides the configuration of the polymer sheath. The finished suture 356 with braided core 381 and polymer sheath 355 may be subjected to suitable post processing and then wound onto a drum until it is ready for forming tissue retainers.

In certain embodiments, it may not be necessary or desirable to draw finished suture 356 after forming the polymer sheath 355. In some embodiments, for example, fibers for making a braided core 381 are extruded and drawn and the fibers are subsequently braided to form braided core 381. The braided core 381 cannot be drawn any further. Polymer sheath 355 is then deposited over the braided core 381 (as shown in FIG. 3C). However the finished suture 356 is not drawn after deposition of the polymer sheath 355. In some embodiments, the polymer sheath 355 may be the same polymer as the braided core 381 but have different physical properties because of the differing treatment (i.e. the braided core has different physical properties than the polymer sheath because the core fibers were drawn before braiding and the sheath material was not drawn after polymerization.

In some embodiments, a drug is associated with the polymer sheath 355 during the coating and polymerization step. In other embodiments a drug is associated with the braided core 381 before or after manufacture of braided core 381 and before deposition of polymer sheath 355. For example, a drug may be associated with braided core 381 by dipping the braided core into a solution including the drug and allowing the solution to diffuse into the braided core. Subsequently a polymer sheath 355 is deposited trapping the drug inside the braided core 381 until implantation and release of the drug through the polymer sheath. In other embodiments a drug is associated with each of braided core 381 and polymer sheath 355.

Many different braided threads and or sutures may be used as the braided core 381 of a self-retaining braided suture in accordance with embodiments of the present invention. For example, core 381 may be a conventional braided suture material. For example, braided sutures such as VICRYL™, SURGICRYL™ BIOVEK™, VISORB™, POLYSORB™, SURGISORB™, and DEXON™ may be provided with a biodegradable sheath suitable for the formation of retainers and the resulting self-retaining braided suture will be useful in applications where it is desirable to have a self-retaining absorbable suture which retains its tensile strength for a period of three to four weeks and is completely absorbed by hydrolysis in a period of ten weeks. These sutures are manufactured using braided polyglycolic acid (PGA) material and may be coated with a polymer sheath into which retainers may be cut. Retainers may be formed in the sheath layer to create self-retaining braided sutures in accordance with embodiments of the present invention.

In another example braided sutures such as ARTHREX™ FIBERWIRE™ may be provided with a nonbiodegradable sheath suitable for the formation of retainers and the resulting self-retaining braided suture will be useful in applications where a strong non-absorbable suture is desired. FIBERWIRE™ includes a blend of an ultra-high molecular weight polyethylene multi-filament core with a braided polyester jacket and may be coated with extruded polyester into which retainers may be cut. Retainers may be formed in the sheath layer to create self-retaining braided sutures in accordance with embodiments of the present invention. Substantial retainers may be provided suitable for engaging soft tissue to approximate e.g. tissue to bone. The retainers are designed to be effective to engage the intended tissues, for example tough tissues, fascia, capsule, meniscus-like structures, glenoid labrium in shoulder, flexor tendons, tendons, rotator cuffs. Typically the suture will tether such tissues to bone or periosteum. Thus, the braided suture may include a suture loop of anchoring device at one end to engage a bone tunnel, bone, periosteum or another stable anatomical feature. Such braided sutures may be used in arthroscopic applications where a strong non-absorbable self-retaining braided suture is desired.

Filament Configurations

Depending upon the configuration of the extruders, die, spin block, spinneret, or other manufacturing equipment, a filament suitable for creating a drug-eluting self-retaining suture according to embodiments of the present invention can be created with a wide variety of different arrangements of different materials. Furthermore, filaments can be made using two, three, four or even more different component materials and/or two, three, four or even more different drugs or drug concentrations if necessary or desired for the particular application. Different configurations of filaments are useful in specific embodiments of the present invention and are described below with respect to FIGS. 3D-3F and 4A-4I. The arrangement of materials and drugs or drug concentrations in the filament may be used to control the release kinetics of the drug or drugs contained within the filament. The release kinetics are affected by the surface area of retainers in a particular region and thus should be validated for particular retainer configurations to achieve the desired final kinetics.

Figure 3D:
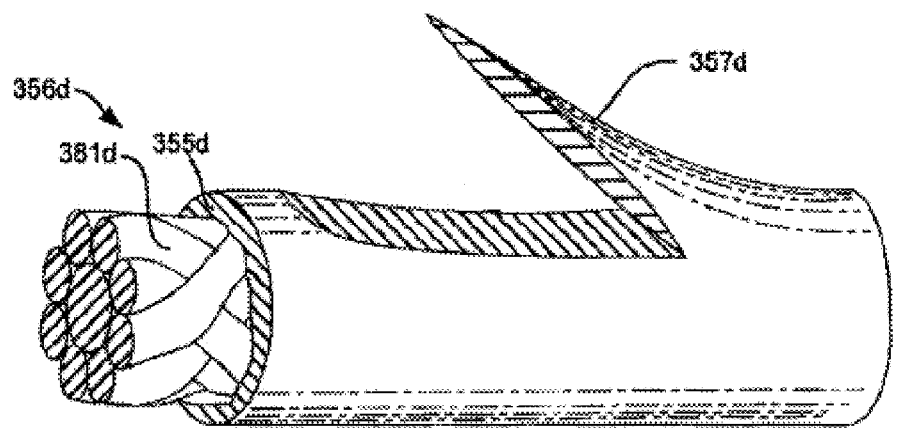
FIGS. 3D-3F illustrate alternative configurations of self-retaining filaments and structures suitable for creation of a self-retaining suture comprising a drug according to embodiments of the present invention.

FIG. 3D, shows a perspective and sectional view of a drug-eluting self-retaining suture 356d having a braided core 381d and a polymer sheath 355d. Braided suture 356d may be formed by any method known in the art for making a braided suture having a sheath over a braided core each having the properties and drug content required for the function of the material in the suture fiber or thread. One suitable method is extrusion or deposition of material over a preformed braided core as previously described. Other methods of forming a sheath on a preformed braid may also be utilized including, without limitation, dip coating, spray coating, curtain coating and/or chemical deposition (for example, chemical vapor deposition CVD).

As shown in FIG. 3D a retainer 357d is formed on drug-eluting self-retaining suture 356d by e.g. making a cut 358d into the sheath 355d. The retainer 357d can be made using any of a wide range of technologies as discussed above. The depth of cut may be selected such that cut 358d is entirely within material of sheath 355d, as shown in FIG. 3D, and does not penetrate into braided core 381d. The cut depth selected is a compromise between retainer strength and tensile strength of the suture. A cut 358d too deep may cause the suture to be reduced in strength and a cut 358d that is too shallow may cause the retainer not to be strong enough to effectively engage tissue. Generally the cut depth will be selected to be from 10% to 50% of the diameter of the braided suture. The cut depth may be from 20% to 30% of the diameter of the braided suture.

In a braided suture 356d as shown in FIG. 3D, a primary contribution to the tensile strength of the suture is the tensile strength of the core 381d. Thus, the depth of cut is preferably selected so as not to cut into the core 381d. The thickness of the sheath may be increased or decreased to enable cuts 358d having a greater or lesser depth. The selection of the depth of the sheath should be made to allow the resulting retainers to be sufficiently strong so as to effectively engage the tissue. Additionally, a strong core 381d may allow sheath 355d to bear less of the load of the self-retaining suture 356d, thus allowing use of drug-eluting materials for sheath 355d which otherwise might not be sufficiently strong for manufacturing a suture. In some cases, the depth of the cut used to form a retainer may be selected so that the depth of cut is approximately equal to the depth of the sheath layer. In such cases, the resulting braided self-retaining suture will depend for its tensile strength entirely upon the tensile strength of the core.

Figure 3E:
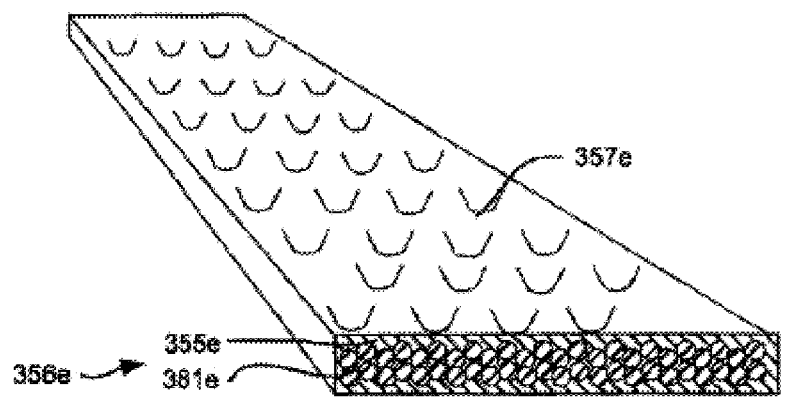
Figure 3F:
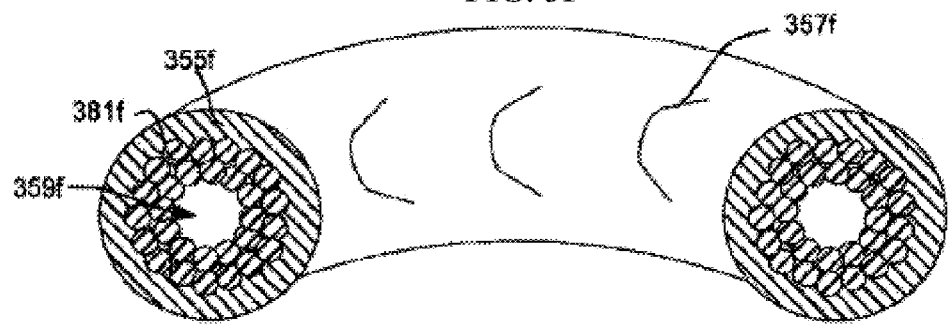

As shown in FIGS. 3E and 3F, filaments may be formed into shapes other than round surgical suture threads. For example, in the embodiment of FIG. 3E, fibers are woven into a two dimensional structure such as a flat ribbon or sheet. FIG. 3E shows a flat ribbon 381e comprising a plurality of braided fibers. Flat ribbon 381e has a sheath 355e deposited over it into which a plurality of retainers 357e have been formed. The drug-eluting self-retaining ribbon 356e may be particularly useful for supporting tissues and/or closing openings in tissue. One or more drugs may be incorporated into flat ribbon 381e and/or sheath 355e and or coated on drug-eluting self-retaining ribbon 356e. The drug-eluting self-retaining ribbon 356e may then provide those drugs to tissues in which the drug-eluting self-retaining ribbon 356e is implanted.

As shown in FIG. 3F, fibers may also be woven into 3-dimensional structure such as rings or tubes. FIG. 3F shows a circular braided tube 381f comprising a plurality of fibers braided together. Braided tube 381f has a sheath 355f deposited over it into which a plurality of retainers 357f have been formed. The drug-eluting self-retaining tube 357f may be particularly useful for supporting tissues and/or surrounding openings in tissue in particular applications. Particular 3-dimensional structures may be woven or braided to suit a particular application. One or more drugs may be incorporated into braided tube 381f and/or sheath 355f and or coated on drug-eluting self-retaining tube 357f. In addition, one or more drugs may be used to fill the lumen 359f of drug-eluting self-retaining tube 357f in a liquid, gel, or solid carrier. The drug-eluting self-retaining tube 357f may then provide drugs from the sheath 355f, braided tube 381f or lumen 359f to tissues in which the drug-eluting self-retaining tube 357f is implanted.

Figure 4A:
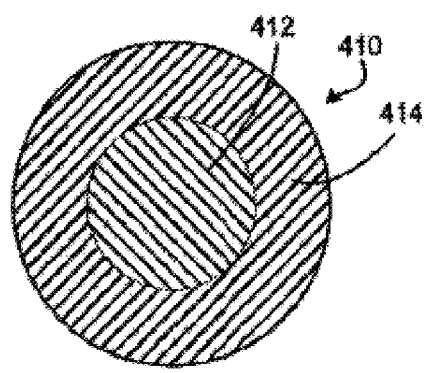
FIGS. 4A-4E illustrate alternative configurations of co-extruded suture stock suitable for creation of a self-retaining suture comprising a drug according to embodiments of the present invention.
Figure 4B:
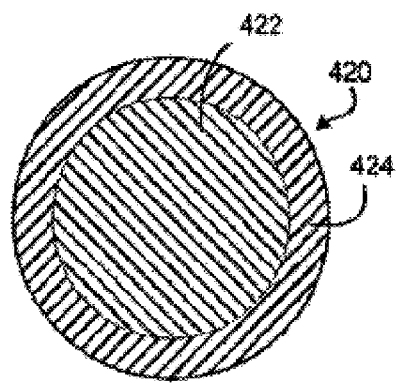

As shown in FIGS. 4A and 4B, simple filaments 410, 420 comprise two materials arranged one material in the core and a second material as a sheath over the core. This arrangement of materials in a filament can be made by co-extrusion of the two materials. The materials may be same polymer but have different concentrations of a drug or drugs. In a simple variation, the two materials may be used in different amounts depending on the use to which the filament will be put. For example in FIG. 4A, the core material 412 takes up about 25% of the cross-sectional area of filament 410, with the sheath material 414 taking up 75% of the cross-sectional area. In comparison in FIG. 4B, the core material 422 and sheath material 424 each take up about 50% of the cross-sectional area. In general, the core material may comprise from 10% to 90% of the total cross-sectional area of the filament. Preferably the core material will comprise from 25% to 90% of the total cross-sectional area of the filament. More preferably, the core material will comprise more than 50% of the total cross-sectional area of the filament. The configuration of the materials in the filament will depend upon the characteristics of the materials and the amount of material necessary to fulfill the role of the filament and attain the desired release kinetics for any drug or drugs incorporated in the filament. The release kinetics are affected by the surface area of retainers in a particular region and thus should be validated for particular retainer configurations to achieve the desired final kinetics.

Figure 4C:
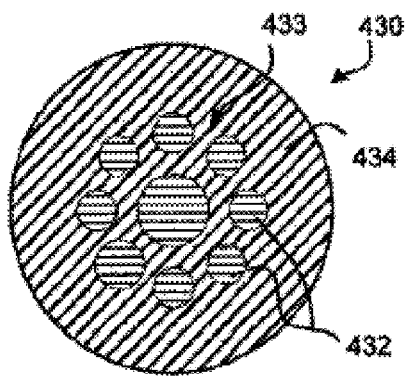

FIG. 4C illustrates an alternative filament 430 in which a plurality of "islands" 432 are present in a surrounding "sea" 434 of the second material. The plurality of islands 432 together comprise a segmented core 433 of filament 430. The "sea" 434 of the second material comprises the sheath and also fills the interstices between the segments 432 of the segmented core 433. The materials may be same polymer but have different concentrations of a drug or drugs. This arrangement of materials in a filament 430 can be made by co-extrusion of the two materials. The resulting fiber may show a useful combination of the characteristics of the materials. Particular configurations of monofilaments can be found in U.S. Pat. No. 7,070,610 titled "Monofilament Suture And Manufacturing Method Thereof" to Im et al., which is incorporated herein by reference, as well as in the aforementioned U.S. Pat. No. 7,033,603.

Figure 4D:
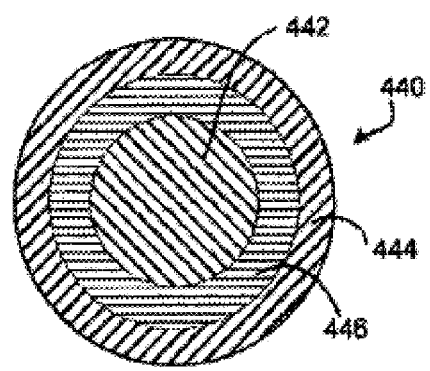

FIG. 4D illustrates another alternative filament 440 for use in the present invention. The filament of FIG. 4D is made from three different materials. A first material forms a core 442 of filament 440. A second material 444 forms a sheath on the outer surface of filament 442. The third material is sandwiched between the core 440 and the sheath 444 in intermediate layer 446. The materials may be same polymer but have different concentrations of a drug or drugs. This arrangement of materials in a filament can be made by co-extrusion of the three materials. The material of intermediate layer 446 may be selected, for example, for its mechanical properties as an interface between the core 442 and sheath 444. Alternatively the material of intermediate layer 446 may be selected for favorable interaction with tissues in the retainers as the material of intermediate layer 446 will only be exposed to the tissue where retainers are cut into filament 440. For example, the material of intermediate layer 446 may comprise an adhesive component, a therapeutic component or a material that promotes tissue adherence to the retainer or promotes wound healing as described below.

Figure 4E:
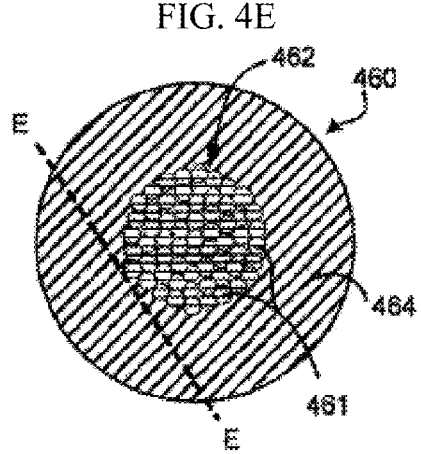

FIG. 4E illustrates another alternative embodiment in which the core 462 of filament 460 comprises a plurality of fibers 461 braided together. Core 460 is surrounded by a sheath 464. The materials may be same polymer but have different concentrations of a drug or drugs. This filament may be prepared by taking a braided thread (such as braided suture) and extruding the sheath onto the braided thread as it is passed through an extrusion die. In this embodiment the braided thread may be dipped in a solution of the drug prior to extrusion of the sheath 464. During dipping the drug will migrate into the braided thread. Note that, as before, sheath 464 is sufficiently thick that creating retainers in the surface of filament 460 does not cut into core 462 or fibers 461 of core 462. For example, the maximum depth of a straight cut for a retainer is illustrated by dashed line E-E. Thus core 462 and the material of its fibers 461 may be engineered for high tensile strength and flexibility while sheath 464 is selected based upon it ability to form, elevate and deploy retainers. A suitable method for making a filament comprising a braided core is described in U.S. Pat. No. 6,183,499 titled "Surgical Filament Construction" to Fisher et al. which is incorporated herein by reference.

Figure 4F:
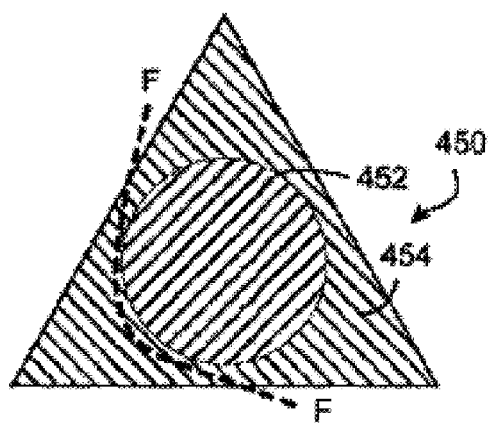
FIGS. 4F-4I illustrate alternative geometries of co-extruded suture stock suitable for creation of a self-retaining suture comprising a drug according to embodiments of the present invention.

FIG. 4F illustrates an alternative embodiment in which the core and sheaths of filament 450 have different shapes. In the embodiment of FIG. 4F, core 452 has a circular cross-section while the sheath 454 has a triangular cross-section. This arrangement provides a greater volume of the second material at the apices of the triangle while still allowing the core material to provide a high percentage of the total cross-section of the filament. The materials may be same polymer but have different concentrations of a drug or drugs. In this embodiment, the retainers are cut into the apices of the triangular cross section thus making optimal use of the material in the sheath 454. In addition, the retainer configuration may be selected such that retainers with arcuate bases are cut into the apices of the triangle. Dashed line F-F illustrates the cut for an arcuate base of a retainer and illustrates that the cut extends through a greater amount of the sheath 454 than would a straight cut. Methods for making self-retaining suture from filaments with triangular or other polyhedral cross-section are disclosed in U.S. Pat. No. 5,342,376 titled "Inserting Device For A Barbed Tissue Connector" to Ruff which is incorporated herein by reference. The arrangement of materials in a filament shown in FIG. 4F can be made by co-extrusion of the two materials. The extruder nozzle is selected to have the desired shape. The shape of the cross-section of the filament matches the shape of the extruder nozzle. Alternatively, the filament may be formed as in FIG. 4A and then the sheath material 454 may be formed into the triangular shape by post-extrusion manipulations, such as using rollers to pinch the material into shape and then heating to anneal the polymer into the chosen shape prior to creation of the retainers.

Figure 4G:
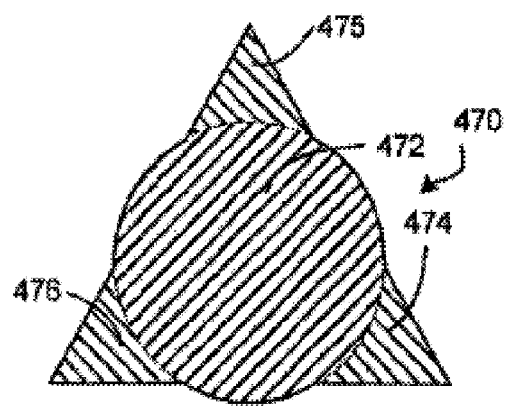
Figure 4H:
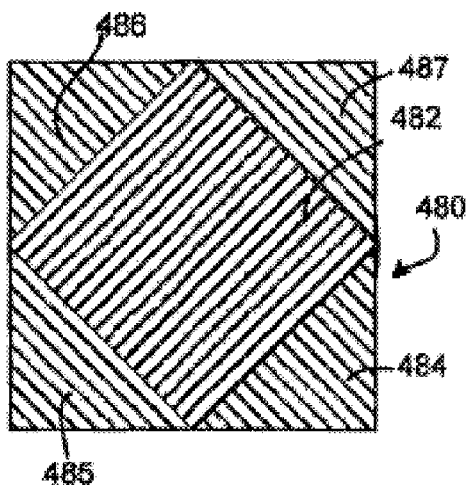
Figure 4I:
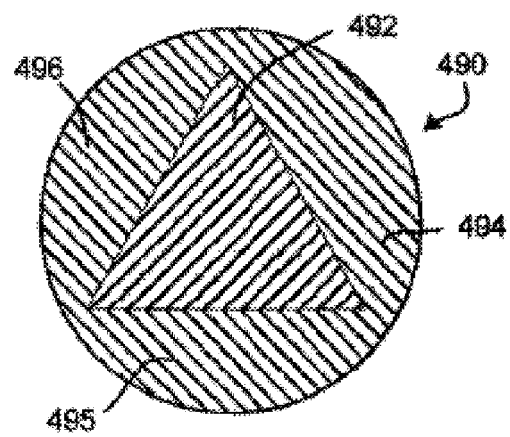

Naturally, other geometric arrangements of the materials are possible, for example the sheath may be formed with a square cross-section, pentagonal, hexagonal or other polygonal cross-section. FIG. 4G illustrates a filament 470 having a sheath comprising three segments 474, 475, 476 over a circular core 472. In this embodiment the sheath is not continuous but comprised of three elements arrayed around core 472. In this embodiment, the retainers are cut into the apices of the sheath segments 474, 475, 476 thus making optimal use of the sheath material for making retainers and providing for a large cross-section of core 472. FIG. 4H illustrates a filament 480 having a square sheath comprising four segments 484, 485, 486, 487 over a square core 482. In this embodiment, the retainers are cut into the apices of the sheath segments 484, 485, 486, 487 thus making optimal use of the material in the sheath and providing for a large cross-section of core 482. FIG. 4I illustrates a filament 490 having a circular cross-section wherein the core 492 has a triangular cross-section. In this embodiment, the retainers are preferably cut into the thicker portions of the sheath 494, 495, 496. The materials may be same polymer but have different concentrations of a drug or drugs.

Retainer Cutting Blades, Retainers and Retainer Distribution

Figure 5A:
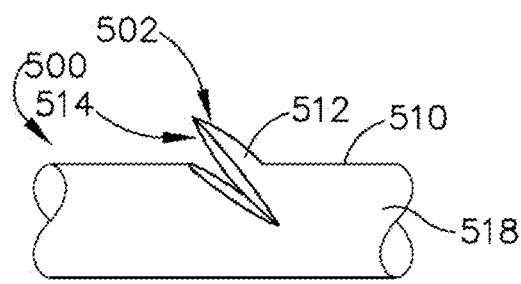
FIGS. 5A-5C illustrate particular embodiments of retainers for creation of a self-retaining suture comprising a drug according to embodiments of the present invention.
Figure 5B:
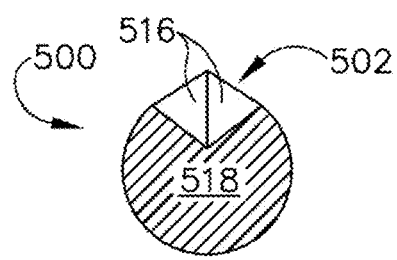
Figure 5C:
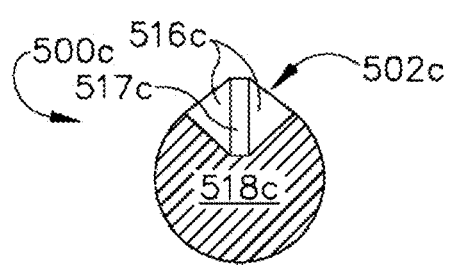

Referring to FIGS. 5A and 5B, an embodiment of a self-retaining suture 500 according to the present invention can include a retainer 502 with an upper surface 512 extending from a periphery 510 of the filament 518 and a lower surface 514 having at least two facets 516. As seen in the front view of FIG. 5B, the retainer can have a roughly pie-slice (i.e., wedge) shape. The increased cross-section moment of inertia (also known as the second moment of area) of the retainer improves strength, and can improve resistance to the tendency of a retainer to fold back on itself and yield to movement of the suture through the tissue, as described above. This retainer further reduces stress concentrations along the lower surface of the retainer and the suture when compared with the retainers of FIG. 2A-2C made with a straight cut. The retainer need not be shaped as a perfect wedge, but rather preferably has at least two facets to improve resistance to back bending. Thus, for example the retainer may have a roughly trapezoidal shape, with three facets. FIG. 5C shows a self-retaining suture 500c having an alternative retainer 502c having two facets 516c and between them an uncut strand 517c connecting retainer 502c to filament 518c. Strand 517c serves to stabilize the elevation of retainer 502c thereby enhancing tissue engagement by retainer 502c in certain applications.

Figure 5D:
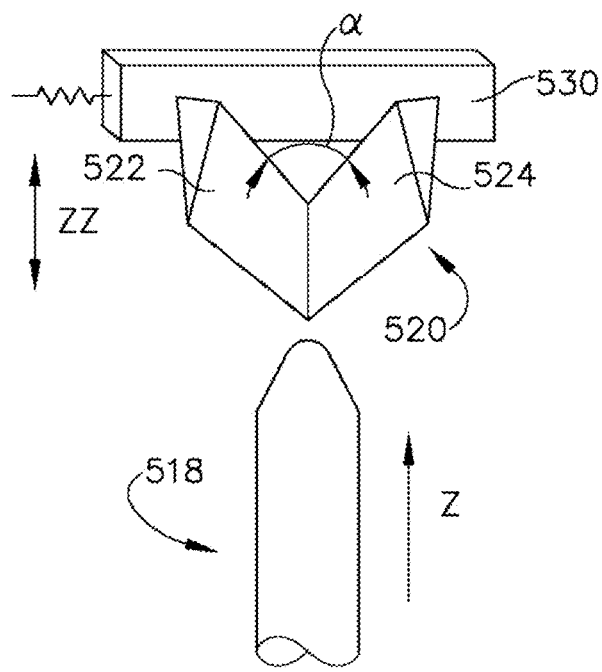
FIG. 5D illustrates a sapphire blade configuration for cutting the retainers of FIGS. 5A-5C according to an embodiment of the present invention.

Referring to FIG. 5D, an embodiment of a mechanism of forming a retainer 502 in a filament 518 such as shown in FIGS. 5A and 5B is illustrated. A V-shaped cutting edge 520 includes two blades 522, 524 arranged in proximity to form a desired cutting angle α and resembling a V. In a preferred embodiment, the blades 522, 524 are placed close to each other at a cutting angle α of 90°. In alternative embodiments the blades 522, 524 can be arranged to form an obtuse or acute angle where desired. In other embodiments the V-shaped blade can have any of its surfaces be convex or concave to allow for the selection of an appropriate final retainer design, either maximizing the moment of inertia of the retainer 502 or the remaining cross sectional area of the filament 518. The cutting edge 520 can be temperature controlled to ensure a blade temperature suitable for forming retainer 502 without denaturing any drug coated on or impregnated in the filament 518.

In a preferred embodiment, the blades 522, 524 of cutting edge 520 are sapphire blades. Sapphire blades are ceramic blades typically having an edge radius one or two magnitudes lower than an edge radius of a steel blade thus allowing the accurate cutting of retainers on filaments of size USP 6-0, 8-0 and smaller. Further, sapphire blades generally maintain their mechanical characteristics over the temperature ranges desirable for cutting polymer and co-polymer materials. Maintaining mechanical characteristics (i.e., geometry of a cut produced) can be desired where the retainers are extremely small and therefore sensitive to small changes. Further, sapphire blades are more abrasion resistant than, for example, typical steel blades, providing more repeatable results over long term use. Further, sapphire blades can be sharpened more effectively than steel blades. In alternative embodiments, blades 522, 524 may be metal, mineral or ceramic blades which are hard coated, mineral coated, ceramic coated and/or carbon coated blades. For example, the blades may have: carbon coating, diamond coating, diamond-like coating, nano-ceramic coating, ceramic coating, sapphire coating and/or yttriated zirconia coating or a ceramic material having the desired sharpness and durability or other hardened blades or hard coated blades.

Filament 518 can be spooled or otherwise fed or drawn in a direction z after extrusion at a generally constant speed, in a twisting or non-twisting path. In alternative embodiments the speed may be controlled to control the distribution—lower speed resulting in a higher retainer density and higher speeds resulting in a lower retainer density. For manufacturing a one-direction retainer suture, a cutting edge 520 can be arranged in each of four quadrants of a circle. The sapphire blades oscillate in a direction z so that the cutting edge 520 alternately penetrates the suture 520 and pulls away from a cut. The cutting edge can be oscillated by a cam device, for example. The oscillation thus creates an arrangement of retainers along filament 518 as filament 518 is fed in the z-direction. For manufacturing a two-direction retainer suture, a cutting edge can be arranged in each of four quadrants of a circle in each of two directions of protrusion/penetration, resulting in eight cutting edges. The cutting edge can comprise the sapphire blades that oscillate so that the cutting edge alternately penetrates the suture and pulls away from the cut.

Alternative embodiments of mechanisms for forming retainers in filaments can be used to generate retainer arrangements. For example, a cutting edge can be arranged in each of three zones to form retainers extending from three circumferential locations along the suture. Further, one or more of the cutting edge and the filament can be rotated around the long axis of the filament 120 as the filament is drawn in the z direction so that the retainers are arranged in a helical fashion along the suture. Furthermore, the oscillation of the cutting edge may be increased in frequency or decreased in frequency or stopped altogether in order to increase or decrease the density of retainers or stop retainer formation in a particular self-retaining suture or region of an self-retaining suture. Retainer patterns can be formed to suit a surgical or cosmetic procedure or application, and the properties of the material at the location of the procedure or application. As stated above, retainer patterns may also be selected to tailor the surface area of the filament available for elution of a drug in order to achieve the desired release kinetics for the drug in the resulting self-retaining suture or region of a self-retaining suture.

In particular embodiments, the cutting edge 520 is temperature-controlled to optimize formation and elevation of the retainer 502 while preserving the activity of any drug coated on or impregnated in the filament 518. To control the temperature of the cutting edge 520, the sapphire blades are mounted or otherwise place in conductive communication with a temperature-controlled copper plate 530. The copper plate 530 can effectively heat or cool the cutting edge 520 to the desired temperature through conduction. The copper plate 530 is temperature-controlled utilizing a solid state or liquid heat transport system and a closed-loop temperature controller. The temperature of the cutting edge 520 can thus be tightly controlled to a desired temperature range to provide satisfactory retainer formation while avoiding denaturing a drug coated on or impregnated in the filament 518. Furthermore, the filament 518 can also be temperature controlled prior to, during and after formation of the retainer to prevent or reduce any deleterious effects of the retainer formation upon the activity of a drug coated on or incorporated in filament 518. Furthermore, the time of contact between the cutting edge 520 and filament 518 can be modulated to reduce the extent to which the cutting blade temperature change the temperature of the filament 518 during cutting. For example, in a preferred embodiment the cutting edge 520 is in conductive proximity to the filament 518 for from four to five milliseconds during formation of a retainer 502. Thus, the effect of the cutting blade temperature is limited to a small region of the filament 518 immediately adjacent the cutting edge 520.

Figure 5E:
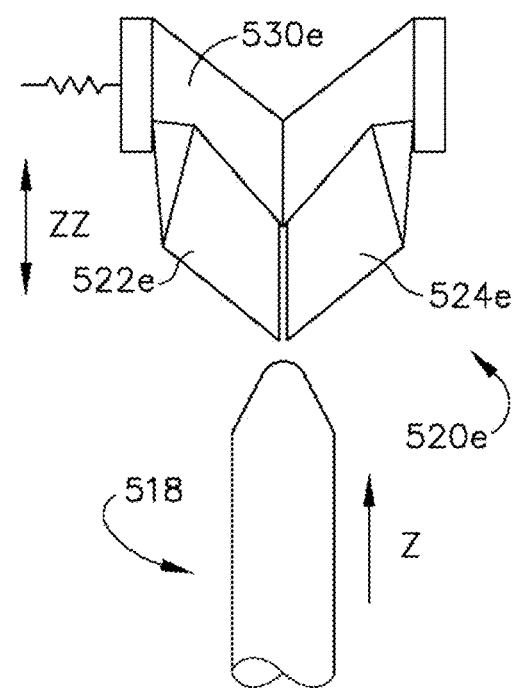
FIG. 5E illustrates an alternative sapphire blade configuration for cutting the retainers of a self-retaining suture according to embodiments of the present invention

FIG. 5E shows an alternative cutting mechanism in which the cutting edge 520e includes two sapphire blades 522e, 524e having some finite distance between the cutting surfaces, resulting in a retainer 502 resembling the retainer 502c of FIG. 5C. Further, an alternative temperature controlled copper plate 530e is shown contacting the surface of the blades 522e, 524e rather than contacting the back edge of the blades 522e, 524e.

Figure 5F:
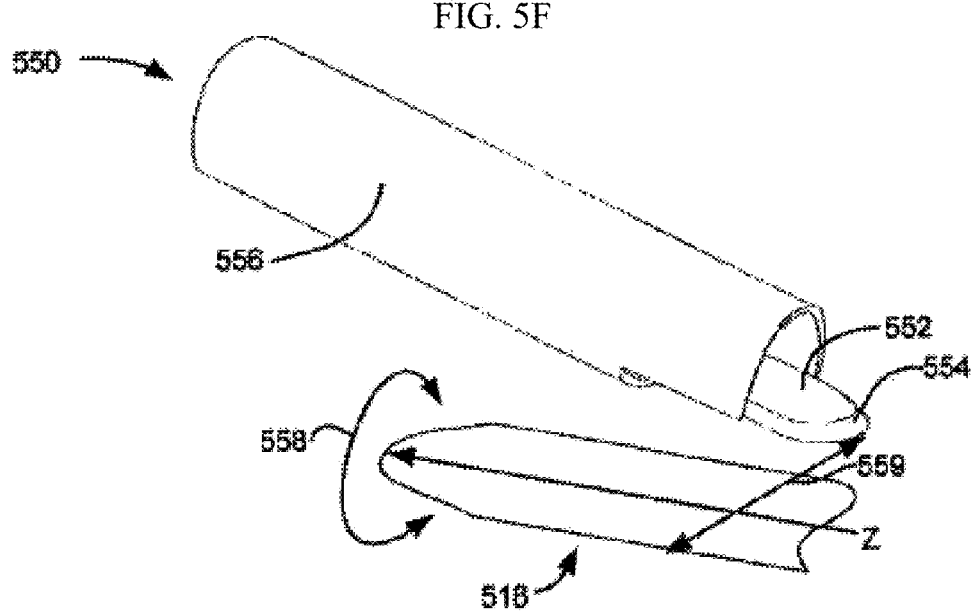
FIG. 5F illustrates a curved sapphire blade configuration for cutting the retainers of a self-retaining suture according to embodiments of the present invention.

FIG. 5F shows an alternative cutting mechanism 550 having a curved sapphire blade 552. Curved sapphire blade 552 when cutting filament 518 moves transverse (as shown by arrow 559) to the z-axis of filament 518 to cut a retainer (not shown) in filament 518. Filament 518 is moved in the direction of the z-axis to cut retainers at different positions along the filament. Filament 518 may also be rotated around the z axis as shown by arrow 558 in order to cut retainers at multiple angular positions around the z-axis. The angle of curved sapphire blade 552 and height of blade 552 relative to filament 518 is controlled to adjust the shape and size of a retainer formed by the mechanism and to ensure adequate cross-section of filament 518 remains after forming the retainer. In the cutting mechanism 550, curved sapphire blade 552 is mounted in a tube 556. Tube 556 mounts to cutting equipment in a manner that allows removal and replacement and angular adjustments of the blade 552. In the embodiment shown, curved sapphire blade 552 has a hemispherical edge tip 554. In alternative embodiments, blades of any material are straight or curved and may have be hemispherical, parabolic, or any other curve suitable for cutting the retainer. In embodiments of the present invention, sapphire blade 552 is used to cut retainers on filaments to make self-retaining sutures of USP 6-0, 8-0 and smaller.

Figure 5G:
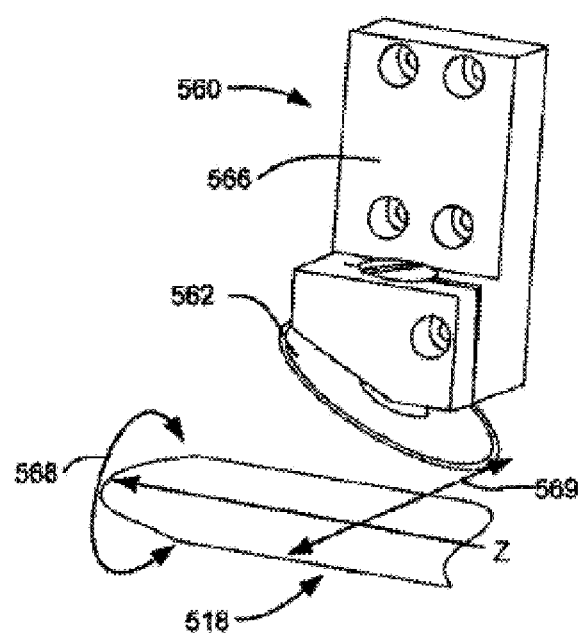
FIG. 5G illustrates a circular blade configuration for cutting the retainers of a self-retaining suture according to embodiments of the present invention.

FIG. 5G shows and alternative cutting mechanism 560 have a circular steel blade 562. Curved steel blade 562 when cutting filament 518 moves transverse (as shown by arrow 569) to the z-axis or longitudinal axis of filament 518 to cut a retainer (not shown) in filament 518. Filament 518 is moved in the direction of the z-axis to cut retainers at different positions along the filament. Filament 518 may also be rotated around the z axis as shown by arrow 568 in order to cut retainers at multiple angular positions around the z-axis. The angle of circular steel blade 562 and height of blade 562 relative to filament 518 are controlled to adjust the shape and size of a retainer formed by the mechanism and to ensure adequate cross-section of filament 518 remains after forming the retainer. In the cutting mechanism 560, curved steel blade 562 is mounted to a block 566. Block 566 mounts to cutting equipment in a manner that allows removal and replacement and angular adjustments of the blade 562.

The retainers of self-retaining suture may also be cut without a blade, for example, in an alternative embodiment of the present invention, a picosecond laser is used to ablate material to form a retainer. The laser can be optically controlled and does not need to physically contact the filament thereby allowing for very accurate shaping and placement of retainers on the filament. Other possible retainer creation techniques include EDM, wet etching, dry etching, coining, stamping and the like.

Figure 6A:
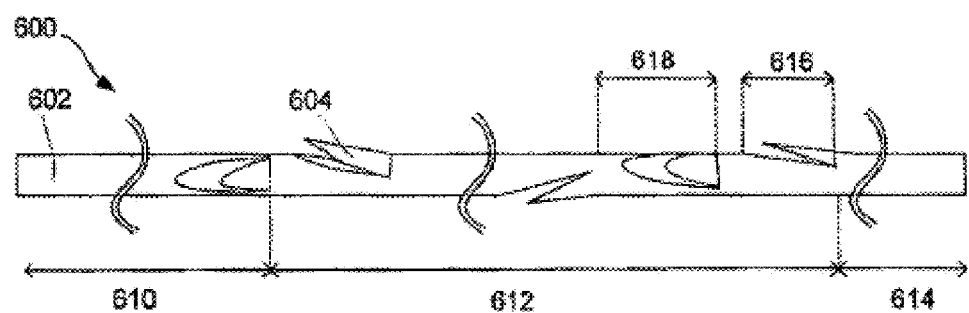
FIG. 6A illustrates a single helix distribution of retainers on a drug-eluting self-retaining suture according to an embodiment of the invention.
Figure 6B:
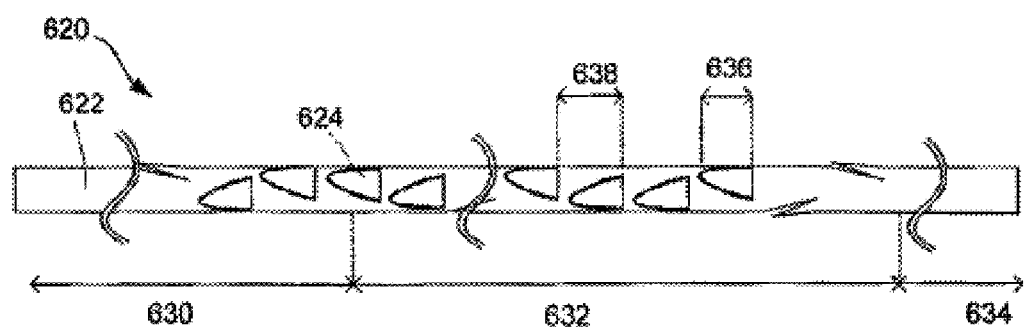
FIG. 6B illustrates a double helix distribution of retainers on a drug-eluting self-retaining suture according to an embodiment of the invention.
Figure 6C:
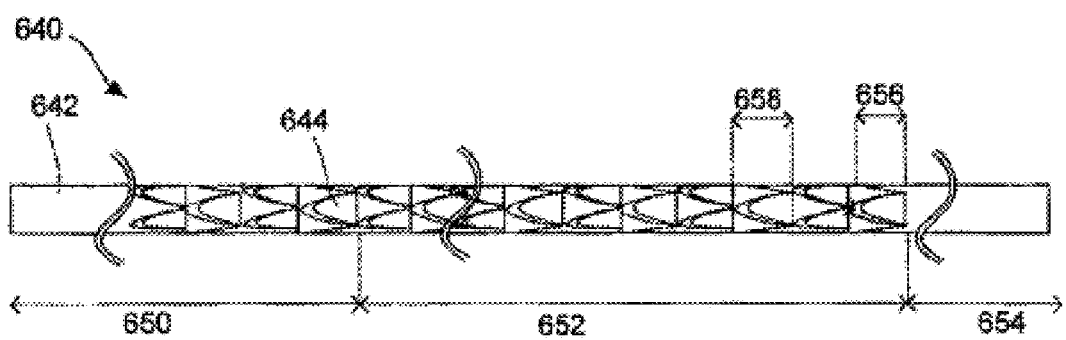
FIG. 6C illustrates a high density quad distribution of retainers on a drug-eluting self-retaining suture according to an embodiment of the invention.
Figure 6D:
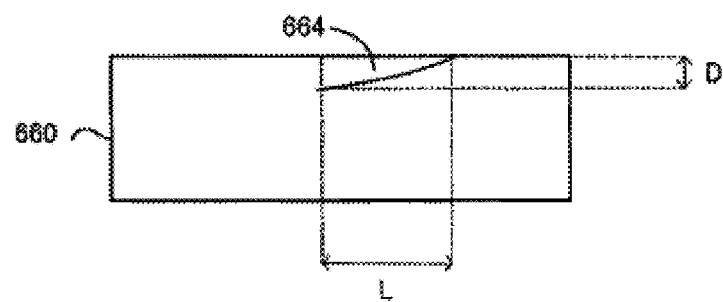
FIGS. 6D-6F illustrate alternative retainer shapes for retainers on a drug-eluting self-retaining suture according to embodiments of the invention.
Figure 6E:
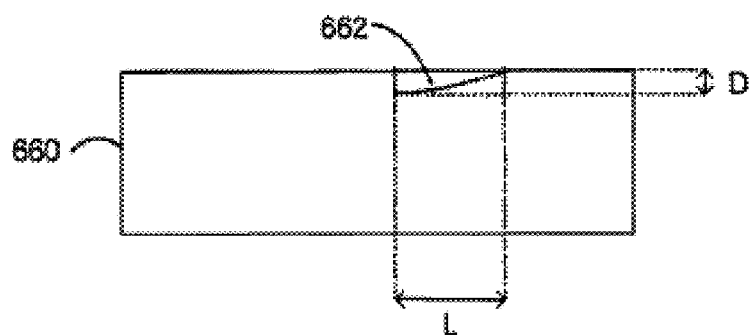
Figure 6F:
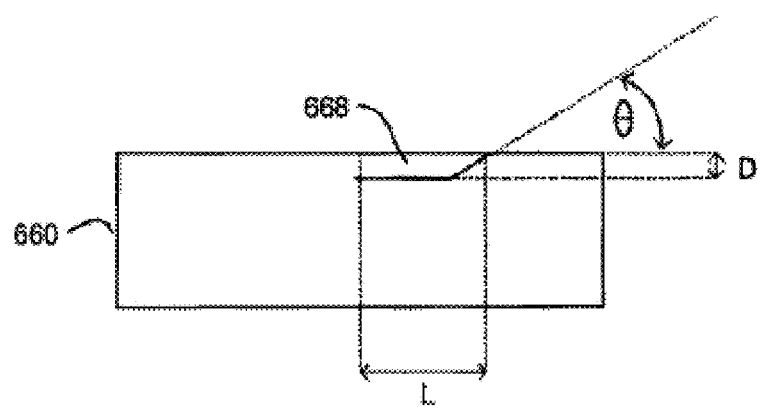

FIGS. 6A, 6B, and 6C show a range of retainer distributions and patterns that can be used in conjunction with a drug-eluting self-retaining suture. FIGS. 6D, 6E, and 6F show a range of retainer shapes that can used in conjunction with a drug-eluting self-retaining suture. FIG. 6G shows the range of suture dimensions that can benefit from the embodiments of the invention. FIG. 6A shows a single helix distribution of retainers on a drug-eluting self-retaining suture according to an embodiment of the invention. FIG. 6B shows a double helix distribution of retainers on a drug-eluting self-retaining suture according to an embodiment of the invention. FIG. 6C show a high density distribution of retainers on a drug-eluting self-retaining suture according to an embodiment of the invention.

Referring first to FIG. 6A which shows a single helix distribution of retainers 604 on a drug-eluting self-retaining suture. As shown in FIG. 6B, the self-retaining suture 620 has a filament 602 which is of USP 6-0, 7-0, 8-0, 9-0 10-0 or below. As shown in FIG. 6A, the filament is 0.25 mm in diameter which is a 4-0 suture. The self-retaining suture 600 includes a plurality of retainers 604 arranged in a helical pattern around and along the filament 602. As shown in FIG. 6A, the helix has a pitch of 4.46 mm (or 5.7 twists per inch). Each retainer is 0.5 mm from tip of depression to base of cut—measured axially—see arrow 616. The distance between the base of one retainer and the base of the adjacent retainer in the same helix 0.6 mm—measured axially—see arrow 618. In an embodiment the self-retaining suture has a barbed section 612 at least 60 mm in length and a 100 mm unbarbed lead 610, 614 on either side of the barbed section 612. The barbed section 612 may have retainers 604 in one orientation or in different orientations.

Referring now to FIG. 6B which shows a double helix distribution of retainers 624 on a drug-eluting self-retaining suture 620. As shown in FIG. 6B, the self-retaining suture 620 has a filament 622 which is of USP 6-0, 7-0, 8-0, 9-0 10-0 or below. As shown in FIG. 6B, the filament is 0.25 mm in diameter which is a 4-0 suture. The self-retaining suture 620 includes a plurality of retainers 624 arranged in a double helical pattern around and along the filament 622. As shown in FIG. 6B, each helix has a pitch of 6 mm (or 4.2 twists per inch). The helixes are shifted axially by 0.49 mm relative to one another. Each retainer is 0.31 mm from tip of depression to base of cut—measured axially—see arrow 636. The distance between the base of one retainer and the base of the adjacent retainer in the same helix 1 mm—measured axially—see arrow 638. In an embodiment the self-retaining suture has a barbed section 632 at least 100 mm in length and a 100 mm unbarbed lead 630, 634 on either side of the barbed section 632. The barbed section 632 may have retainers 624 in one orientation or in different orientations.

Referring now to FIG. 6C which shows a high density distribution of retainers 644 on a drug-eluting self-retaining suture 640. As shown in FIG. 6C, the self-retaining suture 640 has a filament 642 which is of USP 6-0, 7-0, 8-0, 9-0 10-0 or below. As shown in FIG. 6C, the filament is 0.25 mm in diameter which is a 4-0 suture. The self-retaining suture 640 includes a plurality of retainers 644 arranged in groups of four retainers each arranged at 90 degrees spacing. Each adjacent set of four retainers is offset to the adjacent sets by 45 degrees. Each retainer is 0.18 mm from tip of depression to base of cut—measured axially—see arrow 656. The distance between the base of the retainer in one set and the base of the adjacent retainers is 0.28 mm—measured axially—see arrow 658. In an embodiment the self-retaining suture has a barbed section 652 at least 60 mm in length and a 100 mm unbarbed lead 650, 654 on either side of the barbed section 652. The barbed section 652 may have retainers 644 in one orientation or in different orientations.

FIGS. 6D, 6E, and 6F show a range of retainer shapes that can used in conjunction with a drug-eluting self-retaining suture. For each retainer a USP 4-0 suture filament 660 is used. FIG. 6D shows a parabolic retainer 664 for use with either the single-helix (FIG. 6A) or double helix (FIG. 6B) distribution patterns. The depth of cut D (measured transversely) is 0.060 mm. The length of cut L (measured axially) is 0.250 mm. FIG. 6E shows a parabolic retainer 662 shape for use with the high density (FIG. 6C) distribution patterns. The depth of cut D (measured transversely) is 0.036 mm. The length of cut L (measured axially) is 0.170 mm. FIG. 6F shows an alternative retainer 668 having a 30 degree entry and then running parallel to the axis of the suture. The depth of cut D (measured transversely) is 0.036 mm. The length of cut L (measured axially) is 0.234 mm. The angle of entry θ is 30 degrees from the suture axis. These and other retainer shapes can be used to accommodate the density and distribution of retainers desired for a particular applications and with a particular filament diameters. Alternative retainer shapes and distribution patterns are disclosed in U.S. patent application Ser. No. 12/101,885 titled "Self-Retaining Systems for Surgical Procedures" filed Apr. 11, 2008 which is incorporated herein by reference.

Peripheral Nerve Repair

As described above, the purpose of the suture determines the sort of drug that is applied to or incorporated in the suture as well as the diameter of the filament and the shape, size and distribution of the retainers. In one example, drug-eluting self-retaining sutures contain or are coated with nerve growth factor (NGF) to promote healing of damaged nerves. The spectrum of nerve injuries includes simple nerve compression lesions, complete transection, and severe laceration. An adequate and prompt intervention is crucial to achieve a good clinical outcome. The intervention preferably enhances and/or augments the innate healing process.

Figure 7A:
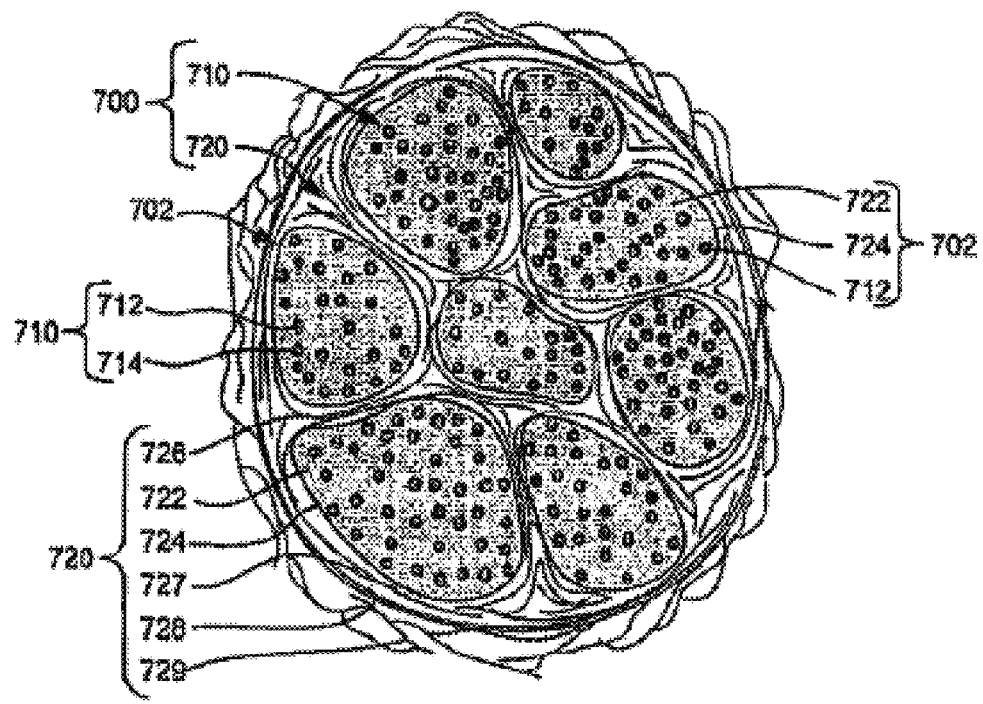
FIG. 7A illustrates a sectional view of a nerve for reference.

For reference, FIG. 7A is a sectional view of a nerve 700. Nerve 700 comprises a plurality of nerve fibers 710 surrounded by connective tissue 720. Nerve fibers 710 include axons 712 surrounded by myelinating Schwann cells 714. Immediately adjacent the nerve fibers 710 is the first layer of connective tissue—the endoneurium 722. Groups of nerve fibers and endoneurium are surrounded by a fascia 724 to form a fascicle 702. The fascicles 702 are themselves surrounded by connective tissue called the perineurium 726. The perineurium and fascicles is surrounded by the internal epineurium 727 and external epineurium 728. The external epineurium is a continuous fascia surrounding the bundle of fascicles and connective tissue. The external epineurium 728 is surrounded by a layer of connective tissue called the mesoneurium 729. In repair of a nerve injury sutures can be applied to the connective tissue in order to reconnect the severed end of the nerves. In order to repair a simple transaction of a nerve the first step is preparation of the nerve ends.

An injury to a peripheral nerve triggers an innate healing process. In the innate healing process, the part of the axon distal to the cut, now cutoff from the axon cell body rapidly disintegrates. Schwann cells surround the distal axon rapidly lose their myelin and macrophages invade the nerve to absorb the myelin. This is an important step for axon regrowth because myelin is an inhibitor of axon growth, The Schwann cells surrounding the distal axon are also stimulated to proliferate and migrate allowing them to extend over a minor nerve defect if a fibrin matrix is present. Schwann cells around the proximal axon undergo the same process but only in the region adjacent the injury. In the proximal axon the injury is communicated intracellular to the nucleus which initiates gene expression necessary to repair the axon. The growing axon responds to contact and chemical signals from the Schwann cells surrounding the distal axon to guide the axon regrowth to the target muscles or sensory cells.

In an embodiment of the present invention, a drug-eluting self-retaining suture is used to supply a drug or drugs (e.g. NGF) to an injured nerve during the critical period immediately post injury. The kinetics for releasing NGF from the self-retaining suture into the nerve tissue adjacent the injury are selected to deliver NGF over the useful period of nerve repair. Factors that can be used to control/adjust the release kinetics of NGF include: the amount of NGF in the filament; the diameter of the filament; the distribution of the NGF in the filament; the formulation/porosity of the material of the filament; and the shape and distribution of retainers on the filament. As the release kinetics are affected by the surface area of retainers in a particular region the kinetics are preferably validated for particular retainer configurations to achieve the desired final kinetics.

Figure 7B:
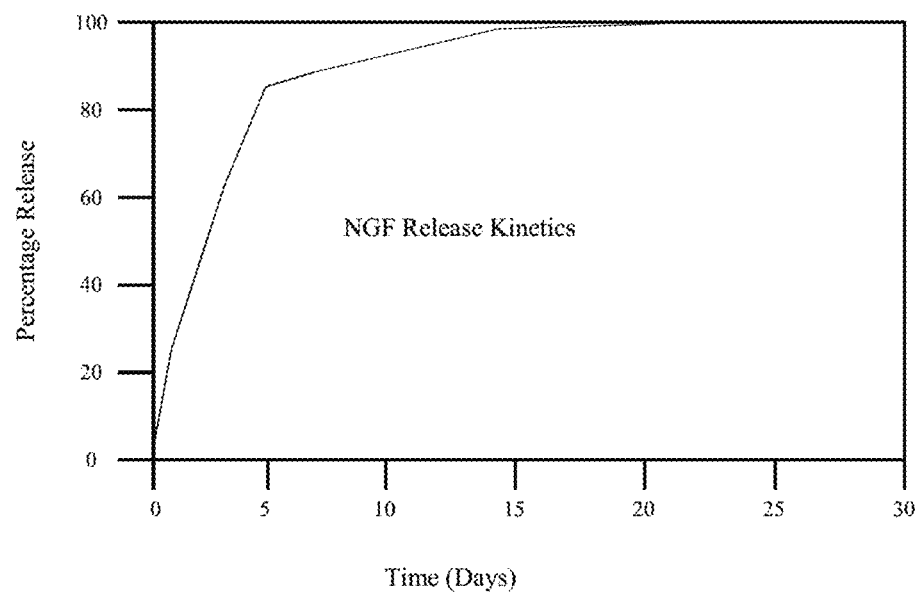
FIG. 7B illustrates the release kinetics for NGF from a drug-eluting self-retaining suture according to an embodiment of the present invention.

In one embodiment first order burst release kinetics are utilized. The graph of FIG. 7B illustrates suitable first order burst in-vitro release (IVR) kinetics for releasing NGF from e.g. an 8-0 self-retaining suture suitable for nerve repair. More than 80% of the NGF is supplied in the first 5 days after implantation in vivo. The remaining NGF is released in the next 20-25 days. The self-retaining suture with NGF thus is suitable for repairing and supporting a lacerated or ruptured nerve and delivering NGF during the critical early period of nerve healing leading to a superior healing response and better clinical outcomes. While NGF is described a range of other agents that promote nerve healing as described herein may be used instead of or in addition to NGF.

A number of drugs in addition to NGF are known to stimulate nerve growth/repair. In embodiments of the present invention, the drugs are coated on, impregnated in or otherwise carried by the self-retaining suture in a manner which allows the release of the drug with suitable kinetics into the region of the injury to a nerve. Drugs suitable to stimulate nerve growth/repair include: neurotrophs, for example, nerve growth factor (NGF), platelet-derived growth factor (PDGF), brain-derived neurotrophic factor (BDNF), neurotrophins-3 (NT-3), neurotrophin-4/5 (NT4/5), neurokines, for example, cilliary neurotrophic factor (CNTF), leukemia inhibitory factor (LIF); and transforming growth factors, for example, transforming growth factors (TGFs)-beta, glial-cell-derived neurotrophic factor (GDNF) growth factor. Other drugs for stimulating nerve growth include fibroblast growth factor (FGF-2), insulin-like growth factors I and II, and other agents which stimulate growth and repair of peripheral nerves. Also, drugs which target myelin-associated inhibitors of regeneration can also be used to promote nerve regeneration by counteracting these inhibitors. The agonists of the myelin-associated inhibitors include, for example the antibodies such as the anti-NOGO antibody which promote axonal sprouting and functional recovery. Moreover other drugs can be used to block the inhibitory effects on the axon growth by disrupting the Rho, Rho-kinase signal pathway in the axon that responds to the myelin-associated inhibitors of regeneration.

Embodiments of the invention can include 8-0 (or smaller) PGA or PDO absorbable suture which can be impregnated during the suture formation process with one or more drugs such as Nerve Growth Factor (NGF). The resulting suture can be barbed and formed into a suture. The release kinetics of the NGF can be tailored to promote healing of lacerated and ruptured nerves. This can entail first order burst release kinetics. The combination of a 8-0 PGA suture's holding strength to maintain tissue apposition and the NGF can produce a superior healing response for the nerve resulting in better functionality. While NGF is specifically noted, it is understood that a wide range of neurotrophic factors, growth factors, and neural cytokines can be used. Embodiments of the invention concept could be extended to the general notion of a drug eluting sutures for active healing of damaged (iatrogenic or non-iatrogenic) tissue with the appropriate drug/growth factors added to the suture material during the manufacturing process.

A double helix (FIG. 6B) or quadra helix (FIG. 6C) barbing pattern may be used to increase holding strength. It should be noted that increasing the surface area of the self-retaining drug-impregnated suture can also increase the release kinetics; this may be accomplished in several ways, for example by increasing the density of retainers (such as barbs) per unit suture surface area, increasing the size of the retainers, and increasing the tissue engagement surface of the retainers.

Nerve injuries comprise simple nerve compression lesions to complete nerve trunk lacerations and ruptures. To repair a nerve laceration or rupture, there are four steps: (1) preparation of the nerve ends, (2) approximation of the nerve end, (3) coaptation of the nerve ends, and (4) maintenance of coaptation of the nerve ends. Steps 2 through 4 require the ability to the hold the neural tissue in apposition as a function of time. Published literature suggests current techniques do not always maintain the proper apposition to affect repair. Sutures have demonstrated the ability to bring tissue into apposition under high tension and maintain the tissue in the required position. Self-retaining sutures configured for nerve repair can accomplish this same effect as well as remove suture mass due to a lack of knots. The lack of knots can reduce inflammation in the surrounding tissue. The addition of NGF and the use of such a suture as a drug delivery vehicle provides a controlled mechanism to promote active healing thereby accelerating the neural repair process for a more consistent clinical outcome.

Conventional nylon and resorbable sutures, silicone tubes, glues (fibrin and synthetic), PEG hydrogels alone or in combination have all been used to bridge nerve lacerations and ruptures. All these materials suffer from the inability to control tension or rely on point fixation, thus they are less than optimum in maintaining nerve tissue apposition.

Figure 7C:
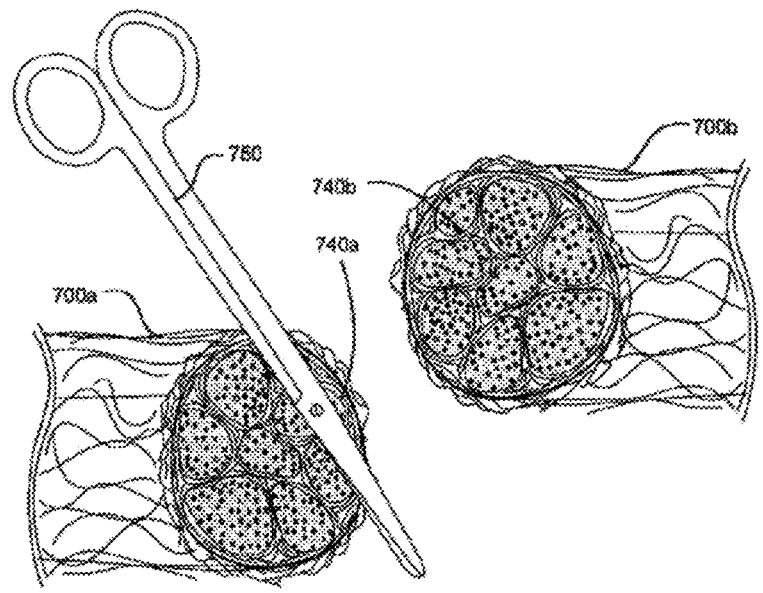
FIGS. 7C-7I illustrate a procedure for repairing a nerve utilizing a drug-eluting self-retaining suture according to an embodiment of the present invention.

FIG. 7C-7F illustrate certain steps in the repair of a severed peripheral nerve 700 utilizing a drug-eluting self-retaining suture. First, the site of the injury must be exposed in order to visualize the injury to the nerve. In order to repair nerve 700 it is first necessary, as shown in FIG. 7C to prepare the severed ends 740a and 740b of the two portions 700a, 700b of nerve 700. The zone of damaged/necrotic tissue must be defined. A pair of sharp micro scissors 750 or a surgical blade (not shown) is used to remove any necrotic tissue so that severed ends 740a, 740b are viable for attachment. Sharp debridement of the damaged nerve ends provides clean edge to the fascicles.

Figure 7D:
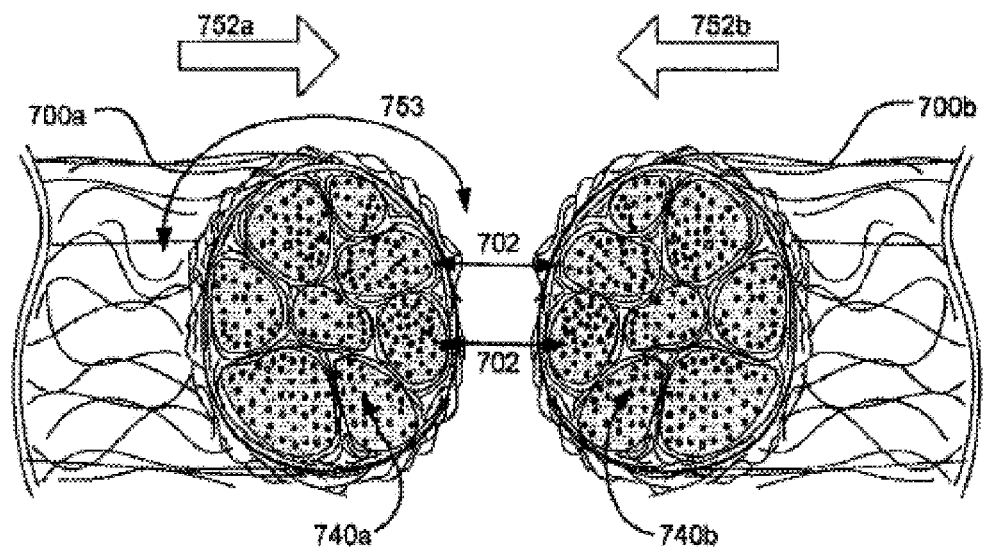

FIG. 7D shows the next step of peripheral nerve repair in which the severed ends 740a, 740b of the nerve section 700a, 700b are approximated to one another. This approximation step usually requires the mobilization of the nerve sections in order to bridge any small defect (gap) left by the injury or debridement. The nerve sections 700a, 700b are mobilized by dissecting the nerve away from the underlying tissues in the region adjacent severed ends 740a, 740b. The severed ends 740a, 740b are then approximated as shown by arrows 752a, 752b. The severed ends are also rotated as shown by arrow 753 in order to align group fascicles 702 and/or longitudinal epineural vessels (not shown). If the nerve ends have retracted they can be approximated by placing a suture through the epineurium into soft tissue adjacent each severed end 740a, 740b.

Figure 7E:
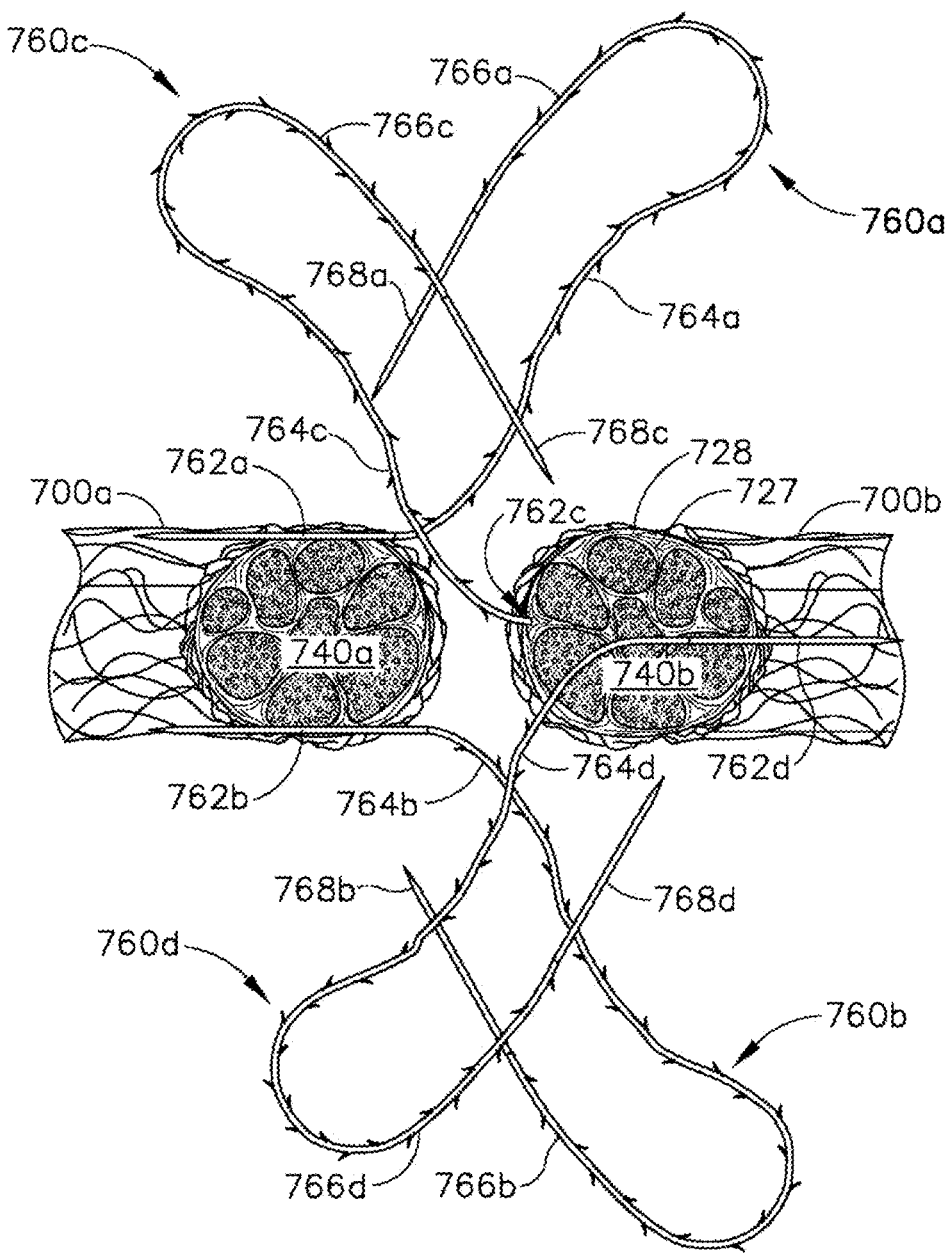
Figure 7F:
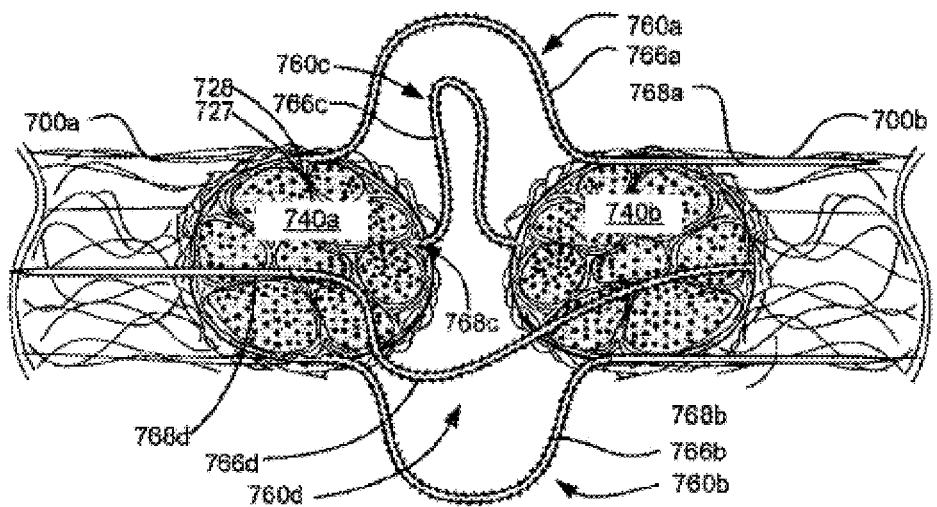
Figure 7G:
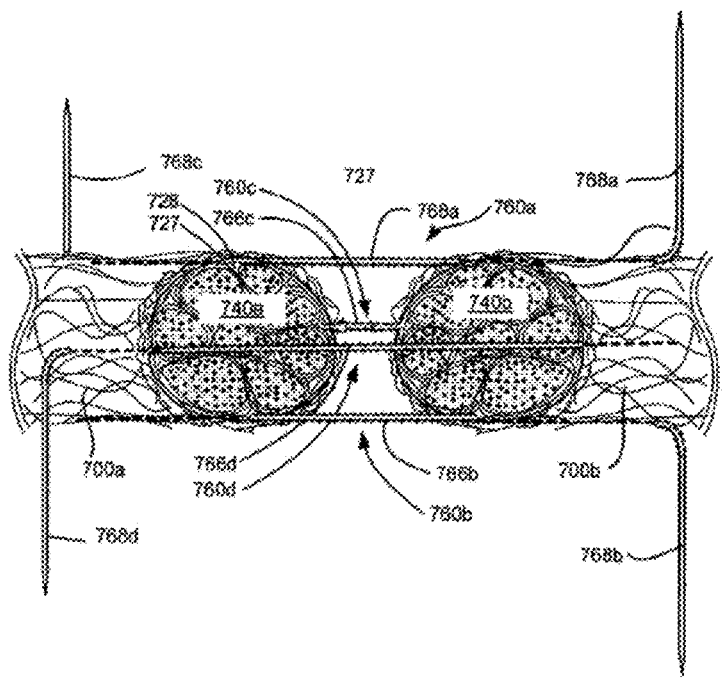

After approximation and alignment of severed nerve ends 740a, 740b, the ends 740a, 740b are sutured to one another in a number of ways. FIGS. 7E, 7F and 7G illustrate a suturing technique utilizing four bidirectional drug-eluting self-retaining sutures 760a, 760b, 760c, 760d. FIG. 7E shows the first suturing step. As shown in FIG. 7E, each of the four sutures has a straight needle 762a, 762b, 762c, 762d at one end attached to a portion 764a, 764b, 764c, 764d of suture with retainers oriented to allow movement in the direction of needle 762 but not in the other direction. Each portion 764a, 764b, 764c, 764d is joined to a second portion of suture 766a, 766b, 766c, 766d with retainers oriented to allow movement in the direction of a second straight needle 768a, 768b, 768c, 768d but not in the other direction. In the first step, as shown in FIG. 7E, First needles 762a, 762b are driven longitudinally into the epineurium surrounding severed end 740a and first needles 762c, 762d are driven into the epineural tissue surrounding severed end 740b. The needles are spaced around the perimeter of the severed ends 740a, 740b. The first needles 762a, 762b, 762c, 762d, are then used to draw the first portions 764a, 764b, 764c, 764d of suture into the epineurium until the second portion 766a, 766b, 766c, 766d of suture engages the epineurium and prevents further advancement of the suture in the direction of the first needles 762a, 762b, 762c, 762d. At this point, the first needles 762a, 762b, 762c, 762d and first portions 764a, 764b, 764c, 764d extending out of the epineurium 727, 728 are cut and removed from the operative field leaving only a longitudinal segment of first portions 764a, 764b, 764c, 764d embedded in the epineurium 727, 728.

FIGS. 7F and 7G show the second suturing step. In the second step, as shown in FIG. 7F, second needles 768a, 768b are driven longitudinally into the epineurium surrounding severed end 740b and second needles 768c, 768d are driven into the epineural tissue surrounding severed end 740a. The needles are spaced around the perimeter of the severed ends 740a, 740b and care is taken to align the location of second needles 768a, 768b, 768c, 768d with the corresponding position of the first needles 762a, 762b, 762c, 762d, The second needles 768a, 768b, 768c, 768d, are then used to draw the second portions 766a, 766b, 766c, 766d of suture into the epineurium until the second portions of suture 766a, 766b, 766c, 766d are not slack, but without tension as shown in FIG. 7G. As shown in FIG. 7G, second needles 768a, 768b, 768c, 768d exit the epineurium 727, 728 of the nerve 700a, 700b some distance from the severed ends 740a, 740b.

Figure 7H:
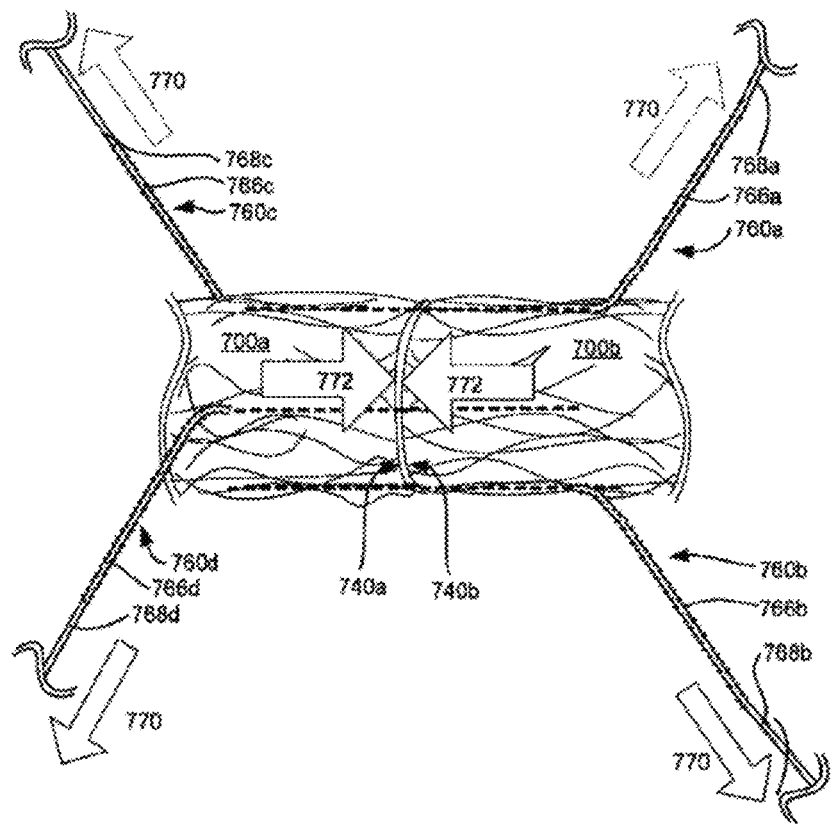
Figure 7I:
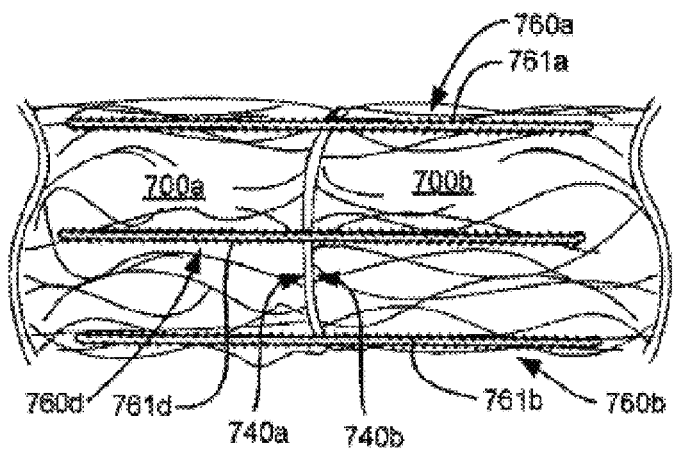

FIG. 7H shows the final suturing step. As shown in FIG. 7H, second needles 768a, 768b, 768c, 768d are simultaneously drawn away from the severed ends 740a, 740b as shown by arrows 770. The second needles draw the second portions 766a, 766b, 766c, 766d of suture through the epineurium 727, 728. Because the first portions 764a, 764b, 764c, 764d of suture are embedded in the epineurium 727, 728 on the opposite side of severed ends 740a, 740b, pulling through second portions 766a, 766b, 766c, 766d draws severed ends 740a, 740b towards each other (as shown by arrows 772) and into aligned contact with each other. The segment of the second portions 766a, 766b, 766c, 766d external to the nerve and the attached second needles 768a, 768b, 768c, 768d may then be cut off and removed from the operative field. Leaving the nerve 700a, 700b reattached to one another with severed end 740a, aligned and abutting one another as shown in FIG. 7I. Additional conventional or self-retaining suture sutures can be used to further reinforce the connection between nerves 700a, 700b. Alternatively or additionally, the connection between nerve 700a, 700b can be augmented with a fibrin-based surgical adhesive.

As shown in FIG. 7I, a segment 761a, 761b, 761c (not shown), 761d of each self-retaining suture 760a, 760b, 760c (not shown), 760d is embedded in the nerves 700a, 700b inside the external epineurium (not shown) and spanning the severed ends. 740a, 740b. The segments 761a, 761b, 761c (not shown), 761d are also evenly spaced around the nerve. The segments of self-retaining suture 761a, 761b, 761c (not shown), 761d distribute any tension in nerve 700a, 700b across the entire segment 761a, 761b, 761c (not shown), 761d of self-retaining suture rather than concentrating all the tension at the severed ends 740a, 740b. The segments are ideally positioned within the external epineurium to deliver a drug to enhance regeneration of the nerve 700a, 700b. Also, as the length of the segments 761a, 761b, 761c (not shown), 761d of self-retaining suture embedded in the epineurium can be readily controlled by the surgeon, the amount of drug that will be released from the suture is also well defined for each segment. In a preferred embodiment the suture is provided with visible markers such as a coloring to guide the surgeon as to the correct length of segment to be embedded (and/or the location of the transition from retainers of one direction to retainers of the other direction. The surgeon may also be guided by the length of the first needles 762a, 762b, 762c, 762d and second needles 768a, 768b, 768c, 768d which dictates the size of the bite which is taken through the epineurium. In alternative embodiments, 2, 4, 6, 8 or more self-retaining sutures are utilized depending upon the nerve to repair.

Figure 8A:
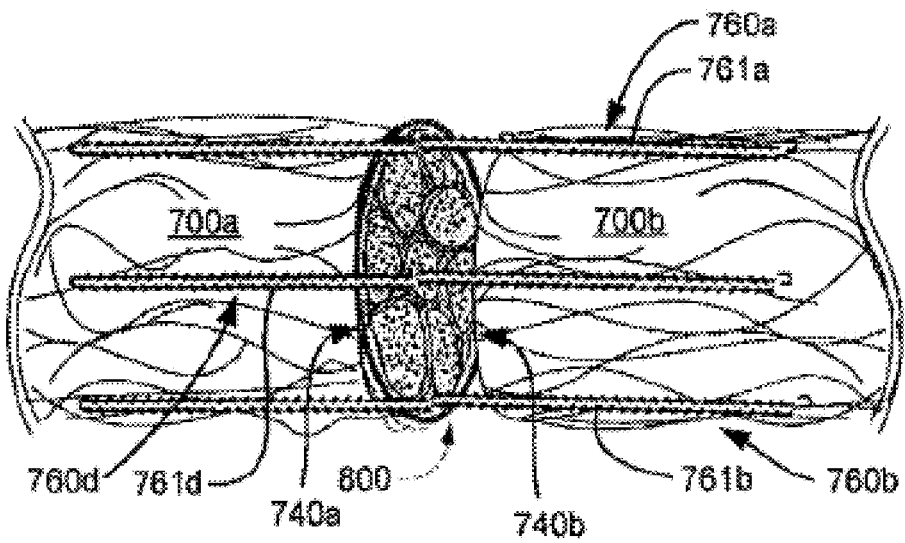
FIGS. 8A and 8B illustrate techniques utilizing drug-eluting self-retaining sutures to bridge a nerve defect.
Figure 8B:
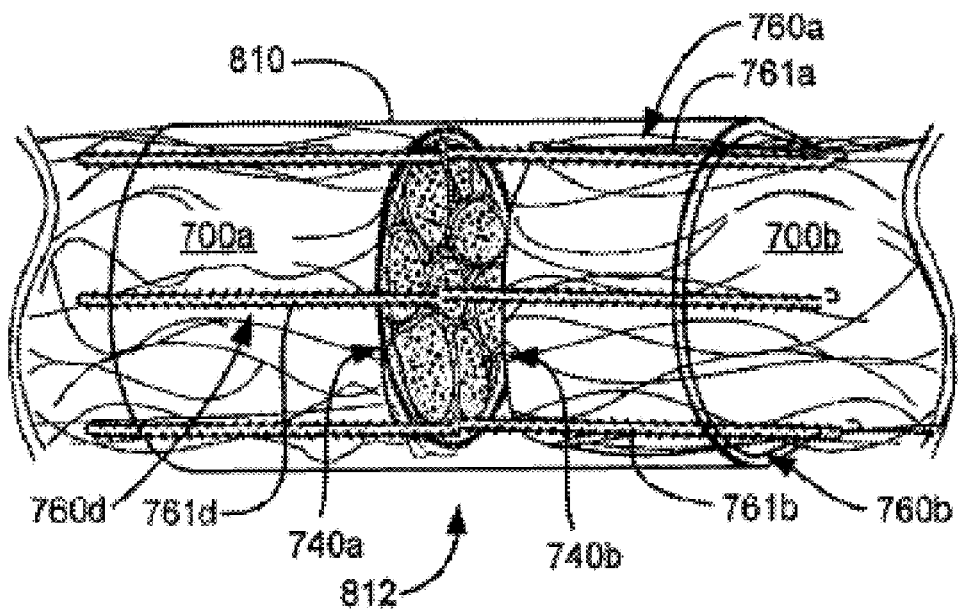

FIGS. 8A and 8B show techniques utilizing drug-eluting self-retaining sutures to bridge a nerve defect. As shown, in FIG. 8A, it may not be possible to bring the severed ends 740a, 740b of nerve 700A, 700B into direct contact. The result is a small gap or defect 800 that remains between the severed ends 740a, 740b as shown in FIG. 8A. The defect 800 in the nerve is bridged by a naturally formed fibrin string between the severed ends 740a, 740b. Blood and plasma exuding from the severed ends 740a, 740b bridges the defect 800 and subsequently Schwann cells migrate over the defect using the fibrin as a guide. Self-retaining sutures 760a, 760b, 760c, 760d spanning the defect 800 longitudinally, as shown in FIG. 8A, can serve as guide for fibrin coagulation as well as guide subsequent Schwann cell migration. Additional drug-eluting self-retaining sutures could then be deployed across the defect, if desired, to provide more guidance and support for axonal migration.

As shown in FIG. 8B, in some applications in may be necessary or desirable to provide additional protection of the defect during the healing process. Thus, it may be desirable to enclose the defect 812 supported by the drug-eluting self-retaining sutures in a tube 810. The tube 810 protects the defect and also serves to concentrate drugs eluting from self-retaining sutures 760a, 760b, 760c, 760d in the immediate vicinity of the defect 812. To facilitate use of a tube 810, the second needles 768a, 768b, 768c, 768d and second ends 766a, 766b, 766c, 766d of the self-retaining sutures 760a, 760b, 760c, 760d are inserted through the tube between the steps shown in FIG. 7E and FIG. 7F. If so inserted when the second ends are drawn through in step 7H, the severed ends 740a, 740b will be drawn into the tube 810 and towards each other. The resulting configuration is as shown in FIG. 8B which shows tube 810 in position around self-retaining sutures 760a, 760b, 760c, 760d and defect 812 in nerve 700a, 700b.

Figure 9A:
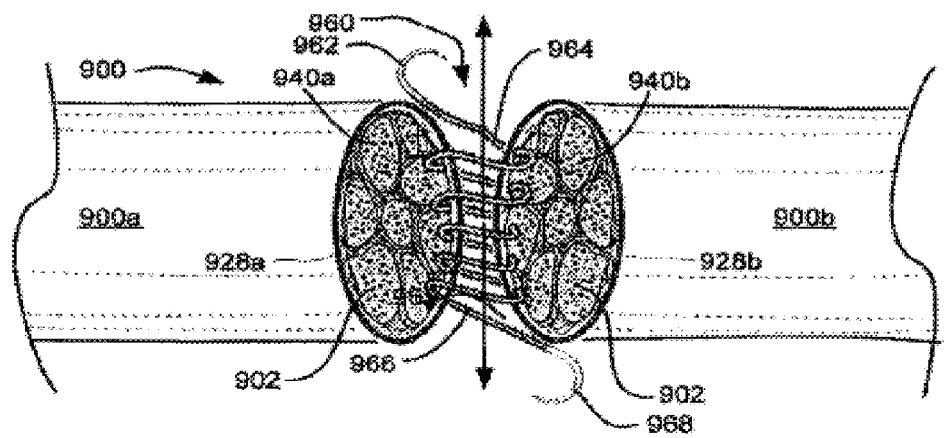
FIGS. 9A, 9B and 9C illustrate an alternative technique for reattaching a severed nerve utilizing one or more drug-eluting self-retaining sutures.
Figure 9B:
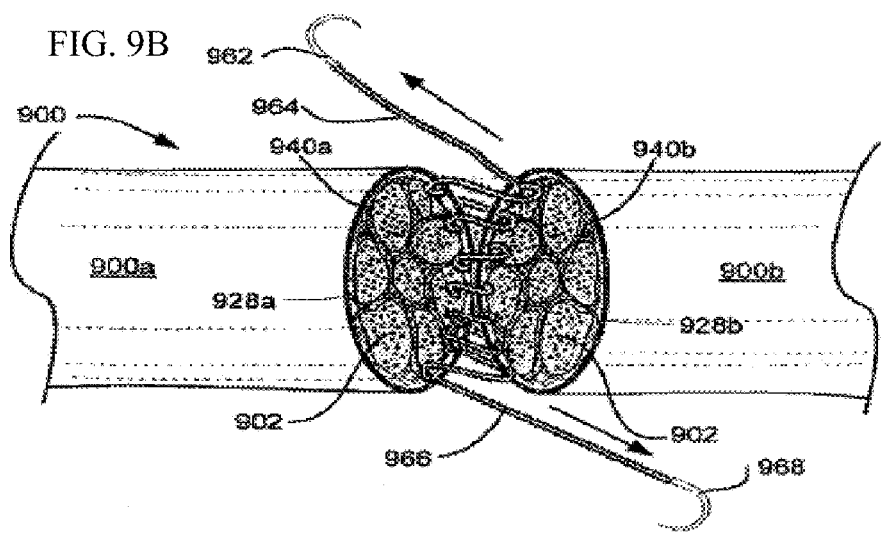
Figure 9C:
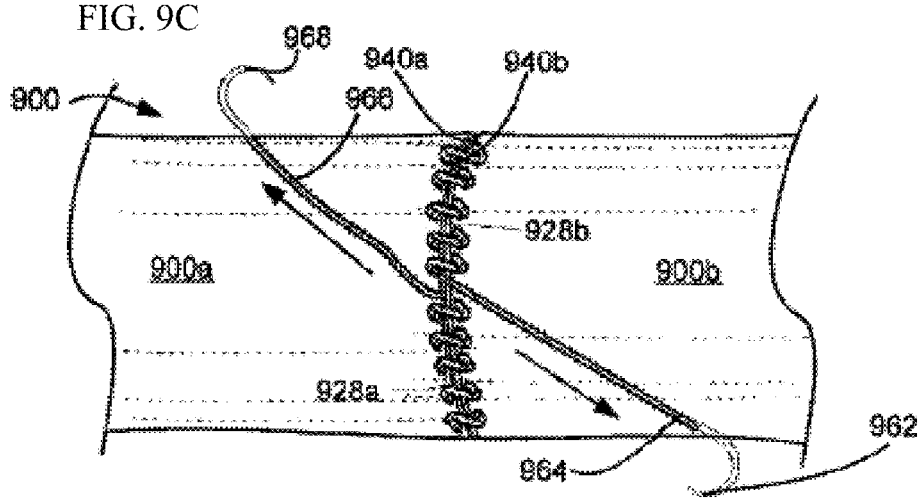

FIGS. 9A, 9B and 9C show an alternative technique for reattaching a severed nerve using a technique utilizing one or more drug-eluting self-retaining sutures. In the method illustrated in FIGS. 9A, 9B and 9C a drug-eluting self-retaining suture is used to join the severed ends 940a, 940b of a nerve 900 severed into two portions 900a and 900b. First, the site of the injury must be exposed in order to visualize the injury to the nerve. Then the severed ends 940a and 940b of the two portions 900a, 900b of nerve 900 must be debrided of any necrotic tissue so that severed ends 940a, 940b are viable for attachment. Sharp debridement of the damaged nerve ends provides clean edge to the fascicles. The severed ends 940a, 940b of the nerve sections 900a, 900b are approximated to one another. This approximation step usually requires the mobilization of the nerve sections in order to bridge any small defect (gap) left by the injury or debridement. The nerve sections 900a, 900b are mobilized by dissecting the nerve away from the underlying tissues in the region adjacent severed ends 940a, 940b. The severed ends 940a, 940b are then approximated and rotated as previously described in order to align group fascicles 902 and/or longitudinal epineural vessels (not shown).

After approximation and alignment of severed nerve ends 940a, 940b, the ends are sutured to one another using an anastomosis technique employing a drug-eluting self-retaining suture 960. FIG. 9A shows the first suturing step. As shown in FIG. 9A, the self-retaining suture 960 has a curved needle 962 at one end attached to a first portion 964 of suture with retainers oriented to allow movement in the direction of needle 962 but not in the other direction. The first portion 964 is joined to a second portion of suture 966 with retainers oriented to allow movement in the direction of a second curved needle 968 but not in the other direction.

In the first step, illustrated in FIG. 9A, the first needle 962 is driven through the epineurium 928a of severed end 940a and the second needle 968 is driven through the epineurium 928b of severed end 940b. It is best to start on the distal side of the nerve 900a, 900b and work towards the proximal side. The first and second portions of self-retaining suture 964 and 966 are drawn through until the transition point lies approximately equidistant between the two severed ends 940, 940b. Then each needle 962, 968 is used to take bites through the epineurium of the opposite severed end alternating as moving away from the initial bite. As shown in FIG. 9A, the first needle 962 and second needle 968 travel in opposite directions around the severed ends 940a, 940b. In this first step, no tension is applied to the first and second portion 964, 966 of self-retaining suture.

As shown in FIG. 9B when the first and second portions 964, 966 reach opposite sides of the severed ends 940a, 940b, the self-retaining suture can be drawn tight causing the severed ends 940a and 940b to be drawn against each other along one half of the defect. Care should be taken to ensure that the suture tightens evenly along the defect to ensure that there are no concentrations of tension or pressure on severed ends 940a, 940b.

As shown in FIG. 9C the next step is continuing with alternating bites of first and second portions of suture 964, 966 towards each other around the proximal edge of severed ends 940a, 940b. When the first and second portions 964, 966 reach the midpoint of the proximal side of the severed ends 940a, 940b, the self-retaining suture can be drawn tight against causing the severed ends 940a and 940b to be drawn against each other along the proximal half of the defect. Care should be taken to ensure that the suture tightens evenly along the defect to ensure that there are no concentrations of tension of pressure on severed ends 940a, 940b. As a self-retaining suture is used no knots are required to complete the repair thus reducing the chance of uneven tension. An extra bite through the epineurium may be taken if desired to secure the ends of the first and second portions of self-retaining suture prior to cutting off the excess self-retaining suture and needles 962, 968.

As shown in FIG. 9C the bites of self-retaining suture 960 are embedded in the nerve 900 through the external epineurium (not shown) and spanning the severed ends 940a, 940b. The bites of self-retaining suture are also evenly spaced around the severed ends 940a, 940b. The self-retaining suture 960 can distribute any tension in nerve 900 across the entire defect rather than concentrating tension in one or more places. The self-retaining suture is ideally positioned within the external epineurium to deliver a drug to enhance regeneration of the nerve 900. Also, as the length of self-retaining suture embedded in the epineurium varies with the circumference of the nerve, the amount of drug that will be released from the suture is well matched to the defect. In a preferred embodiment, the suture is provided with visible markers such as a coloring to guide the surgeon (and/or indicate the location of the transition from retainers of one direction to retainers of the other direction. The surgeon may also be guided by the length and shape of the curved needles 962, 968 which dictates the size of the bite which is taken through the epineurium 928a, 928b. In alternative embodiments, two, four, or more self-retaining sutures may be utilized depending upon the nerve to repair. Where two self-retaining sutures are deployed they should be commenced at opposite sides of the severed ends 940a, 940b.

Bioactivity of Drug Eluted from Drug-Loaded Sutures

Bioabsorbable polydioxanone (PDO) loaded with NGF nanoparticles was manufactured into sutures having diameters of about 0.045 mm (that is, within the USP range for 8-0 gauge sutures), in accordance with methods disclosed in U.S. Pat. No. 6,596,296. The sutures had a targeted NGF drug loading of 10 ng/cm of suture length. (Additional sutures were produced with lower targeted NGF concentrations, including 1 ng/cm and 0.1 ng/cm, but these were not used in the tests described below.)

For drug eluting sutures with sizes ranging from USP 12-0 to USP 7-0 (approximately 0.001 mm to 0.069 mm diameter), and especially for protein drug-eluting sutures (such as, but not limited to, NGF and VEGF), the concentration range of the drug per length of suture may be about 100 $ng_{DRUG}/cm_{SUTURE}$ to 0.001 $ng_{DRUG}/cm_{SUTURE}$. For drug-eluting sutures with sizes ranging from USP 6-0 to USP 5 (approximately 0.070 mm to 0.799 mm diameter), the concentration range of the drug per length of suture may be about 15% $wt_{DRUG}/wt_{SUTURE}$ to 0.001 $ng_{DRUG}/cm_{SUTURE}$.

For drug-eluting sutures, different filament materials and different eluting drugs (such as protein drugs like NGF and VEGF) will release the drug at different rates, and the dosing parameters may be utilized in combination with the release rate of the drug from the filament such that a minimum concentration of about $10^{-13}$ M to $10^{-12}$ M, or about $10^{12}$ M to $10^{-11}$ M, or about $10^{-11}$ M to $10^{-10}$ M, or about $10^{-10}$ M to $10^{-9}$ M, or about $10^{-9}$ M to $10^{-8}$ M, or about $10^{-8}$ M to $10^{-7}$ M of the agent is maintained in the vicinity of or on the tissue surface to maintain the desired therapeutic effect for the required period of time. The required minimum concentration is dependent on the potency of the agent under consideration and the desired therapeutic effect.

Batches of NGF-loaded PDO sutures having a diameter of about 0.045 mm (that is, within the USP range for 8-0 sutures, an appropriate gauge for nerve repair) were tested in cell line PC12 to determine whether biologically active NGF elutes from the NGF-loaded PDO suture. The PC12 cell line is derived from a pheochromocytoma of the rat adrenal medulla, and, in the presence of 0.5 ng/ml to 50 ng/ml of NGF with serum-supplemented media, the cell line is known to undergo a dramatic change in phenotype and to emulate the growth of sympathetic neurons by generating long neuritis, making it a very useful test subject for detecting biologically active NGF. Furthermore, the maintenance of PC12 neurites requires the continued presence of NGF; if the NGF exposure is discontinued, then the PC12 neurites will retract or degenerate, and the PC12 cells will resume normal proliferation within approximately a week. Two sets of cell cultures, one in the presence of NGF-loaded sutures and the other in the absence of NGF-loaded sutures, were grown for two days.

Figure 10A:
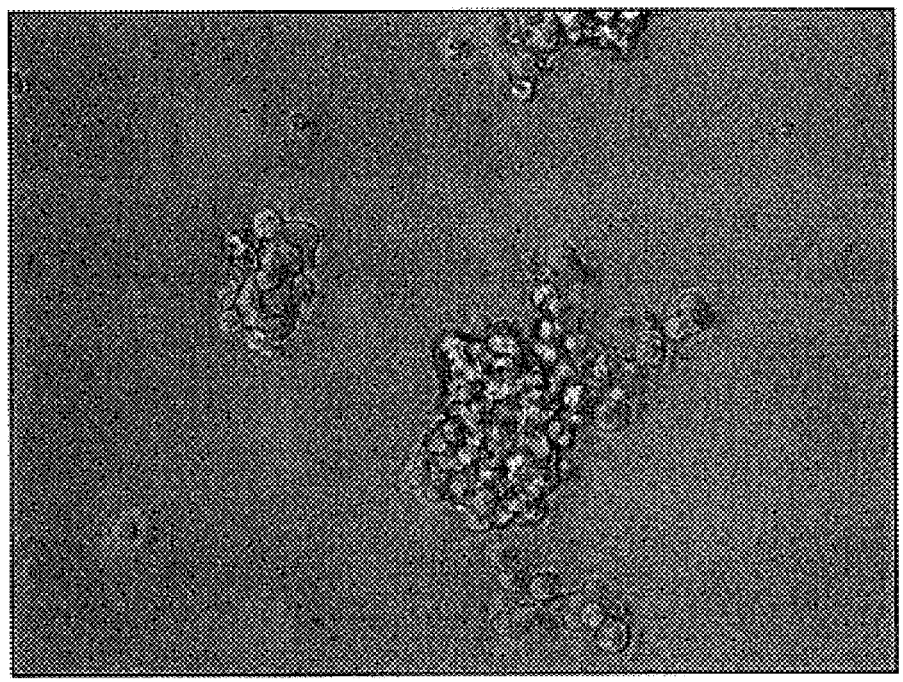
FIGS. 10A and 10B show PC12 cell culture responses to exposure to no NGF-loaded suture and NGF-loaded suture, respectively.
Figure 10B:
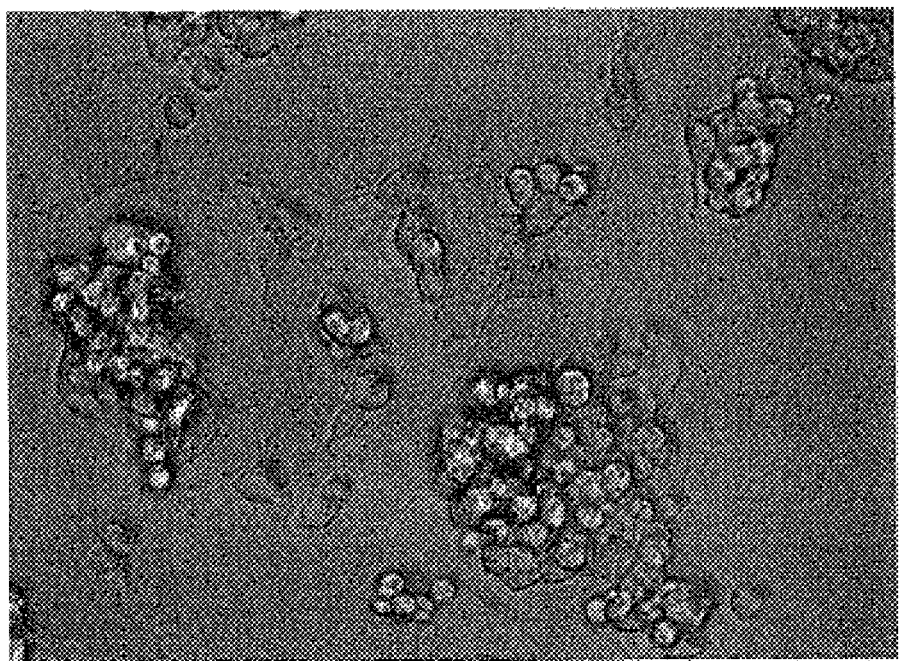

FIG. 10A shows non-differentiated PC12 cells with serum-supplemented media without exposure to NGF-loaded sutures. The PC12 cells proliferated without cell differentiation or the generation of long neurite structures. In contrast, FIG. 10B shows differentiated PC12 cells with serum-supplemented media which were exposed to NGF-loaded sutures. The PC12 cells stopped proliferating and began to differentiate by generating long neurite structures; these structures are clearly visible in FIG. 10B. As it is known that this phenotype differentiation occurs only when the PC12 cells are exposed to NGF with a drug concentration range from 0.5 ng/ml to 50 ng/ml NGF, the cellular phenotypic differentiation in FIG. 10B indicates both (1) the biological activity of the NGF eluted from the drug-loaded sutures, and (2) that the bioactive NGF was within the range of 0.5 ng/ml to 50 ng/ml.

Figure 11A:
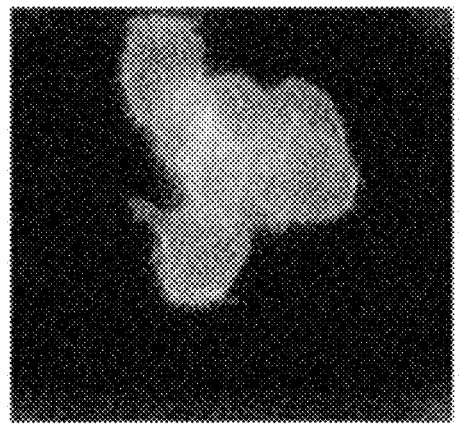
FIGS. 11A-D show PC12 cell culture responses to no NGF-loaded suture and to varying amounts of NGF-loaded suture, respectively, in a green phalloidin stain.
Figure 11B:
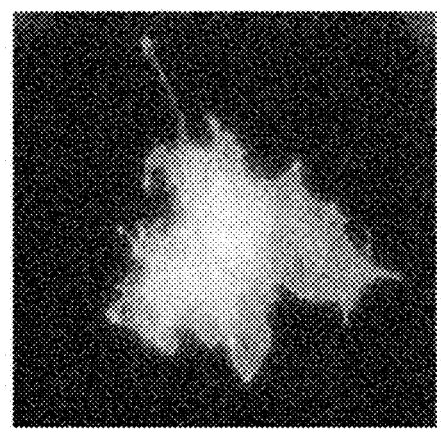
Figure 11C:
Figure 11D:
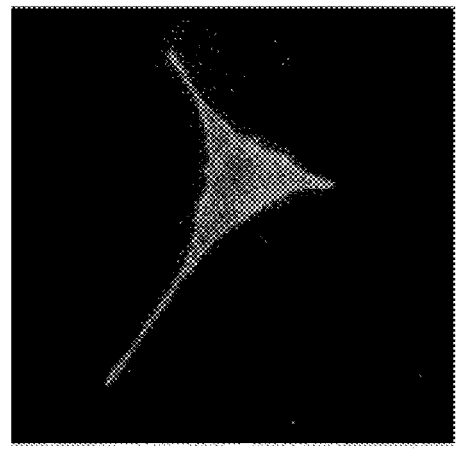
Figure 12:
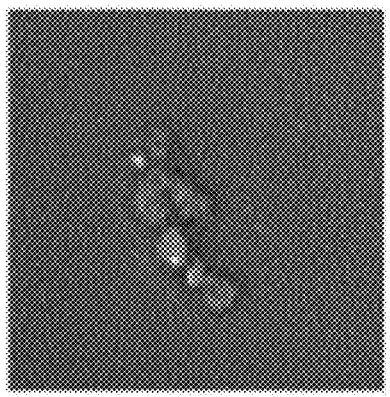
FIGS. 12A-C show PC12 cell culture responses, in phase contrast, to no NGF-loaded suture and to 5 cm and 10 cm lengths of NGF-loaded suture, respectively.
Figure 12B:
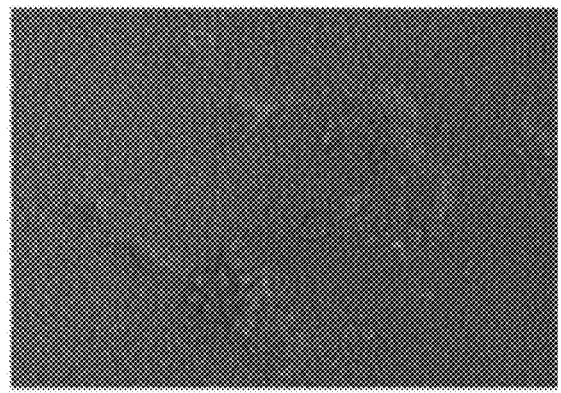
Figure 12:
Figure 13:
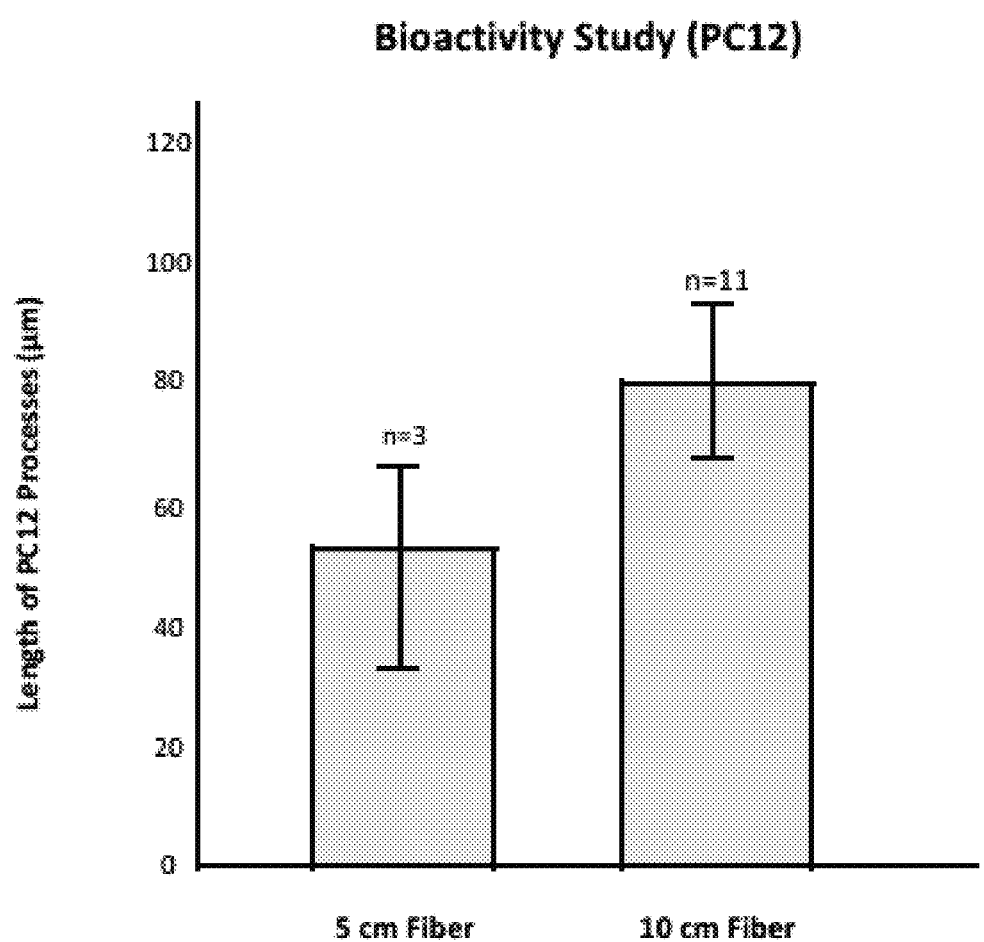
FIG. 13 is a graph illustrating the dose response of PC12 cell cultures to varying amounts of NGF-loaded suture.

The correlation of NGF dose response to surface area of the NGF-loaded suture material was also tested in the PC12 cell line, by comparing the biological response of PC12 cell cultures to shorter (i.e., 5 cm) lengths of NGF-loaded sutures and to longer (i.e., 10 cm) lengths of NGF-loaded sutures. (While the theoretical load concentration of these sutures was 500 ng of NGF per milliliter, it should be noted that the actual elution of NGF passed within the range of 0.5 ng/ml to 50 ng/ml, as evidenced by the phenotypic differentiation of the PC12 cells. Had the actual elution exceeded the range, such differentiation would not have been seen.) As the sutures had the same diameter, the dose response correlated to the surface area of the sutures, and therefore the NGF dosage exposure. FIGS. 11 and 12 show the differentiation of PC12 cell in the presence of the longer (10 cm) and shorter (5 cm) lengths of NGF-loaded sutures. FIGS. 11A to 11D show the PC12 cell cultures, stained in green phalloidin, that were exposed to no NGF-loaded suture (FIG. 11A), that were exposed to 5 cm length of NGF-loaded suture (FIGS. 11B and 11B), and that were exposed to 10 cm length of NGF-loaded suture (FIG. 11D). Similarly, FIGS. 12A to 12C show the PC12 cell cultures, in phase contrast, that were exposed to no NGF-loaded suture (FIG. 12A), that were exposed to 5 cm length of NGF-loaded suture (FIG. 12B), and that were exposed to 10 cm length of NGF-loaded suture (FIG. 12C). As can be seen from the comparative bar graph in FIG. 13, the neuritic processes that were generated in cell cultures exposed to greater total surface area of drug-eluting suture (corresponding to the 10 cm suture lengths) were substantially longer than those exposed to the lesser drug-eluting surface area (corresponding to the 5 cm suture lengths). Thus, the increase in drug-eluting suture surface area correlated to an increase in the drug release kinetics, which in turn correlated to an increased dose response.

Additional Clinical Uses

In addition to the general wound closure and soft tissue repair applications, drug eluting self-retaining sutures can be used in a variety of other indications. The drug eluting self-retaining suture may be implanted into many sites in the body including dermal tissues, cardiac tissue, soft tissues, nerves, the eye, arteries, veins, ducts, bile duct, ureter, urethra, trachea, esophagus, intestine, colon, and connective tissue such as tendons, ligaments, muscle and bone. The drug eluting self-retaining sutures have the advantage of providing the body with not only targeted application of the drug but also mechanical support and tissue retention without knots or staples.

Self-retaining sutures described herein may be used in various dental procedures, i.e., oral and maxillofacial surgical procedures and thus may be referred to as "self-retaining dental sutures." The above-mentioned procedures include, but are not limited to, oral surgery (e.g., removal of impacted or broken teeth), surgery to provide bone augmentation, surgery to repair dentofacial deformities, repair following trauma (e.g., facial bone fractures and injuries), surgical treatment of odontogenic and non-odontogenic tumors, reconstructive surgeries, repair of cleft lip or cleft palate, congenital craniofacial deformities, and esthetic facial surgery. Self-retaining dental sutures may be degradable or non-degradable, and may typically range in size from USP 2-0 to USP 6-0.

Self-retaining sutures described herein may also be used in tissue repositioning surgical procedures and thus may be referred to as "self-retaining tissue repositioning sutures". Such surgical procedures include, without limitation, face lifts, neck lifts, brow lifts, thigh lifts, and breast lifts. Self-retaining sutures used in tissue repositioning procedures may vary depending on the tissue being repositioned; for example, sutures with larger and further spaced-apart retainers may be suitably employed with relatively soft tissues such as fatty tissues.

Self-retaining sutures described herein may also be used in microsurgical procedures that are performed under a surgical microscope (and thus may be referred to as "self-retaining microsutures"). Such surgical procedures include, but are not limited to, reattachment and repair of peripheral nerves, spinal microsurgery, microsurgery of the hand, various plastic microsurgical procedures (e.g., facial reconstruction), microsurgery of the male or female reproductive systems, and various types of reconstructive microsurgery.

Microsurgical reconstruction is used for complex reconstructive surgery problems when other options such as primary closure, healing by secondary intention, skin grafting, local flap transfer, and distant flap transfer are not adequate. Self-retaining microsutures have a very small caliber, often as small as USP 9-0 or USP 10-0, and may have an attached needle of corresponding size. The microsutures may be degradable or non-degradable.

Self-retaining sutures described herein may also be used to enhance bone fracture healing. The self-retaining suture can be wrapped around the bone and/or implanted in the bone of other tissues at the site of the fracture; releasing drugs to promote fracture repair e.g. growth hormones. The self-retaining suture can also be used to make a 2D or 3D mesh structure to facilitate placement of the self-retaining suture and/or drug delivery from the self-retaining suture to the target facture tissue.

Self-retaining sutures as described herein may be used in similarly small caliber ranges for ophthalmic surgical procedures and thus may be referred to as "ophthalmic self-retaining sutures". Such procedures include but are not limited to keratoplasty, cataract, and vitreous retinal microsurgical procedures. Ophthalmic self-retaining sutures may be degradable or non-degradable, and have an attached needle of correspondingly-small caliber.

Self-retaining sutures can be used in a variety of veterinary applications for a wide number of surgical and traumatic purposes in animal health.

Sterilization

Further, drug-eluting self-retaining sutures of the present invention should preferably be have a stable shelf-life for at least several months and capable of being produced and maintained under sterile conditions. The compositions or sutures may be sterile either by preparing them under aseptic environment and/or they may be terminally sterilized using methods available in the art. Many pharmaceuticals/medical devices are manufactured to be sterile under criteria defined by the U.S. Pharmacopeia (see www.usp.org, Rockville, Md.), or AAMI Standards defined by the Association for the Advancement of Medical Instrumentation, or ISO Standards defined by e.g. The International Organization for Standardization (ISO) or The European Committee for Standardization (CEN). Sterilization may be accomplished by a number of means, including for example, gas sterilization or ionizing radiation. Acceptable gases used for gas sterilization include ethylene oxide. Acceptable radiation types used for ionizing radiation methods include gamma, for instance from a cobalt 60 source and electron beam. A typical dose of gamma radiation is 2.5 MRad. Sterilization may also occur by terminally using gamma radiation or electron beam sterilization methods. A combination of these methods may also be used to prepare the compositions and sutures in the sterile form. The sterilization method and/or doses are selected so that sufficient drug activity remains in the sterilized drug-eluting self-retaining suture to cause the therapeutic effect desired. In this connection, issues to be considered in selecting sterilization methods and/or doses include whether the method/dose may denature the drug(s), induce production of free radicals (which may decrease the stability of the drug(s) over the shelf-life of the suture and/or change the moieties of the drug(s)), or cause loss of potency of the drug (for example, through passive diffusion in the case of methods of sterilization involving aqueous solutions). Cost of the sterilization method/dose may also be a consideration.

Optional Embodiments

Specific embodiments that have been disclosed herein include the following:

A suture comprising: a filament; a drug associated with the filament; a plurality of tissue retainers formed in the filament; wherein kinetics of the release of the therapeutic agent is determined by the distribution of the therapeutic agent in at least one of the filament or the retainers. Optionally, said filament include a core and a sheath that covers said core and wherein said drug is provided in at least one of said core and said sheath, where in one embodiment the drug is provided in the core, optionally only in the core, while in another embodiment the drug is provided in the sheath, optionally only in the sheath. The drug may be distributed in said core isotropically, or it may be distributed anisotropically. The drug may be distributed in said sheath isotropicaly, or it may be distributed anisotropically. The retainers may be formed in the sheath, and in this embodiment the drug may be associated with the retainers, optionally to provide anisotropic release of the drug. The drug may be associated with the filament to provide for one of anisotropic release of the drug and isotropic release of the therapeutic agent. The drug may be distributed in said core so as to provide for at least one of isotropically and anisotropically release of the therapeutic agent. The drug may be distributed in said sheath so as to provide for at least one of isotropically and anisotropically release of the drug. In order to prepare the suture, four options are to form the sheath by one of extruding a bi-component fiber with a core/sheath structure, extruding a sheath material over a core, spraying sheath material over a core, or dipping the core into a composition containing the sheath material, including in each instance, precursor materials to the sheath material. In one embodiment, the filament includes one of Nerve Growth Factor (NGF) or Bone Morphogenic Protein (BMP). Optionally, the filament includes a plurality of braided suture threads. Optionally, one of the core and the sheath has a higher concentration of said drug than the other of the core and the sheath. Optionally, said filament includes a first end portion, a second end portion and a middle portion, and wherein at least one of said first end portion, said second end portion and said middle portion has a higher concentration of said drug than another of said first end portion, said second end portion, and said middle portion. In one optional embodiment, the location of the drug is identified by a detectable marker. The release kinetics of the drug in self-retaining suture may, inter alia, be determined by at least one of the distribution of the retainers, the density of the retainers, the size of the retainers, the surface area of the retainers and the shape of the retainers. Each and every one of these various embodiments may be combined with one or more other optional embodiment as listed herein.

A suture comprising: a filament; a drug associated with the filament; a plurality of tissue retainers formed in the filament; wherein kinetics of the release of the drug is determined by the distribution of the drug in the suture; and wherein said filament includes a core and a sheath that covers said core and wherein said drug is provided in at least one of said core and said sheath with a distribution selected from isotropic and anisotropic. Optionally, one of the core and the sheath has a higher concentration of said drug than the other of the core and the sheath.

A suture comprising: a filament; a drug associated with the filament; a plurality of tissue retainers formed in the filament; wherein kinetics of the release of the drug is determined by the distribution of the therapeutic agent in the suture; and wherein said filament includes a core including a plurality of braided threads and a sheath that covers said core and wherein said drug is provided in at least one of said core and said sheath at least one of isotropically and anisotropically. Optionally, one of the core and the sheath has a higher concentration of said therapeutic agent than the other of the core and the sheath.

A self-retaining suture comprising: a filament; a drug associated with the filament; a plurality of tissue retainers cut into the filament; wherein, after implantation in a tissue, the filament and retainers release the drug into the tissue, the kinetics of releasing the drug being modified by the shape and distribution of the retainers as compared to the filament alone.

A method for nerve repair including the steps of: selecting a suture which includes a Nerve Growth Factor (NGF) and with a plurality of distributed retainers so that the nerve can be repaired and tension applied to the nerve during the repair by the suture is spread along the nerve; and applying the suture to the nerve in order to repair the nerve. Optionally, this method includes selecting a suture wherein more than eighty percent of the NGF is released to the nerve within the first five days after the suture is applied to the nerve in order to repair the nerve. Also optionally, the applying step include applying at least two sutures with bidirectional retainers to the nerve wherein the sutures approximate the nerve along a direction about parallel to the nerve. Optionally, the applying step includes applying the suture to repair the nerve using an anastomosis technique. The applying step may optionally be used on at least one of a lacerated nerve or a ruptured nerve. Optionally, the step of removing necrotic tissue from severed nerve ends before the applying step. Also optionally, said applying step may include using said suture to bridge a nerve defect. In addition, said applying step may optionally include repairing the nerve without a concentration of one of tension or pressure on the nerve.

A method for nerve repair including the steps of: selecting a suture which includes a Nerve Growth Factor (NGF) and with a plurality of distributed retainers so that the nerve can be repaired; and applying the suture to the nerve in order to repair the nerve, wherein the selecting step includes selecting a suture wherein more than eighty percent of the NGF is released to the nerve within the first five days after the suture is applied to the nerve in order to repair the nerve; and wherein said applying step includes repairing the nerve without a concentration of one of tension or pressure on the portion of the nerve that is being repaired. Optionally, this method provides that the applying step include applying at least two sutures with bidirectional retainers to the nerve wherein the sutures approximate the nerve along a direction about parallel to the nerve. Also optionally, the applying step may include applying the suture to repair the nerve using an anastomosis technique. In addition, said applying step may optionally be used on at least one of a lacerated nerve or a ruptured nerve. The method may include the step of removing necrotic tissue from severed nerve ends before the applying step. As an option, said applying step includes using said suture to bridge a nerve defect.

A method for nerve repair including the steps of: selecting a suture which includes a Nerve Growth Factor (NGF) and with a plurality of distributed retainers so that the nerve can be repaired; and applying the suture to the nerve in order to repair the nerve, wherein the selecting step includes selecting a suture suitable for drug burst release kinetics of the NGF; and wherein said applying step includes repairing the nerve without a concentration of one of tension or pressure on the portion of the nerve that is being repaired. As an option, the applying step includes applying at least two sutures with bidirectional retainers to the nerve wherein the sutures approximate the nerve along a direction about parallel to the nerve. Another optional embodiment is that the applying step includes applying the suture to repair the nerve using an anastomosis technique. Said applying step may optionally be used on at least one of a lacerated nerve or a ruptured nerve. The method may include the step of removing necrotic tissue from severed nerve ends before the applying step. The applying step may optionally include using said suture to bridge a nerve defect. In one embodiment, the selecting step includes selecting a suture suitable for drug burst release kinetics of the NGF.

The various optional embodiments set forth above may be combined with one or more other optional embodiments as set forth herein, to provide a statement of the present invention.

Although the present invention has been shown and described in detail with regard to only a few exemplary embodiments of the invention, it should be understood by those skilled in the art that it is not intended to limit the invention to the specific embodiments disclosed. Various modifications, omissions, and additions may be made to the disclosed embodiments without materially departing from the novel teachings and advantages of the invention, particularly in light of the foregoing teachings. Accordingly, it is intended to cover all such modifications, omissions, additions, and equivalents as may be included within the spirit and scope of the invention as defined by the following claims.

What is claimed is:
1. A suture comprising:
(a) a filament, wherein the filament comprises:
  i) a core,
  ii) a sheath,
  iii) a first end portion,
  iv) a second end portion, and
  v) a middle portion between the first end portion and the second end portion;
wherein the sheath comprises a plurality of triangular-shaped sheath elements and wherein each of the plurality of triangular-shaped sheath elements:
  1) is angularly spaced apart from adjacent triangular-shaped sheath elements of the plurality of triangular-shaped sheath elements about a circumference of the core, and
  2) has a base and a tip that is narrower than the base, wherein:
    A. the base is connected to the core, and
    B. the tip extends radially outward from the core;
(b) triclosan associated with the sheath of the filament; and
(c) a plurality of tissue retainers formed in the filament; wherein:
  i) at least one of the first end portion, the second end portion and the middle portion has a higher concentration of the triclosan than another of the first end portion, the second end portion, and the middle portion;
  ii) kinetics of release of the triclosan from the suture is determined by a distribution of the triclosan on the retainers, a density of the retainers, a size of the retainers, a surface area of the retainers and a shape of the retainers; and
  iii) the suture comprises at least one non-degradable material selected from the group of polyamide, polyester, polytetrafluoroethylenes, polyether-ester, 4-hydroxybutyrate, polyhydroxylalkanoate, polyurethane, metals, metal alloys, polypropylene, polyethylene, silk, cotton and combinations thereof.

2. The suture of claim 1, wherein the suture further comprises at least one polymer selected from the group of poly(L-lactic acid), poly(p-dioxanone), poly(DL-lactic acid), polycaprolactone, poly(glycolic acid), polyanhydride, polyglycolic acid homopolymer, copolymers of glycolide and ε-caprolactone, copolymers of glycolide and lactide, copolymers of trimethylene carbonate and glycolide with diethylene glycol, polyhydroxylalkanoates, terpolymer composed of glycolide, trimethylene carbonate and dioxanone, trimethylene carbonate (26%) and dioxanone (14%), copolymers of glycolide, caprolactone, trimethylene carbonate and lactide.

3. The suture of claim 2, wherein the suture further comprises at least one naturally occurring polymer selected from the group of reconstituted collagen, fibrin, natural silks, cellulose, starch, chitin, polypeptides modified polysaccharides, modified proteins and combinations thereof.

4. A suture comprising:
(a) a filament, wherein the filament comprises:
  i) a core,
  ii) a sheath,
  iii) a first end portion,
  iv) a second end portion, and
  v) a middle portion between the first end portion and the second end portion;
  wherein the sheath comprises a plurality of triangular-shaped sheath elements and wherein each of the plurality of triangular-shaped sheath elements:
    1) is angularly spaced apart from adjacent triangular-shaped sheath elements of the plurality of triangular-shaped sheath elements about a circumference of the core, and
    2) has a base and a tip that is narrower than the base, wherein:
      A. the base is connected to the core, and
      B. the tip extends radially outward from the core;
(b) Nerve Growth Factor (NGF) integrated into the filament; and
(c) a plurality of tissue retainers formed in the filament; wherein:
  i) at least one of the first end portion, the second end portion and the middle portion has a higher concentration of the NGF than another of the first end portion, the second end portion, and the middle portion; and
  ii) the kinetics of release of the NGF from the suture is determined by at least one of a distribution of the retainers, a density of the retainers, a size of the retainers, a surface area of the retainers or a shape of the retainers;
  iii) wherein first order burst in-vitro release kinetics of the NGF is such that at least about 80% of the NGF is released from the suture on day 5 after implantation of the suture; and
  iv) the suture comprises at least one non-degradable material selected from the group of polyamide, polyester, polytetrafluoroethylenes, polyether-ester, 4-hydroxybutyrate, polyhydroxyalkanoate, polyurethane, metals, metal alloys, polypropylene, polyethylene, silk, cotton and combinations thereof.

5. The suture of claim 4, wherein the suture further comprises at least one polymer selected from the group of poly(L-lactic acid), poly(p-dioxanone), poly(DL-lactic acid), polycaprolactone, poly(glycolic acid), polyanhydride, polyglycolic acid homopolymer, copolymers of glycolide and ε-caprolactone, copolymers of glycolide and lactide, copolymers of trimethylene carbonate and glycolide with diethylene glycol, polyhydroxylalkanoates, terpolymer composed of glycolide, trimethylene carbonate and dioxanone, trimethylene carbonate (26%) and dioxanone (14%), copolymers of glycolide, caprolactone, trimethylene carbonate and lactide.

6. The suture of claim 5, wherein the suture further comprises at least one naturally occurring polymer selected from the group of reconstituted collagen, fibrin, natural silks, cellulose, starch, chitin, polypeptides modified polysaccharides, modified proteins and combinations thereof.

* * * * *